(12) United States Patent
Quach et al.

(10) Patent No.: US 11,439,449 B2
(45) Date of Patent: *Sep. 13, 2022

(54) SYSTEMS AND METHODS FOR DISTRACTION

(71) Applicant: NuVasive Specialized Orthopedics, Inc., San Diego, CA (US)

(72) Inventors: Ricky Trieu Quach, Irvine, CA (US); Arvin Chang, Yorba Linda, CA (US); Alan J. Arena, Chino, CA (US); Adam G. Beckett, Mission Viejo, CA (US); Mark T. Dahl, South Afton, MN (US)

(73) Assignee: NuVasive Specialized Orthopedics, Inc., San Diego, CA (US)

( * ) Notice: Subject to any disclaimer, the term of this patent is extended or adjusted under 35 U.S.C. 154(b) by 10 days.

This patent is subject to a terminal disclaimer.

(21) Appl. No.: 16/298,339

(22) Filed: Mar. 11, 2019

(65) Prior Publication Data

US 2019/0201067 A1    Jul. 4, 2019

Related U.S. Application Data

(63) Continuation of application No. 14/981,762, filed on Dec. 28, 2015, now Pat. No. 10,271,885.

(Continued)

(51) Int. Cl.
*A61B 17/88*    (2006.01)
*A61B 17/70*    (2006.01)
(Continued)

(52) U.S. Cl.
CPC ...... *A61B 17/8866* (2013.01); *A61B 17/7004* (2013.01); *A61B 17/7014* (2013.01);
(Continued)

(58) Field of Classification Search
CPC ..... A61B 17/88; A61B 17/8866; A61B 17/70; A61B 17/7004; A61B 17/7014;
(Continued)

(56) References Cited

U.S. PATENT DOCUMENTS 1,599,538 A     9/1926 Ludger
2,391,537 A *  12/1945 Anderson ............. A61B 17/66
                                                  606/59

(Continued)

FOREIGN PATENT DOCUMENTS

AU    20068468    3/2001
CN    101040807   9/2007
(Continued)

OTHER PUBLICATIONS

US 9,161,784 B2, 10/2015, Buttermann (withdrawn)
(Continued)

*Primary Examiner* — Christopher J Beccia
(74) *Attorney, Agent, or Firm* — Hoffman Warnick LLC

(57) ABSTRACT

A system for moving a portion of a patient's body including a housing having a first cavity extending along a longitudinal axis, a first distraction rod having a proximal end and a distal end, the first distraction rod and the housing being telescopically displaceable with respect to each other along the longitudinal axis, the first distraction rod having a cavity extending along the longitudinal axis, a second distraction rod having a proximal end and a distal end and configured to be telescopically displaceable from within the second cavity along the longitudinal axis, and a drive system configured to move the first distraction rod in relation to the housing and to move the second distraction rod in relation to the first distraction rod.

19 Claims, 10 Drawing Sheets

Related U.S. Application Data

(60) Provisional application No. 62/097,005, filed on Dec. 26, 2014.

(51) Int. Cl.
  *A61B 50/20* (2016.01)
  *A61B 50/30* (2016.01)
  *A61B 50/33* (2016.01)
  *A61B 50/34* (2016.01)
  *A61B 17/72* (2006.01)
  *A61B 17/68* (2006.01)
  *A61B 17/56* (2006.01)

(52) U.S. Cl.
  CPC ...... *A61B 17/7016* (2013.01); *A61B 17/7017* (2013.01); *A61B 17/7216* (2013.01); *A61B 50/20* (2016.02); *A61B 50/30* (2016.02); *A61B 50/33* (2016.02); *A61B 50/34* (2016.02); *A61B 2017/564* (2013.01); *A61B 2017/681* (2013.01)

(58) Field of Classification Search
  CPC . A61B 17/7016; A61B 17/7017; A61B 17/72; A61B 17/7216; A61B 50/20; A61B 50/33; A61B 50/34
  See application file for complete search history.

(56) References Cited

U.S. PATENT DOCUMENTS

| | | |
|---|---|---|
| 3,111,945 A | 11/1963 | Von |
| 3,372,476 A | 3/1968 | Richard et al. |
| 3,377,576 A | 4/1968 | Edwin et al. |
| 3,397,928 A | 8/1968 | Galle |
| 3,512,901 A | 5/1970 | Law |
| 3,527,220 A | 9/1970 | Summers |
| 3,597,781 A | 8/1971 | Eibes et al. |
| 3,726,279 A | 4/1973 | Barefoot et al. |
| 3,749,098 A | 7/1973 | De Bennetot |
| 3,750,194 A | 8/1973 | Summers |
| 3,810,259 A | 5/1974 | Summers |
| 3,840,018 A | 10/1974 | Heifetz |
| 3,866,510 A | 2/1975 | Eibes et al. |
| 3,900,025 A | 8/1975 | Barnes, Jr. |
| 3,915,151 A | 10/1975 | Kraus |
| RE28,907 E | 7/1976 | Eibes et al. |
| 3,976,060 A | 8/1976 | Hildebrandt et al. |
| 4,010,758 A | 3/1977 | Rockland et al. |
| 4,056,743 A | 11/1977 | Clifford et al. |
| 4,068,821 A | 1/1978 | Morrison |
| 4,078,559 A | 3/1978 | Nissinen |
| 4,118,805 A | 10/1978 | Reimels |
| 4,204,541 A | 5/1980 | Kapitanov |
| 4,222,374 A | 9/1980 | Sampson et al. |
| 4,235,246 A | 11/1980 | Weiss |
| 4,256,094 A | 3/1981 | Kapp et al. |
| 4,286,584 A | 9/1981 | Sampson et al. |
| 4,300,223 A | 11/1981 | Maire |
| 4,357,946 A | 11/1982 | Dutcher et al. |
| 4,386,603 A | 6/1983 | Mayfield |
| 4,395,259 A | 7/1983 | Prestele et al. |
| 4,448,191 A | 5/1984 | Rodnyansky et al. |
| 4,486,176 A | 12/1984 | Tardieu et al. |
| 4,501,266 A | 2/1985 | McDaniel |
| 4,522,501 A | 6/1985 | Shannon |
| 4,537,520 A | 8/1985 | Ochiai et al. |
| 4,550,279 A | 10/1985 | Klein |
| 4,561,798 A | 12/1985 | Elcrin et al. |
| 4,573,454 A | 3/1986 | Hoffman |
| 4,592,339 A | 6/1986 | Kuzmak et al. |
| 4,592,355 A | 6/1986 | Antebi |
| 4,595,007 A | 6/1986 | Mericle |
| 4,642,257 A | 2/1987 | Chase |
| 4,658,809 A | 4/1987 | Ulrich et al. |
| 4,696,288 A | 9/1987 | Kuzmak et al. |
| 4,700,091 A | 10/1987 | Wuthrich |
| 4,747,832 A | 5/1988 | Buffet |
| 4,760,837 A | 8/1988 | Petit |
| 4,854,304 A | 8/1989 | Zielke |
| 4,872,515 A | 10/1989 | Lundell |
| 4,904,861 A | 2/1990 | Epstein et al. |
| 4,931,055 A | 6/1990 | Bumpus et al. |
| 4,940,467 A | 7/1990 | Tronzo |
| 4,957,495 A | 9/1990 | Kluger |
| 4,973,331 A | 11/1990 | Pursley et al. |
| 4,978,323 A | 12/1990 | Freedman |
| 4,998,013 A | 3/1991 | Epstein et al. |
| 5,010,879 A | 4/1991 | Moriya et al. |
| 5,030,235 A | 7/1991 | Campbell, Jr. |
| 5,041,112 A | 8/1991 | Mingozzi et al. |
| 5,053,047 A | 10/1991 | Yoon |
| 5,064,004 A | 11/1991 | Lundell |
| 5,074,868 A | 12/1991 | Kuzmak |
| 5,074,882 A | 12/1991 | Grammont et al. |
| 5,092,889 A | 3/1992 | Campbell, Jr. |
| 5,133,716 A | 7/1992 | Plaza |
| 5,142,407 A | 8/1992 | Varaprasad et al. |
| 5,152,770 A | 10/1992 | Bengmark et al. |
| 5,156,605 A | 10/1992 | Pursley et al. |
| 5,176,618 A | 1/1993 | Freedman |
| 5,180,380 A | 1/1993 | Pursley et al. |
| 5,222,976 A | 6/1993 | Yoon |
| 5,226,429 A | 7/1993 | Kuzmak |
| 5,261,908 A | 11/1993 | Campbell, Jr. |
| 5,263,955 A | 11/1993 | Baumgart et al. |
| 5,290,289 A | 3/1994 | Sanders et al. |
| 5,306,275 A | 4/1994 | Bryan |
| 5,330,503 A | 7/1994 | Yoon |
| 5,334,202 A | 8/1994 | Carter |
| 5,336,223 A | 8/1994 | Rogers |
| 5,356,411 A | 10/1994 | Spievack |
| 5,356,424 A | 10/1994 | Buzerak et al. |
| 5,360,407 A | 11/1994 | Leonard et al. |
| 5,364,396 A | 11/1994 | Robinson et al. |
| 5,381,943 A | 1/1995 | Allen et al. |
| 5,399,168 A | 3/1995 | Wadsworth, Jr. et al. |
| 5,403,322 A | 4/1995 | Herzenberg et al. |
| 5,429,638 A | 7/1995 | Muschler et al. |
| 5,433,721 A | 7/1995 | Hooven et al. |
| 5,437,266 A | 8/1995 | McPherson et al. |
| 5,449,368 A | 9/1995 | Kuzmak |
| 5,466,261 A | 11/1995 | Richelsoph |
| 5,468,030 A | 11/1995 | Walling |
| 5,480,437 A | 1/1996 | Draenert |
| 5,498,262 A | 3/1996 | Bryan |
| 5,509,888 A | 4/1996 | Miller |
| 5,516,335 A | 5/1996 | Kummer et al. |
| 5,527,309 A | 6/1996 | Shelton |
| 5,536,269 A | 7/1996 | Spievack |
| 5,536,296 A | 7/1996 | Ten Eyck et al. |
| 5,549,610 A | 8/1996 | Russell et al. |
| 5,573,496 A | 11/1996 | McPherson et al. |
| 5,575,790 A | 11/1996 | Chen et al. |
| 5,582,616 A | 12/1996 | Bolduc et al. |
| 5,601,224 A | 2/1997 | Bishop et al. |
| 5,620,445 A | 4/1997 | Brosnahan et al. |
| 5,620,449 A | 4/1997 | Faccioli et al. |
| 5,626,579 A | 5/1997 | Muschler et al. |
| 5,626,613 A | 5/1997 | Schmieding |
| 5,628,888 A | 5/1997 | Bakhir et al. |
| 5,632,744 A | 5/1997 | Campbell, Jr. |
| 5,659,217 A | 8/1997 | Petersen |
| 5,662,683 A | 9/1997 | Kay |
| 5,672,175 A | 9/1997 | Martin |
| 5,672,177 A | 9/1997 | Seldin |
| 5,676,162 A | 10/1997 | Larson, Jr. et al. |
| 5,693,091 A | 12/1997 | Larson, Jr. et al. |
| 5,700,263 A | 12/1997 | Schendel |
| 5,702,430 A | 12/1997 | Larson, Jr. et al. |
| 5,704,893 A | 1/1998 | Timm |
| 5,704,938 A | 1/1998 | Staehlin et al. |
| 5,704,939 A | 1/1998 | Justin |
| 5,720,746 A | 2/1998 | Soubeiran |
| 5,722,429 A | 3/1998 | Larson, Jr. et al. |

(56) References Cited

U.S. PATENT DOCUMENTS

| | | | |
|---|---|---|---|
| 5,722,930 A | 3/1998 | Larson, Jr. et al. |
| 5,743,910 A | 4/1998 | Bays et al. |
| 5,758,666 A | 6/1998 | Larson, Jr. et al. |
| 5,762,599 A | 6/1998 | Sohn |
| 5,766,208 A | 6/1998 | McEwan |
| 5,771,903 A | 6/1998 | Jakobsson |
| 5,800,434 A | 9/1998 | Campbell, Jr. |
| 5,810,815 A | 9/1998 | Morales |
| 5,824,008 A | 10/1998 | Bolduc et al. |
| 5,827,286 A | 10/1998 | Incavo et al. |
| 5,829,662 A | 11/1998 | Allen et al. |
| 5,830,221 A | 11/1998 | Stein et al. |
| 5,843,129 A | 12/1998 | Larson, Jr. et al. |
| 5,874,796 A | 2/1999 | Petersen |
| 5,879,375 A | 3/1999 | Larson, Jr. et al. |
| 5,902,304 A | 5/1999 | Walker et al. |
| 5,935,127 A | 8/1999 | Border |
| 5,938,669 A | 8/1999 | Klaiber et al. |
| 5,945,762 A | 8/1999 | Chen et al. |
| 5,954,915 A | 9/1999 | Voorhees et al. |
| 5,961,553 A | 10/1999 | Coty et al. |
| 5,964,763 A | 10/1999 | Incavo et al. |
| 5,976,138 A | 11/1999 | Baumgart et al. |
| 5,979,456 A | 11/1999 | Magovern |
| 5,985,110 A | 11/1999 | Bakhir et al. |
| 5,997,490 A | 12/1999 | McLeod et al. |
| 6,009,837 A | 1/2000 | McClasky |
| 6,022,349 A | 2/2000 | McLeod et al. |
| 6,033,412 A | 3/2000 | Losken et al. |
| 6,034,296 A | 3/2000 | Elvin et al. |
| 6,067,991 A | 5/2000 | Forsell |
| 6,074,341 A | 6/2000 | Anderson et al. |
| 6,074,882 A | 6/2000 | Eckardt |
| 6,092,531 A | 7/2000 | Chen et al. |
| 6,102,922 A | 8/2000 | Jakobsson et al. |
| 6,106,525 A | 8/2000 | Sachse |
| 6,126,660 A | 10/2000 | Dietz |
| 6,126,661 A | 10/2000 | Faccioli et al. |
| 6,138,681 A | 10/2000 | Chen et al. |
| 6,139,316 A | 10/2000 | Sachdeva et al. |
| 6,162,223 A | 12/2000 | Orsak et al. |
| 6,183,476 B1 | 2/2001 | Gerhardt et al. |
| 6,200,317 B1 | 3/2001 | Aalsma et al. |
| 6,203,548 B1 * | 3/2001 | Holland ................ A61B 17/66 |
| | | | 606/105 |
| 6,210,347 B1 | 4/2001 | Forsell |
| 6,217,847 B1 | 4/2001 | Contag et al. |
| 6,221,074 B1 | 4/2001 | Cole et al. |
| 6,234,299 B1 | 5/2001 | Voorhees et al. |
| 6,234,956 B1 | 5/2001 | He et al. |
| 6,241,730 B1 | 6/2001 | Alby |
| 6,245,075 B1 | 6/2001 | Betz et al. |
| 6,283,156 B1 | 9/2001 | Motley |
| 6,296,643 B1 | 10/2001 | Hopf et al. |
| 6,296,656 B1 | 10/2001 | Bolduc et al. |
| 6,299,613 B1 | 10/2001 | Ogilvie et al. |
| 6,315,784 B1 | 11/2001 | Djurovic |
| 6,319,255 B1 | 11/2001 | Grundei et al. |
| 6,321,106 B1 | 11/2001 | Lemelson |
| 6,325,805 B1 | 12/2001 | Ogilvie et al. |
| 6,327,492 B1 | 12/2001 | Lemelson |
| 6,331,744 B1 | 12/2001 | Chen et al. |
| 6,336,929 B1 | 1/2002 | Justin |
| 6,343,568 B1 * | 2/2002 | McClasky ............... A01K 31/14 |
| | | | 119/428 |
| 6,358,283 B1 | 3/2002 | Hogfors et al. |
| 6,375,682 B1 | 4/2002 | Fleischmann et al. |
| 6,386,083 B1 | 5/2002 | Hwang |
| 6,389,187 B1 | 5/2002 | Greenaway et al. |
| 6,400,980 B1 | 6/2002 | Lemelson |
| 6,402,753 B1 | 6/2002 | Cole et al. |
| 6,409,175 B1 | 6/2002 | Evans et al. |
| 6,416,516 B1 | 7/2002 | Stanch et al. |
| 6,417,750 B1 | 7/2002 | Sohn |
| 6,423,061 B1 | 7/2002 | Bryant |
| 6,432,040 B1 | 8/2002 | Meah |
| 6,450,173 B1 | 9/2002 | Forsell |
| 6,450,946 B1 | 9/2002 | Forsell |
| 6,453,907 B1 | 9/2002 | Forsell |
| 6,454,698 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,460,543 B1 | 10/2002 | Forsell |
| 6,461,292 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,471,635 B1 | 10/2002 | Forsell |
| 6,475,136 B1 | 11/2002 | Forsell |
| 6,482,145 B1 | 11/2002 | Forsell |
| 6,494,879 B2 | 12/2002 | Lennox et al. |
| 6,499,907 B1 | 12/2002 | Baur |
| 6,500,110 B1 | 12/2002 | Davey et al. |
| 6,503,189 B1 | 1/2003 | Forsell |
| 6,508,820 B2 | 1/2003 | Bales |
| 6,510,345 B1 | 1/2003 | Van Bentem |
| 6,511,490 B2 | 1/2003 | Robert |
| 6,527,701 B1 | 3/2003 | Sayet et al. |
| 6,527,702 B2 | 3/2003 | Whalen et al. |
| 6,536,499 B2 | 3/2003 | Voorhees et al. |
| 6,537,196 B1 | 3/2003 | Creighton, IV et al. |
| 6,547,801 B1 | 4/2003 | Dargent et al. |
| 6,554,831 B1 | 4/2003 | Rivard et al. |
| 6,558,400 B2 | 5/2003 | Deem et al. |
| 6,562,051 B1 | 5/2003 | Bolduc et al. |
| 6,565,573 B1 | 5/2003 | Ferrante et al. |
| 6,565,576 B1 | 5/2003 | Stauch et al. |
| 6,573,706 B2 | 6/2003 | Mendes et al. |
| 6,582,313 B2 | 6/2003 | Perrow |
| 6,583,630 B2 | 6/2003 | Mendes et al. |
| 6,587,719 B1 | 7/2003 | Barrett et al. |
| 6,595,912 B2 | 7/2003 | Lau et al. |
| 6,602,184 B2 | 8/2003 | Lau et al. |
| 6,604,529 B2 | 8/2003 | Kim |
| 6,607,363 B1 | 8/2003 | Domroese |
| 6,609,025 B2 | 8/2003 | Barrett et al. |
| 6,612,978 B2 | 9/2003 | Lau et al. |
| 6,612,979 B2 | 9/2003 | Lau et al. |
| 6,616,669 B2 | 9/2003 | Ogilvie et al. |
| 6,621,956 B2 | 9/2003 | Greenaway et al. |
| 6,626,899 B2 | 9/2003 | Houser et al. |
| 6,626,917 B1 | 9/2003 | Craig |
| 6,627,206 B2 | 9/2003 | Lloyd |
| 6,649,143 B1 | 11/2003 | Contag et al. |
| 6,656,135 B2 | 12/2003 | Zogbi et al. |
| 6,656,194 B1 | 12/2003 | Gannoe et al. |
| 6,657,351 B2 | 12/2003 | Chen et al. |
| 6,667,725 B1 | 12/2003 | Simons et al. |
| 6,669,687 B1 | 12/2003 | Saadat |
| 6,673,079 B1 | 1/2004 | Kane |
| 6,676,674 B1 | 1/2004 | Dudai |
| 6,682,474 B2 | 1/2004 | Lau et al. |
| 6,689,046 B2 | 2/2004 | Sayet et al. |
| 6,702,732 B1 | 3/2004 | Lau et al. |
| 6,702,816 B2 | 3/2004 | Buhler |
| 6,706,042 B2 | 3/2004 | Taylor |
| 6,709,293 B2 | 3/2004 | Mori et al. |
| 6,709,385 B2 | 3/2004 | Forsell |
| 6,730,087 B1 | 5/2004 | Butsch |
| 6,749,556 B2 | 6/2004 | Banik |
| 6,752,754 B1 | 6/2004 | Feng et al. |
| 6,761,503 B2 | 7/2004 | Breese |
| 6,765,330 B2 | 7/2004 | Baur |
| 6,769,499 B2 | 8/2004 | Cargill et al. |
| 6,773,437 B2 | 8/2004 | Ogilvie et al. |
| 6,774,624 B2 | 8/2004 | Anderson et al. |
| 6,789,442 B2 | 9/2004 | Forch |
| 6,796,984 B2 | 9/2004 | Soubeiran |
| 6,802,844 B2 | 10/2004 | Ferree |
| 6,802,847 B1 | 10/2004 | Carson et al. |
| 6,809,434 B1 | 10/2004 | Duncan et al. |
| 6,835,183 B2 | 12/2004 | Lennox et al. |

(56) References Cited

U.S. PATENT DOCUMENTS

| | | |
|---|---|---|
| 6,835,207 B2 | 12/2004 | Zacouto et al. |
| 6,849,076 B2 | 2/2005 | Blunn et al. |
| 6,852,113 B2 | 2/2005 | Nathanson et al. |
| 6,864,647 B2 | 3/2005 | Duncan et al. |
| 6,884,248 B2 | 4/2005 | Bolduc et al. |
| 6,890,515 B2 | 5/2005 | Contag et al. |
| 6,908,605 B2 | 6/2005 | Contag et al. |
| 6,915,165 B2 | 7/2005 | Forsell |
| 6,916,462 B2 | 7/2005 | Contag et al. |
| 6,918,838 B2 | 7/2005 | Schwarzler et al. |
| 6,918,910 B2 | 7/2005 | Smith et al. |
| 6,921,360 B2 | 7/2005 | Banik |
| 6,921,400 B2 | 7/2005 | Sohngen |
| 6,923,951 B2 | 8/2005 | Contag et al. |
| 6,926,719 B2 | 8/2005 | Sohngen et al. |
| 6,939,533 B2 | 9/2005 | Contag et al. |
| 6,953,429 B2 | 10/2005 | Forsell |
| 6,961,553 B2 | 11/2005 | Zhao et al. |
| 6,971,143 B2 | 12/2005 | Domroese |
| 6,980,921 B2 | 12/2005 | Anderson et al. |
| 6,997,952 B2 | 2/2006 | Furukawa et al. |
| 7,001,327 B2 | 2/2006 | Whalen et al. |
| 7,001,346 B2 | 2/2006 | White |
| 7,008,425 B2 | 3/2006 | Phillips |
| 7,011,621 B2 | 3/2006 | Sayet et al. |
| 7,011,658 B2 | 3/2006 | Young |
| 7,011,682 B2 | 3/2006 | Lashinski et al. |
| 7,018,380 B2 | 3/2006 | Cole |
| 7,029,475 B2 | 4/2006 | Panjabi |
| 7,041,105 B2 | 5/2006 | Michelson |
| 7,060,075 B2 | 6/2006 | Govari et al. |
| 7,060,080 B2 | 6/2006 | Bachmann |
| 7,063,706 B2 | 6/2006 | Wittenstein |
| 7,077,802 B2 | 7/2006 | Lau et al. |
| 7,081,086 B2 | 7/2006 | Lau et al. |
| 7,083,629 B2 | 8/2006 | Weller et al. |
| 7,096,148 B2 | 8/2006 | Anderson et al. |
| 7,097,611 B2 | 8/2006 | Lau et al. |
| 7,105,029 B2 | 9/2006 | Doubler et al. |
| 7,105,968 B2 | 9/2006 | Nissen |
| 7,114,501 B2 | 10/2006 | Johnson et al. |
| 7,115,129 B2 | 10/2006 | Heggeness |
| 7,115,130 B2 | 10/2006 | Michelson |
| 7,124,493 B2 | 10/2006 | Lau et al. |
| 7,128,707 B2 | 10/2006 | Banik |
| 7,135,022 B2 | 11/2006 | Kosashvili et al. |
| 7,160,312 B2 | 1/2007 | Saadat |
| 7,163,538 B2 | 1/2007 | Altarac et al. |
| 7,172,607 B2 | 2/2007 | Hofle et al. |
| 7,175,589 B2 | 2/2007 | Deem et al. |
| 7,175,660 B2 | 2/2007 | Cartledge et al. |
| 7,186,262 B2 | 3/2007 | Saadat |
| 7,188,627 B2 | 3/2007 | Nelson et al. |
| 7,189,005 B2 | 3/2007 | Ward |
| 7,189,202 B2 | 3/2007 | Lau et al. |
| 7,189,251 B2 | 3/2007 | Kay |
| 7,191,007 B2 | 3/2007 | Desai et al. |
| 7,194,297 B2 | 3/2007 | Talpade et al. |
| 7,195,608 B2 | 3/2007 | Burnett |
| 7,198,774 B2 | 4/2007 | Contag et al. |
| 7,211,094 B2 | 5/2007 | Gannoe et al. |
| 7,216,648 B2 | 5/2007 | Nelson et al. |
| 7,217,284 B2 | 5/2007 | Houser et al. |
| 7,218,232 B2 | 5/2007 | DiSilvestro et al. |
| 7,232,449 B2 | 6/2007 | Sharkawy et al. |
| 7,234,468 B2 | 6/2007 | Johnson et al. |
| 7,234,544 B2 | 6/2007 | Kent |
| 7,238,152 B2 | 7/2007 | Lau et al. |
| 7,238,191 B2 | 7/2007 | Bachmann |
| 7,241,300 B2 | 7/2007 | Sharkawy et al. |
| 7,243,719 B2 | 7/2007 | Baron et al. |
| 7,255,682 B1 | 8/2007 | Bartol, Jr. et al. |
| 7,255,714 B2 | 8/2007 | Malek |
| 7,255,851 B2 | 8/2007 | Contag et al. |
| 7,276,022 B2 | 10/2007 | Lau et al. |
| 7,282,023 B2 | 10/2007 | Frering |
| 7,285,087 B2 | 10/2007 | Moaddeb et al. |
| 7,288,064 B2 | 10/2007 | Boustani et al. |
| 7,288,099 B2 | 10/2007 | Deem et al. |
| 7,288,101 B2 | 10/2007 | Deem et al. |
| 7,296,577 B2 | 11/2007 | Lashinski et al. |
| 7,297,150 B2 | 11/2007 | Cartledge et al. |
| 7,299,091 B2 | 11/2007 | Barrett et al. |
| 7,302,858 B2 | 12/2007 | Walsh et al. |
| 7,306,614 B2 | 12/2007 | Weller et al. |
| 7,311,690 B2 | 12/2007 | Burnett |
| 7,314,372 B2 | 1/2008 | Belfor et al. |
| 7,314,443 B2 | 1/2008 | Jordan et al. |
| 7,320,706 B2 | 1/2008 | Al-Najjar |
| 7,331,995 B2 | 2/2008 | Eisermann et al. |
| 7,333,013 B2 | 2/2008 | Berger |
| 7,338,433 B2 | 3/2008 | Coe |
| 7,340,306 B2 | 3/2008 | Barrett et al. |
| 7,351,198 B2 | 4/2008 | Byrum et al. |
| 7,351,240 B2 | 4/2008 | Hassler, Jr. et al. |
| 7,353,747 B2 | 4/2008 | Swayze et al. |
| 7,357,037 B2 | 4/2008 | Hnat et al. |
| 7,357,635 B2 | 4/2008 | Belfor et al. |
| 7,360,542 B2 | 4/2008 | Nelson et al. |
| 7,361,192 B2 | 4/2008 | Doty |
| 7,364,542 B2 | 4/2008 | Jambor et al. |
| 7,364,589 B2 | 4/2008 | Eisermann |
| 7,367,340 B2 | 5/2008 | Nelson et al. |
| 7,367,937 B2 | 5/2008 | Jambor et al. |
| 7,367,938 B2 | 5/2008 | Forsell |
| 7,371,244 B2 | 5/2008 | Chatlynne et al. |
| 7,374,557 B2 | 5/2008 | Conlon et al. |
| 7,390,007 B2 | 6/2008 | Helms et al. |
| 7,390,294 B2 | 6/2008 | Hassler, Jr. |
| 7,400,926 B2 | 7/2008 | Forsell |
| 7,402,134 B2 | 7/2008 | Moaddeb et al. |
| 7,402,176 B2 | 7/2008 | Malek |
| 7,410,461 B2 | 8/2008 | Lau et al. |
| 7,416,528 B2 | 8/2008 | Crawford et al. |
| 7,422,566 B2 | 9/2008 | Miethke |
| 7,429,259 B2 | 9/2008 | Cadeddu et al. |
| 7,431,692 B2 | 10/2008 | Zollinger et al. |
| 7,441,559 B2 | 10/2008 | Nelson et al. |
| 7,442,196 B2 | 10/2008 | Fisher et al. |
| 7,445,010 B2 | 11/2008 | Kugler et al. |
| 7,455,690 B2 | 11/2008 | Cartledge et al. |
| 7,458,981 B2 | 12/2008 | Fielding et al. |
| 7,468,060 B2 | 12/2008 | Utley et al. |
| 7,476,195 B2 | 1/2009 | Sayet et al. |
| 7,476,238 B2 | 1/2009 | Panjabi |
| 7,481,224 B2 | 1/2009 | Nelson et al. |
| 7,481,763 B2 | 1/2009 | Hassler, Jr. et al. |
| 7,481,841 B2 | 1/2009 | Hazebrouck et al. |
| 7,485,149 B1 | 2/2009 | White |
| 7,489,495 B2 | 2/2009 | Stevenson |
| 7,494,459 B2 | 2/2009 | Anstadt et al. |
| 7,500,484 B2 | 3/2009 | Nelson et al. |
| 7,503,922 B2 | 3/2009 | Deem et al. |
| 7,503,934 B2 | 3/2009 | Eisermann et al. |
| 7,507,252 B2 | 3/2009 | Lashinski et al. |
| 7,510,559 B2 | 3/2009 | Deem et al. |
| 7,530,981 B2 | 5/2009 | Kutsenko |
| 7,531,002 B2 | 5/2009 | Sutton et al. |
| 7,547,291 B2 | 6/2009 | Lennox et al. |
| 7,553,298 B2 | 6/2009 | Hunt et al. |
| 7,559,951 B2 | 7/2009 | DiSilvestro et al. |
| 7,561,916 B2 | 7/2009 | Hunt et al. |
| 7,562,660 B2 | 7/2009 | Saadat |
| 7,566,297 B2 | 7/2009 | Banik |
| 7,569,057 B2 | 8/2009 | Liu et al. |
| 7,578,821 B2 | 8/2009 | Fisher et al. |
| 7,584,788 B2 | 9/2009 | Baron et al. |
| 7,594,887 B2 | 9/2009 | Moaddeb et al. |
| 7,601,156 B2 | 10/2009 | Robinson |
| 7,601,162 B2 | 10/2009 | Hassler, Jr. et al. |
| 7,601,171 B2 | 10/2009 | Ainsworth et al. |
| 7,611,526 B2 | 11/2009 | Carl et al. |
| 7,615,001 B2 | 11/2009 | Jambor et al. |
| 7,615,068 B2 | 11/2009 | Timm et al. |

(56) References Cited

U.S. PATENT DOCUMENTS

| | | |
|---|---|---|
| 7,618,435 B2 | 11/2009 | Opolski |
| 7,621,886 B2 | 11/2009 | Burnett |
| 7,635,379 B2 | 12/2009 | Callahan et al. |
| 7,651,483 B2 | 1/2010 | Byrum et al. |
| 7,658,753 B2 | 2/2010 | Carl et al. |
| 7,666,132 B2 | 2/2010 | Forsell |
| 7,666,184 B2 | 2/2010 | Stauch |
| 7,666,210 B2 | 2/2010 | Franck et al. |
| 7,678,136 B2 | 3/2010 | Doubler et al. |
| 7,678,139 B2 | 3/2010 | Garamszegi et al. |
| 7,691,144 B2 | 4/2010 | Chang et al. |
| 7,695,512 B2 | 4/2010 | Lashinski et al. |
| 7,704,279 B2 | 4/2010 | Moskowitz et al. |
| 7,704,282 B2 | 4/2010 | Disilvestro et al. |
| 7,708,737 B2 | 5/2010 | Kraft et al. |
| 7,708,762 B2 | 5/2010 | McCarthy et al. |
| 7,708,765 B2 | 5/2010 | Carl et al. |
| 7,708,779 B2 | 5/2010 | Edie et al. |
| 7,713,287 B2 | 5/2010 | Timm et al. |
| 7,717,959 B2 | 5/2010 | William et al. |
| 7,727,141 B2 | 6/2010 | Hassler, Jr. et al. |
| 7,727,143 B2 | 6/2010 | Birk et al. |
| 7,749,224 B2 | 7/2010 | Cresina et al. |
| 7,753,913 B2 | 7/2010 | Szakelyhidi, Jr. et al. |
| 7,753,915 B1 | 7/2010 | Eksler et al. |
| 7,757,552 B2 | 7/2010 | Bogath et al. |
| 7,762,998 B2 | 7/2010 | Birk et al. |
| 7,763,053 B2 | 7/2010 | Gordon |
| 7,763,080 B2 | 7/2010 | Southworth |
| 7,766,815 B2 | 8/2010 | Ortiz |
| 7,775,099 B2 | 8/2010 | Bogath et al. |
| 7,775,215 B2 | 8/2010 | Hassler, Jr. et al. |
| 7,776,061 B2 | 8/2010 | Garner et al. |
| 7,776,068 B2 | 8/2010 | Ainsworth et al. |
| 7,776,075 B2 | 8/2010 | Bruneau et al. |
| 7,776,091 B2 | 8/2010 | Mastrorio et al. |
| 7,780,590 B2 | 8/2010 | Birk et al. |
| 7,787,958 B2 | 8/2010 | Stevenson |
| 7,789,912 B2 | 9/2010 | Manzi et al. |
| 7,793,583 B2 | 9/2010 | Radinger et al. |
| 7,794,447 B2 | 9/2010 | Dann et al. |
| 7,794,476 B2 | 9/2010 | Wisnewski |
| 7,798,954 B2 | 9/2010 | Birk et al. |
| 7,799,080 B2 | 9/2010 | Doty |
| 7,803,106 B2 | 9/2010 | Whalen et al. |
| 7,803,157 B2 | 9/2010 | Michelson |
| 7,811,275 B2 | 10/2010 | Birk et al. |
| 7,811,298 B2 | 10/2010 | Birk |
| 7,811,328 B2 | 10/2010 | Molz, IV et al. |
| 7,815,643 B2 | 10/2010 | Johnson et al. |
| 7,828,714 B2 | 11/2010 | Feng et al. |
| 7,828,813 B2 | 11/2010 | Mouton |
| 7,833,228 B1 | 11/2010 | Hershberger |
| 7,835,779 B2 | 11/2010 | Anderson et al. |
| 7,837,669 B2 | 11/2010 | Dann et al. |
| 7,837,691 B2 | 11/2010 | Cordes et al. |
| 7,842,036 B2 | 11/2010 | Phillips |
| 7,845,356 B2 | 12/2010 | Paraschac et al. |
| 7,846,188 B2 | 12/2010 | Moskowitz et al. |
| 7,850,660 B2 | 12/2010 | Uth et al. |
| 7,850,735 B2 | 12/2010 | Eisermann et al. |
| 7,854,769 B2 | 12/2010 | Hershberger |
| 7,862,546 B2 | 1/2011 | Conlon et al. |
| 7,862,574 B2 | 1/2011 | Deem et al. |
| 7,862,586 B2 | 1/2011 | Malek |
| 7,867,235 B2 | 1/2011 | Fell et al. |
| 7,871,368 B2 | 1/2011 | Zollinger et al. |
| 7,875,033 B2 | 1/2011 | Richter et al. |
| 7,887,566 B2 | 2/2011 | Hynes |
| 7,901,381 B2 | 3/2011 | Birk et al. |
| 7,901,419 B2 | 3/2011 | Bachmann et al. |
| 7,909,790 B2 | 3/2011 | Burnett |
| 7,909,838 B2 | 3/2011 | Deem et al. |
| 7,909,839 B2 | 3/2011 | Fields |
| 7,909,852 B2 | 3/2011 | Boomer et al. |
| 7,918,844 B2 | 4/2011 | Byrum et al. |
| 7,921,850 B2 | 4/2011 | Nelson et al. |
| 7,922,765 B2 | 4/2011 | Reiley |
| 7,927,354 B2 | 4/2011 | Edidin et al. |
| 7,927,357 B2 | 4/2011 | Sacher et al. |
| 7,931,679 B2 | 4/2011 | Heggeness |
| 7,932,825 B2 | 4/2011 | Berger |
| 7,938,836 B2 | 5/2011 | Ainsworth et al. |
| 7,938,841 B2 | 5/2011 | Sharkawy et al. |
| 7,942,903 B2 | 5/2011 | Moskowitz et al. |
| 7,942,908 B2 | 5/2011 | Sacher et al. |
| 7,947,011 B2 | 5/2011 | Birk et al. |
| 7,951,067 B2 | 5/2011 | Byrum et al. |
| 7,951,180 B2 | 5/2011 | Moskowitz et al. |
| 7,958,895 B2 | 6/2011 | Nelson et al. |
| 7,958,896 B2 | 6/2011 | Nelson et al. |
| 7,959,552 B2 | 6/2011 | Jordan et al. |
| 7,972,315 B2 | 7/2011 | Birk et al. |
| 7,972,346 B2 | 7/2011 | Bachmann et al. |
| 7,972,363 B2 | 7/2011 | Moskowitz et al. |
| 7,976,545 B2 | 7/2011 | Hershberger et al. |
| 7,983,763 B2 | 7/2011 | Stevenson et al. |
| 7,985,256 B2 | 7/2011 | Grotz et al. |
| 7,987,241 B2 | 7/2011 | St Jacques, Jr. et al. |
| 7,988,707 B2 | 8/2011 | Panjabi |
| 7,988,709 B2 | 8/2011 | Clark et al. |
| 7,993,342 B2 | 8/2011 | Malandain et al. |
| 7,993,397 B2 | 8/2011 | Lashinski et al. |
| 7,998,174 B2 | 8/2011 | Malandain et al. |
| 7,998,208 B2 | 8/2011 | Kohm et al. |
| 8,002,801 B2 | 8/2011 | Carl et al. |
| 8,002,809 B2 | 8/2011 | Baynham |
| 8,007,458 B2 | 8/2011 | Lennox et al. |
| 8,007,474 B2 | 8/2011 | Uth et al. |
| 8,007,479 B2 | 8/2011 | Birk et al. |
| 8,011,308 B2 | 9/2011 | Picchio |
| 8,012,162 B2 | 9/2011 | Bachmann |
| 8,016,745 B2 | 9/2011 | Hassler, Jr. et al. |
| 8,016,837 B2 | 9/2011 | Giger et al. |
| 8,016,860 B2 | 9/2011 | Carl et al. |
| 8,026,729 B2 | 9/2011 | Kroh et al. |
| 8,029,477 B2 | 10/2011 | Byrum et al. |
| 8,029,567 B2 | 10/2011 | Edidin et al. |
| 8,034,080 B2 | 10/2011 | Malandain et al. |
| 8,037,871 B2 | 10/2011 | McClendon |
| 8,038,680 B2 | 10/2011 | Ainsworth et al. |
| 8,038,698 B2 | 10/2011 | Edidin et al. |
| 8,043,206 B2 | 10/2011 | Birk |
| 8,043,290 B2 | 10/2011 | Harrison et al. |
| 8,043,299 B2 | 10/2011 | Conway |
| 8,043,338 B2 | 10/2011 | Dant |
| 8,043,345 B2 | 10/2011 | Carl et al. |
| 8,048,169 B2 | 11/2011 | Burnett et al. |
| 8,057,473 B2 | 11/2011 | Orsak et al. |
| 8,057,513 B2 | 11/2011 | Kohm et al. |
| 8,066,650 B2 | 11/2011 | Lee et al. |
| 8,070,670 B2 | 12/2011 | Deem et al. |
| 8,070,671 B2 | 12/2011 | Deem et al. |
| 8,070,695 B2 | 12/2011 | Gupta et al. |
| 8,070,813 B2 | 12/2011 | Grotz et al. |
| 8,074,654 B2 | 12/2011 | Paraschac et al. |
| 8,075,577 B2 | 12/2011 | Deem et al. |
| 8,079,974 B2 | 12/2011 | Stergiopulos |
| 8,079,989 B2 | 12/2011 | Birk et al. |
| 8,080,022 B2 | 12/2011 | Deem et al. |
| 8,080,025 B2 | 12/2011 | Deem et al. |
| 8,088,166 B2 | 1/2012 | Makower et al. |
| 8,092,459 B2 | 1/2012 | Malandain |
| 8,092,499 B1 | 1/2012 | Roth |
| 8,095,317 B2 | 1/2012 | Ekseth et al. |
| 8,096,302 B2 | 1/2012 | Nelson et al. |
| 8,096,938 B2 | 1/2012 | Forsell |
| 8,096,995 B2 | 1/2012 | Kohm et al. |
| 8,097,018 B2 | 1/2012 | Malandain et al. |
| 8,097,038 B2 | 1/2012 | Malek |
| 8,100,819 B2 | 1/2012 | Banik |
| 8,100,943 B2 | 1/2012 | Malandain et al. |
| 8,100,967 B2 | 1/2012 | Makower et al. |
| 8,105,360 B1 | 1/2012 | Connor |

(56) References Cited

U.S. PATENT DOCUMENTS

| | | |
|---|---|---|
| 8,105,363 B2 | 1/2012 | Fielding et al. |
| 8,105,364 B2 | 1/2012 | McCarthy et al. |
| 8,109,974 B2 | 2/2012 | Boomer et al. |
| 8,114,158 B2 | 2/2012 | Carl et al. |
| 8,123,765 B2 | 2/2012 | Deem et al. |
| 8,123,805 B2 | 2/2012 | Makower et al. |
| 8,128,628 B2 | 3/2012 | Freid et al. |
| 8,133,280 B2 | 3/2012 | Voellmicke et al. |
| 8,137,349 B2 | 3/2012 | Soubeiran |
| 8,137,366 B2 | 3/2012 | Deem et al. |
| 8,137,367 B2 | 3/2012 | Deem et al. |
| 8,142,454 B2 | 3/2012 | Harrison et al. |
| 8,142,494 B2 | 3/2012 | Rahdert et al. |
| 8,147,517 B2 | 4/2012 | Trieu et al. |
| 8,147,549 B2 | 4/2012 | Metcalf, Jr. et al. |
| 8,157,841 B2 | 4/2012 | Malandain et al. |
| 8,162,897 B2 | 4/2012 | Byrum |
| 8,162,979 B2 | 4/2012 | Sachs et al. |
| 8,163,013 B2 | 4/2012 | Machold et al. |
| 8,177,789 B2 | 5/2012 | Magill et al. |
| 8,182,411 B2 | 5/2012 | Dlugos |
| 8,187,324 B2 | 5/2012 | Webler et al. |
| 8,197,544 B1 | 6/2012 | Manzi et al. |
| 8,202,305 B2 | 6/2012 | Reiley |
| 8,211,127 B2 | 7/2012 | Uth et al. |
| 8,211,149 B2 | 7/2012 | Justis |
| 8,211,151 B2 | 7/2012 | Schwab et al. |
| 8,211,179 B2 | 7/2012 | Molz, IV et al. |
| 8,216,275 B2 | 7/2012 | Fielding et al. |
| 8,221,420 B2 | 7/2012 | Keller |
| 8,226,690 B2 | 7/2012 | Altarac et al. |
| 8,236,002 B2 | 8/2012 | Fortin et al. |
| 8,241,292 B2 | 8/2012 | Collazo |
| 8,241,293 B2 | 8/2012 | Stone et al. |
| 8,241,331 B2 | 8/2012 | Arnin |
| 8,246,630 B2 | 8/2012 | Manzi et al. |
| 8,251,888 B2 | 8/2012 | Roslin et al. |
| 8,252,063 B2 | 8/2012 | Stauch |
| 8,257,370 B2 | 9/2012 | Moskowitz et al. |
| 8,257,442 B2 | 9/2012 | Edie et al. |
| 8,263,024 B2 | 9/2012 | Wan et al. |
| 8,267,969 B2 | 9/2012 | Altarac et al. |
| 8,273,112 B2 | 9/2012 | Garamszegi et al. |
| 8,278,941 B2 | 10/2012 | Kroh et al. |
| 8,282,671 B2 | 10/2012 | Connor |
| 8,287,540 B2 | 10/2012 | LeCronier et al. |
| 8,298,133 B2 | 10/2012 | Wiley et al. |
| 8,298,240 B2 | 10/2012 | Giger et al. |
| 8,308,779 B2 | 11/2012 | Reiley |
| 8,313,423 B2 | 11/2012 | Forsell |
| 8,316,856 B2 | 11/2012 | Nelson et al. |
| 8,317,761 B2 | 11/2012 | Birk et al. |
| 8,317,802 B1 | 11/2012 | Manzi et al. |
| 8,323,290 B2 | 12/2012 | Metzger et al. |
| 8,326,435 B2 | 12/2012 | Stevenson |
| 8,328,807 B2 | 12/2012 | Brigido |
| 8,328,854 B2 | 12/2012 | Baynham et al. |
| 8,333,204 B2 | 12/2012 | Saadat |
| 8,333,790 B2 | 12/2012 | Timm et al. |
| 8,353,913 B2 | 1/2013 | Moskowitz et al. |
| 8,357,169 B2 | 1/2013 | Henniges et al. |
| 8,357,182 B2 | 1/2013 | Seme |
| 8,357,183 B2 | 1/2013 | Seme et al. |
| 8,360,955 B2 | 1/2013 | Sayet et al. |
| 8,366,628 B2 | 2/2013 | Denker et al. |
| 8,372,078 B2 | 2/2013 | Collazo |
| 8,382,652 B2 | 2/2013 | Sayet et al. |
| 8,382,756 B2 | 2/2013 | Pool et al. |
| 8,386,018 B2 | 2/2013 | Stauch et al. |
| 8,388,667 B2 | 3/2013 | Reiley et al. |
| 8,394,124 B2 | 3/2013 | Biyani |
| 8,394,143 B2 | 3/2013 | Grotz et al. |
| 8,403,958 B2 | 3/2013 | Schwab |
| 8,409,203 B2 | 4/2013 | Birk et al. |
| 8,409,281 B2 | 4/2013 | Makower et al. |
| 8,414,584 B2 | 4/2013 | Brigido |
| 8,414,648 B2 | 4/2013 | Reiley |
| 8,419,755 B2 | 4/2013 | Deem et al. |
| 8,419,801 B2 | 4/2013 | DiSilvestro et al. |
| 8,425,570 B2 | 4/2013 | Reiley |
| 8,425,608 B2 | 4/2013 | Dewey et al. |
| 8,433,519 B2 | 4/2013 | Ekseth et al. |
| 8,435,268 B2 | 5/2013 | Thompson et al. |
| 8,439,915 B2 | 5/2013 | Harrison et al. |
| 8,439,926 B2 | 5/2013 | Bojarski et al. |
| 8,444,693 B2 | 5/2013 | Reiley |
| 8,449,553 B2 | 5/2013 | Kam et al. |
| 8,449,580 B2 | 5/2013 | Voellmicke et al. |
| 8,454,695 B2 | 6/2013 | Grotz et al. |
| 8,469,908 B2 | 6/2013 | Asfora |
| 8,469,978 B2 | 6/2013 | Fobi et al. |
| 8,470,003 B2 | 6/2013 | Voellmicke et al. |
| 8,470,004 B2 | 6/2013 | Reiley |
| 8,475,354 B2 | 7/2013 | Phillips et al. |
| 8,475,356 B2 | 7/2013 | Feng et al. |
| 8,475,499 B2 | 7/2013 | Cournoyer et al. |
| 8,480,554 B2 | 7/2013 | Phillips et al. |
| 8,480,668 B2 | 7/2013 | Fernandez et al. |
| 8,480,741 B2 | 7/2013 | Grotz et al. |
| 8,486,070 B2 | 7/2013 | Morgan et al. |
| 8,486,076 B2 | 7/2013 | Chavarria et al. |
| 8,486,110 B2 | 7/2013 | Fielding et al. |
| 8,486,113 B2 | 7/2013 | Malek |
| 8,486,147 B2 | 7/2013 | de Villiers et al. |
| 8,491,589 B2 | 7/2013 | Fisher et al. |
| 8,494,805 B2 | 7/2013 | Roche et al. |
| 8,496,662 B2 | 7/2013 | Novak et al. |
| 8,500,810 B2 | 8/2013 | Mastrorio et al. |
| 8,506,517 B2 | 8/2013 | Stergiopulos |
| 8,506,569 B2 | 8/2013 | Keefer et al. |
| 8,517,973 B2 | 8/2013 | Burnett |
| 8,518,062 B2 | 8/2013 | Cole et al. |
| 8,518,086 B2 | 8/2013 | Seme et al. |
| 8,522,790 B2 | 9/2013 | Nelson et al. |
| 8,523,865 B2 | 9/2013 | Reglos et al. |
| 8,523,866 B2 | 9/2013 | Sidebotham et al. |
| 8,523,883 B2 | 9/2013 | Saadat |
| 8,529,474 B2 | 9/2013 | Gupta et al. |
| 8,529,606 B2 | 9/2013 | Alamin et al. |
| 8,529,607 B2 | 9/2013 | Alamin et al. |
| 8,529,630 B2 | 9/2013 | Bojarski et al. |
| 8,545,384 B2 | 10/2013 | Forsell |
| 8,545,508 B2 | 10/2013 | Collazo |
| 8,545,814 B2 | 10/2013 | Contag et al. |
| 8,551,092 B2 | 10/2013 | Morgan et al. |
| 8,551,142 B2 | 10/2013 | Altarac et al. |
| 8,551,422 B2 | 10/2013 | Wan et al. |
| 8,556,901 B2 | 10/2013 | Anthony et al. |
| 8,556,911 B2 | 10/2013 | Mehta et al. |
| 8,556,975 B2 | 10/2013 | Ciupik et al. |
| 8,562,653 B2 | 10/2013 | Alamin et al. |
| 8,568,416 B2 | 10/2013 | Schmitz et al. |
| 8,568,457 B2 | 10/2013 | Hunziker |
| 8,574,267 B2 | 11/2013 | Linares |
| 8,579,919 B2 | 11/2013 | Bolduc et al. |
| 8,579,979 B2 | 11/2013 | Edie et al. |
| 8,585,595 B2 | 11/2013 | Heilman |
| 8,585,702 B2 | 11/2013 | Orsak et al. |
| 8,585,738 B2 | 11/2013 | Linares |
| 8,585,740 B1 | 11/2013 | Ross et al. |
| 8,591,549 B2 | 11/2013 | Lange |
| 8,597,362 B2 | 12/2013 | Shenoy et al. |
| 8,613,749 B2 | 12/2013 | Deem et al. |
| 8,613,758 B2 | 12/2013 | Linares |
| 8,617,212 B2 | 12/2013 | Linares |
| 8,617,220 B2 | 12/2013 | Skaggs |
| 8,617,243 B2 | 12/2013 | Eisermann et al. |
| 8,622,936 B2 | 1/2014 | Schenberger et al. |
| 8,623,036 B2 | 1/2014 | Harrison et al. |
| 8,623,042 B2 | 1/2014 | Roslin et al. |
| 8,623,056 B2 | 1/2014 | Linares |
| 8,632,544 B2 | 1/2014 | Haaja et al. |
| 8,632,547 B2 | 1/2014 | Maxson et al. |
| 8,632,548 B2 | 1/2014 | Soubeiran |

(56) References Cited

U.S. PATENT DOCUMENTS

| | | |
|---|---|---|
| 8,632,563 B2 | 1/2014 | Nagase et al. |
| 8,632,594 B2 | 1/2014 | Williams et al. |
| 8,636,770 B2 | 1/2014 | Hestad et al. |
| 8,636,771 B2 | 1/2014 | Butler et al. |
| 8,636,802 B2 | 1/2014 | Serhan et al. |
| 8,641,719 B2 | 2/2014 | Gephart et al. |
| 8,641,723 B2 | 2/2014 | Connor |
| 8,652,175 B2 | 2/2014 | Timm et al. |
| 8,657,765 B2 | 2/2014 | Asfora |
| 8,657,856 B2 | 2/2014 | Gephart et al. |
| 8,657,885 B2 | 2/2014 | Burnett et al. |
| 8,663,139 B2 | 3/2014 | Asfora |
| 8,663,140 B2 | 3/2014 | Asfora |
| 8,663,285 B2 | 3/2014 | Dall et al. |
| 8,663,287 B2 | 3/2014 | Butler et al. |
| 8,663,338 B2 | 3/2014 | Burnett et al. |
| 8,668,719 B2 | 3/2014 | Alamin et al. |
| 8,673,001 B2 | 3/2014 | Cartledge et al. |
| 8,679,161 B2 | 3/2014 | Malandain et al. |
| 8,690,858 B2 | 4/2014 | Machold et al. |
| 8,707,959 B2 | 4/2014 | Paraschac et al. |
| 8,709,090 B2 | 4/2014 | Makower et al. |
| 8,715,243 B2 | 5/2014 | Uth et al. |
| 8,715,290 B2 | 5/2014 | Fisher et al. |
| 8,721,570 B2 | 5/2014 | Gupta et al. |
| 8,721,643 B2 | 5/2014 | Morgan et al. |
| 8,728,125 B2 | 5/2014 | Bruneau et al. |
| 8,734,318 B2 | 5/2014 | Forsell |
| 8,734,516 B2 | 5/2014 | Moskowitz et al. |
| 8,734,519 B2 | 5/2014 | de Villiers et al. |
| 8,747,444 B2 | 6/2014 | Moskowitz et al. |
| 8,752,552 B2 | 6/2014 | Nelson et al. |
| 8,758,303 B2 | 6/2014 | Uth et al. |
| 8,758,347 B2 | 6/2014 | Weiner et al. |
| 8,758,355 B2 | 6/2014 | Fisher et al. |
| 8,758,372 B2 | 6/2014 | Cartledge et al. |
| 8,762,308 B2 | 6/2014 | Najarian et al. |
| 8,764,713 B2 | 7/2014 | Uth et al. |
| 8,771,272 B2 | 7/2014 | LeCronier et al. |
| 8,777,947 B2 | 7/2014 | Zahrly et al. |
| 8,777,995 B2 | 7/2014 | McClintock et al. |
| 8,781,744 B2 | 7/2014 | Ekseth et al. |
| 8,784,482 B2 | 7/2014 | Rahdert et al. |
| 8,790,343 B2 | 7/2014 | McClellan et al. |
| 8,790,380 B2 | 7/2014 | Buttermann |
| 8,790,409 B2 | 7/2014 | Van den Heuvel et al. |
| 8,794,243 B2 | 8/2014 | Deem et al. |
| 8,795,339 B2 | 8/2014 | Boomer et al. |
| 8,801,795 B2 | 8/2014 | Makower et al. |
| 8,808,206 B2 | 8/2014 | Asfora |
| 8,813,727 B2 | 8/2014 | McClendon |
| 8,814,869 B2 | 8/2014 | Freid et al. |
| 8,828,058 B2 | 9/2014 | Elsebaie et al. |
| 8,828,087 B2 | 9/2014 | Stone et al. |
| 8,840,623 B2 | 9/2014 | Reiley |
| 8,840,651 B2 | 9/2014 | Reiley |
| 8,845,692 B2 | 9/2014 | Wisnewski |
| 8,845,724 B2 | 9/2014 | Shenoy et al. |
| 8,864,717 B2 | 10/2014 | Conlon et al. |
| 8,864,823 B2 | 10/2014 | Cartledge et al. |
| 8,870,881 B2 | 10/2014 | Rezach et al. |
| 8,870,918 B2 | 10/2014 | Boomer et al. |
| 8,870,959 B2 | 10/2014 | Arnin |
| 8,882,699 B2 | 11/2014 | Burnett |
| 8,882,830 B2 | 11/2014 | Cartledge et al. |
| 8,888,672 B2 | 11/2014 | Phillips et al. |
| 8,888,673 B2 | 11/2014 | Phillips et al. |
| 8,894,663 B2 | 11/2014 | Giger et al. |
| 8,915,915 B2 | 12/2014 | Harrison et al. |
| 8,915,917 B2 | 12/2014 | Doherty et al. |
| 8,920,422 B2 | 12/2014 | Homeier et al. |
| 8,932,247 B2 | 1/2015 | Stergiopulos |
| 8,945,188 B2 | 2/2015 | Rezach et al. |
| 8,945,210 B2 | 2/2015 | Cartledge et al. |
| 8,956,407 B2 | 2/2015 | Macoviak et al. |
| 8,961,386 B2 | 2/2015 | Phillips et al. |
| 8,961,521 B2 | 2/2015 | Keefer et al. |
| 8,961,567 B2 | 2/2015 | Hunziker |
| 8,968,402 B2 | 3/2015 | Myers et al. |
| 8,968,406 B2 | 3/2015 | Arnin |
| 8,986,348 B2 | 3/2015 | Reiley |
| 8,992,527 B2 | 3/2015 | Guichet |
| 9,005,251 B2 | 4/2015 | Heggeness |
| 9,005,293 B2 | 4/2015 | Moskowitz et al. |
| 9,005,298 B2 | 4/2015 | Makower et al. |
| 9,011,491 B2 | 4/2015 | Carl et al. |
| 9,015,057 B2 | 4/2015 | Phillips et al. |
| 9,022,917 B2 | 5/2015 | Kasic et al. |
| 9,028,550 B2 | 5/2015 | Shulock et al. |
| 9,033,957 B2 | 5/2015 | Cadeddu et al. |
| 9,033,988 B2 | 5/2015 | Gephart et al. |
| 9,034,016 B2 | 5/2015 | Panjabi |
| 9,044,218 B2 | 6/2015 | Young |
| 9,060,810 B2 | 6/2015 | Kercher et al. |
| 9,060,844 B2 | 6/2015 | Kagan et al. |
| 9,072,530 B2 | 7/2015 | Mehta et al. |
| 9,072,606 B2 | 7/2015 | Lucas et al. |
| 9,078,703 B2 | 7/2015 | Arnin |
| 9,084,632 B2 | 7/2015 | Orsak et al. |
| 9,089,348 B2 | 7/2015 | Chavarria et al. |
| 9,095,436 B2 | 8/2015 | Boyden et al. |
| 9,095,437 B2 | 8/2015 | Boyden et al. |
| 9,101,422 B2 | 8/2015 | Freid et al. |
| 9,101,427 B2 | 8/2015 | Globerman et al. |
| 9,107,706 B2 | 8/2015 | Alamin et al. |
| 9,113,967 B2 | 8/2015 | Soubeiran |
| 9,114,016 B2 | 8/2015 | Shenoy et al. |
| 9,125,746 B2 | 9/2015 | Clifford et al. |
| 9,138,266 B2 | 9/2015 | Stauch |
| 9,144,482 B2 | 9/2015 | Sayet |
| 9,155,565 B2 | 10/2015 | Boomer et al. |
| 9,161,856 B2 | 10/2015 | Nelson et al. |
| 9,168,071 B2 | 10/2015 | Seme et al. |
| 9,168,076 B2 | 10/2015 | Patty et al. |
| 9,173,681 B2 | 11/2015 | Seme |
| 9,173,715 B2 | 11/2015 | Baumgartner |
| 9,186,158 B2 | 11/2015 | Anthony et al. |
| 9,186,185 B2 | 11/2015 | Hestad et al. |
| 9,198,771 B2 | 12/2015 | Ciupik |
| 9,204,899 B2 | 12/2015 | Buttermann |
| 9,204,908 B2 | 12/2015 | Buttermann |
| 9,220,536 B2 | 12/2015 | Skaggs |
| 9,226,783 B2 | 1/2016 | Brigido |
| 9,242,070 B2 | 1/2016 | Tieu |
| 9,259,243 B2 | 2/2016 | Giger et al. |
| 9,272,159 B2 | 3/2016 | Phillips et al. |
| 9,278,004 B2 | 3/2016 | Shenoy et al. |
| 9,278,046 B2 | 3/2016 | Asfora |
| 9,282,997 B2 | 3/2016 | Hunziker |
| 9,301,792 B2 | 4/2016 | Henniges et al. |
| 9,301,854 B2 | 4/2016 | Moskowitz et al. |
| 9,308,089 B2 | 4/2016 | Vicatos et al. |
| 9,308,387 B2 | 4/2016 | Phillips et al. |
| 9,320,618 B2 | 4/2016 | Schmitz et al. |
| 9,326,728 B2 | 5/2016 | Demir et al. |
| 9,333,009 B2 | 5/2016 | Kroll et al. |
| 9,339,197 B2 | 5/2016 | Griswold et al. |
| 9,339,300 B2 | 5/2016 | Kantelhardt |
| 9,339,307 B2 | 5/2016 | McClintock et al. |
| 9,339,312 B2 | 5/2016 | Doherty et al. |
| 9,358,044 B2 | 6/2016 | Seme et al. |
| 9,364,267 B2 | 6/2016 | Northcutt et al. |
| 9,370,388 B2 | 6/2016 | Globerman et al. |
| 9,393,123 B2 | 7/2016 | Lucas et al. |
| 9,408,644 B2 | 8/2016 | Zahrly et al. |
| 9,421,347 B2 | 8/2016 | Burnett |
| 9,427,267 B2 | 8/2016 | Homeier et al. |
| 9,439,744 B2 | 9/2016 | Forsell |
| 9,439,797 B2 | 9/2016 | Baym et al. |
| 9,445,848 B2 | 9/2016 | Anderson et al. |
| 9,451,997 B2 | 9/2016 | Carl et al. |
| 9,456,953 B2 | 10/2016 | Asfora |
| 9,474,612 B2 | 10/2016 | Haaja et al. |
| 9,492,199 B2 | 11/2016 | Orsak et al. |

(56) References Cited

U.S. PATENT DOCUMENTS

| | | |
|---|---|---|
| 9,492,276 B2 | 11/2016 | Lee et al. |
| 9,498,258 B2 | 11/2016 | Boomer et al. |
| 9,498,366 B2 | 11/2016 | Burnett et al. |
| 9,510,834 B2 | 12/2016 | Burnett et al. |
| 9,532,804 B2 | 1/2017 | Clifford et al. |
| 9,561,062 B2 | 2/2017 | Hayes et al. |
| 9,561,063 B2 | 2/2017 | Reiley |
| 9,572,588 B2 | 2/2017 | Fisher et al. |
| 9,572,746 B2 | 2/2017 | Asfora |
| 9,572,910 B2 | 2/2017 | Messersmith et al. |
| 9,579,110 B2 | 2/2017 | Bojarski et al. |
| 9,579,203 B2 | 2/2017 | Soubeiran |
| 9,603,605 B2 | 3/2017 | Collazo |
| 9,603,713 B2 | 3/2017 | Moskowitz et al. |
| 9,610,161 B2 | 4/2017 | Macoviak et al. |
| 9,622,875 B2 | 4/2017 | Moskowitz et al. |
| 9,642,735 B2 | 5/2017 | Burnett |
| 9,655,651 B2 | 5/2017 | Panjabi |
| 9,668,868 B2 | 6/2017 | Shenoy et al. |
| 9,687,243 B2 | 6/2017 | Burnett et al. |
| 9,687,414 B2 | 6/2017 | Asfora |
| 9,693,813 B2 | 7/2017 | Walker et al. |
| 9,693,867 B2 | 7/2017 | Lucas et al. |
| 9,700,419 B2 | 7/2017 | Clifford et al. |
| 9,700,450 B2 | 7/2017 | Burnett |
| 9,717,537 B2 | 8/2017 | Gordon |
| 9,724,135 B2 | 8/2017 | Koch et al. |
| 9,724,265 B2 | 8/2017 | Asfora |
| 9,730,738 B2 | 8/2017 | Gephart et al. |
| 9,743,969 B2 | 8/2017 | Reiley |
| 9,782,206 B2 | 10/2017 | Mueckter et al. |
| 9,795,410 B2 | 10/2017 | Shenoy et al. |
| 9,814,600 B2 | 11/2017 | Shulock et al. |
| 9,820,789 B2 | 11/2017 | Reiley |
| 9,826,987 B2 | 11/2017 | Keefer et al. |
| 9,833,291 B2 | 12/2017 | Baumgartner |
| 9,848,894 B2 | 12/2017 | Burley et al. |
| 9,848,993 B2 | 12/2017 | Moskowitz et al. |
| 9,861,376 B2 | 1/2018 | Chavarria et al. |
| 9,861,390 B2 | 1/2018 | Hunziker |
| 9,861,404 B2 | 1/2018 | Reiley |
| 9,867,719 B2 | 1/2018 | Moskowitz et al. |
| 10,271,885 B2 * | 4/2019 | Quach .............. A61B 50/30 |
| 2001/0011543 A1 | 8/2001 | Forsell |
| 2002/0019580 A1 | 2/2002 | Lau et al. |
| 2002/0050112 A1 | 5/2002 | Koch et al. |
| 2002/0072758 A1 | 6/2002 | Reo et al. |
| 2002/0164905 A1 | 11/2002 | Bryant |
| 2003/0019498 A1 | 1/2003 | Forsell |
| 2003/0040671 A1 | 2/2003 | Somogyi et al. |
| 2003/0066536 A1 | 4/2003 | Forsell |
| 2003/0114731 A1 | 6/2003 | Cadeddu et al. |
| 2003/0187447 A1 | 10/2003 | Ferrante et al. |
| 2003/0208212 A1 | 11/2003 | Cigaina |
| 2003/0220643 A1 | 11/2003 | Ferree |
| 2003/0220644 A1 | 11/2003 | Thelen et al. |
| 2004/0006342 A1 | 1/2004 | Altarac et al. |
| 2004/0011137 A1 | 1/2004 | Hnat et al. |
| 2004/0011365 A1 | 1/2004 | Govari et al. |
| 2004/0019353 A1 | 1/2004 | Freid et al. |
| 2004/0023623 A1 | 2/2004 | Stauch et al. |
| 2004/0055610 A1 | 3/2004 | Forsell |
| 2004/0064030 A1 | 4/2004 | Forsell |
| 2004/0068205 A1 | 4/2004 | Zogbi et al. |
| 2004/0092939 A1 | 5/2004 | Freid et al. |
| 2004/0098121 A1 | 5/2004 | Opolski |
| 2004/0116773 A1 | 6/2004 | Furness et al. |
| 2004/0133219 A1 | 7/2004 | Forsell |
| 2004/0138725 A1 | 7/2004 | Forsell |
| 2004/0153106 A1 | 8/2004 | Dudai |
| 2004/0158254 A1 | 8/2004 | Eisermann |
| 2004/0172040 A1 | 9/2004 | Heggeness |
| 2004/0173222 A1 | 9/2004 | Kim |
| 2004/0193266 A1 | 9/2004 | Meyer |
| 2004/0220567 A1 | 11/2004 | Eisermann et al. |
| 2004/0220668 A1 | 11/2004 | Eisermann et al. |
| 2004/0230307 A1 | 11/2004 | Eisermann |
| 2004/0250820 A1 | 12/2004 | Forsell |
| 2004/0260287 A1 | 12/2004 | Ferree |
| 2004/0260319 A1 | 12/2004 | Egle |
| 2005/0002984 A1 | 1/2005 | Byrum et al. |
| 2005/0043802 A1 | 2/2005 | Eisermann et al. |
| 2005/0055025 A1 | 3/2005 | Zacouto et al. |
| 2005/0070937 A1 | 3/2005 | Jambor et al. |
| 2005/0080427 A1 | 4/2005 | Govari et al. |
| 2005/0080439 A1 | 4/2005 | Carson et al. |
| 2005/0090823 A1 | 4/2005 | Bartimus |
| 2005/0096750 A1 | 5/2005 | Kagan et al. |
| 2005/0131352 A1 | 6/2005 | Conlon et al. |
| 2005/0159754 A1 | 7/2005 | Odrich |
| 2005/0159755 A1 | 7/2005 | Odrich |
| 2005/0165440 A1 | 7/2005 | Cancel et al. |
| 2005/0171543 A1 | 8/2005 | Timm et al. |
| 2005/0177164 A1 | 8/2005 | Walters et al. |
| 2005/0182400 A1 | 8/2005 | White |
| 2005/0182401 A1 | 8/2005 | Timm et al. |
| 2005/0182412 A1 | 8/2005 | Johnson et al. |
| 2005/0192629 A1 | 9/2005 | Saadat et al. |
| 2005/0222489 A1 | 10/2005 | Rahdert et al. |
| 2005/0234289 A1 | 10/2005 | Anstadt et al. |
| 2005/0234448 A1 | 10/2005 | McCarthy |
| 2005/0234462 A1 | 10/2005 | Hershberger |
| 2005/0246034 A1 | 11/2005 | Soubeiran |
| 2005/0251109 A1 | 11/2005 | Soubeiran |
| 2005/0261779 A1 | 11/2005 | Meyer |
| 2005/0272976 A1 | 12/2005 | Tanaka et al. |
| 2005/0288672 A1 | 12/2005 | Ferree |
| 2006/0020278 A1 | 1/2006 | Burnett et al. |
| 2006/0036251 A1 | 2/2006 | Reiley |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0079897 A1 | 4/2006 | Harrison et al. |
| 2006/0116757 A1 | 6/2006 | Lashinski et al. |
| 2006/0124140 A1 | 6/2006 | Forsell |
| 2006/0136062 A1 | 6/2006 | DiNello et al. |
| 2006/0142634 A1 | 6/2006 | Anstadt et al. |
| 2006/0142767 A1 | 6/2006 | Green et al. |
| 2006/0155279 A1 | 7/2006 | Ogilvie |
| 2006/0155347 A1 | 7/2006 | Forsell |
| 2006/0184240 A1 | 8/2006 | Jimenez et al. |
| 2006/0184248 A1 | 8/2006 | Edidin et al. |
| 2006/0195102 A1 | 8/2006 | Malandain |
| 2006/0204156 A1 | 9/2006 | Takehara et al. |
| 2006/0211909 A1 | 9/2006 | Anstadt et al. |
| 2006/0235299 A1 | 10/2006 | Martinelli |
| 2006/0235424 A1 | 10/2006 | Vitale et al. |
| 2006/0241746 A1 | 10/2006 | Shaoulian et al. |
| 2006/0249914 A1 | 11/2006 | Dulin |
| 2006/0252983 A1 | 11/2006 | Lembo et al. |
| 2006/0271107 A1 | 11/2006 | Harrison et al. |
| 2006/0276812 A1 | 12/2006 | Hill et al. |
| 2006/0282073 A1 | 12/2006 | Simanovsky |
| 2006/0289014 A1 | 12/2006 | Purdy et al. |
| 2006/0293671 A1 | 12/2006 | Heggeness |
| 2006/0293683 A1 | 12/2006 | Stauch |
| 2007/0010814 A1 | 1/2007 | Stauch |
| 2007/0015955 A1 | 1/2007 | Tsonton |
| 2007/0021644 A1 | 1/2007 | Woolson et al. |
| 2007/0031131 A1 | 2/2007 | Griffitts |
| 2007/0043376 A1 | 2/2007 | Leatherbury et al. |
| 2007/0050030 A1 | 3/2007 | Kim |
| 2007/0055237 A1 | 3/2007 | Edidin et al. |
| 2007/0055368 A1 | 3/2007 | Rhee et al. |
| 2007/0118215 A1 | 5/2007 | Moaddeb |
| 2007/0135913 A1 | 6/2007 | Moaddeb et al. |
| 2007/0162032 A1 | 7/2007 | Johnson et al. |
| 2007/0173837 A1 | 7/2007 | Chan et al. |
| 2007/0173869 A1 | 7/2007 | Gannoe et al. |
| 2007/0179493 A1 | 8/2007 | Kim |
| 2007/0213751 A1 | 9/2007 | Scirica et al. |
| 2007/0239159 A1 | 10/2007 | Altarac et al. |
| 2007/0250084 A1 | 10/2007 | Sharkawy et al. |
| 2007/0255088 A1 | 11/2007 | Jacobson et al. |

(56) References Cited

U.S. PATENT DOCUMENTS

| | | |
|---|---|---|
| 2007/0256693 A1 | 11/2007 | Paraschac et al. |
| 2007/0260270 A1 | 11/2007 | Assell et al. |
| 2007/0264605 A1 | 11/2007 | Belfor et al. |
| 2007/0270631 A1 | 11/2007 | Nelson et al. |
| 2007/0276369 A1 | 11/2007 | Allard et al. |
| 2007/0276372 A1 | 11/2007 | Malandain et al. |
| 2007/0276373 A1 | 11/2007 | Malandain |
| 2007/0276493 A1 | 11/2007 | Malandain et al. |
| 2007/0288024 A1 | 12/2007 | Gollogly |
| 2007/0288183 A1 | 12/2007 | Bulkes et al. |
| 2008/0015577 A1 | 1/2008 | Loeb |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0033431 A1 | 2/2008 | Jung et al. |
| 2008/0051784 A1 | 2/2008 | Gollogly |
| 2008/0051895 A1 | 2/2008 | Malandain et al. |
| 2008/0058936 A1 | 3/2008 | Malandain et al. |
| 2008/0058937 A1 | 3/2008 | Malandain et al. |
| 2008/0065077 A1 | 3/2008 | Ferree |
| 2008/0065215 A1 | 3/2008 | Reiley |
| 2008/0066764 A1 | 3/2008 | Paraschac et al. |
| 2008/0071275 A1 | 3/2008 | Ferree |
| 2008/0071276 A1 | 3/2008 | Ferree |
| 2008/0082118 A1 | 4/2008 | Edidin et al. |
| 2008/0082167 A1 | 4/2008 | Edidin et al. |
| 2008/0083413 A1 | 4/2008 | Forsell |
| 2008/0086128 A1 | 4/2008 | Lewis |
| 2008/0091059 A1 | 4/2008 | Machold et al. |
| 2008/0097523 A1 | 4/2008 | Bolduc et al. |
| 2008/0108995 A1 | 5/2008 | Conway et al. |
| 2008/0140188 A1 | 6/2008 | Rahdert et al. |
| 2008/0147139 A1 | 6/2008 | Barrett et al. |
| 2008/0147192 A1 | 6/2008 | Edidin et al. |
| 2008/0161933 A1 | 7/2008 | Grotz et al. |
| 2008/0167685 A1 | 7/2008 | Allard et al. |
| 2008/0172063 A1 | 7/2008 | Taylor |
| 2008/0177319 A1 | 7/2008 | Schwab |
| 2008/0177326 A1 | 7/2008 | Thompson |
| 2008/0195156 A1 | 8/2008 | Ainsworth et al. |
| 2008/0226563 A1 | 9/2008 | Contag et al. |
| 2008/0228186 A1 | 9/2008 | Gall et al. |
| 2008/0255615 A1 | 10/2008 | Vittur et al. |
| 2008/0272928 A1 | 11/2008 | Shuster |
| 2008/0275552 A1 | 11/2008 | Makower et al. |
| 2008/0275555 A1 | 11/2008 | Makower et al. |
| 2008/0275557 A1 | 11/2008 | Makower et al. |
| 2008/0275567 A1 | 11/2008 | Makower et al. |
| 2008/0293995 A1 | 11/2008 | Moaddeb et al. |
| 2009/0076597 A1 | 3/2009 | Dahlgren et al. |
| 2009/0082815 A1 | 3/2009 | Zylber et al. |
| 2009/0088803 A1 | 4/2009 | Justis et al. |
| 2009/0093820 A1 | 4/2009 | Trieu et al. |
| 2009/0093890 A1 | 4/2009 | Gelbart |
| 2009/0118699 A1 | 5/2009 | Utley et al. |
| 2009/0171356 A1 | 7/2009 | Klett |
| 2009/0177203 A1 | 7/2009 | Reiley |
| 2009/0182356 A1 | 7/2009 | Coe |
| 2009/0192514 A1 | 7/2009 | Feinberg et al. |
| 2009/0198144 A1 | 8/2009 | Phillips et al. |
| 2009/0204055 A1 | 8/2009 | Lennox et al. |
| 2009/0216113 A1 | 8/2009 | Meier et al. |
| 2009/0216262 A1 | 8/2009 | Burnett et al. |
| 2009/0240173 A1 | 9/2009 | Hsia et al. |
| 2009/0259236 A2 | 10/2009 | Burnett et al. |
| 2009/0270871 A1 | 10/2009 | Liu et al. |
| 2009/0275984 A1 | 11/2009 | Kim et al. |
| 2009/0318919 A1 | 12/2009 | Robinson |
| 2010/0004654 A1 | 1/2010 | Schmitz et al. |
| 2010/0030281 A1 | 2/2010 | Gollogly |
| 2010/0057127 A1 | 3/2010 | McGuire et al. |
| 2010/0081868 A1 | 4/2010 | Moaddeb et al. |
| 2010/0094304 A1 | 4/2010 | Pool |
| 2010/0100185 A1 | 4/2010 | Trieu et al. |
| 2010/0106192 A1 | 4/2010 | Barry |
| 2010/0106193 A1 | 4/2010 | Barry |
| 2010/0114103 A1 | 5/2010 | Harrison et al. |
| 2010/0121457 A1 | 5/2010 | Clifford et al. |
| 2010/0130941 A1 | 5/2010 | Conlon et al. |
| 2010/0137872 A1 | 6/2010 | Kam et al. |
| 2010/0145449 A1 | 6/2010 | Makower et al. |
| 2010/0145462 A1 | 6/2010 | Ainsworth et al. |
| 2010/0168751 A1 | 7/2010 | Anderson et al. |
| 2010/0179601 A1 | 7/2010 | Jung et al. |
| 2010/0198261 A1 | 8/2010 | Trieu et al. |
| 2010/0228167 A1 | 9/2010 | Ilovich et al. |
| 2010/0241168 A1 | 9/2010 | Franck et al. |
| 2010/0249782 A1 | 9/2010 | Durham |
| 2010/0249839 A1 | 9/2010 | Alamin et al. |
| 2010/0249847 A1 | 9/2010 | Jung et al. |
| 2010/0256626 A1 | 10/2010 | Muller et al. |
| 2010/0274290 A1 | 10/2010 | Jung et al. |
| 2010/0286730 A1 | 11/2010 | Gordon |
| 2010/0286791 A1 | 11/2010 | Goldsmith |
| 2010/0318129 A1 | 12/2010 | Seme et al. |
| 2010/0324684 A1 | 12/2010 | Eisermann et al. |
| 2010/0331883 A1 | 12/2010 | Schmitz et al. |
| 2011/0004076 A1 | 1/2011 | Janna et al. |
| 2011/0057756 A1 | 3/2011 | Marinescu et al. |
| 2011/0060422 A1 | 3/2011 | Makower et al. |
| 2011/0098748 A1 | 4/2011 | Jangra |
| 2011/0130702 A1 | 6/2011 | Stergiopulos |
| 2011/0184505 A1 | 7/2011 | Sharkawy et al. |
| 2011/0196371 A1 | 8/2011 | Forsell |
| 2011/0196435 A1 | 8/2011 | Forsell |
| 2011/0202138 A1 | 8/2011 | Shenoy et al. |
| 2011/0257655 A1 | 10/2011 | Copf, Jr. |
| 2011/0275879 A1 | 11/2011 | Nelson et al. |
| 2011/0284014 A1 | 11/2011 | Cadeddu et al. |
| 2012/0019341 A1 | 1/2012 | Gabay et al. |
| 2012/0019342 A1 | 1/2012 | Gabay et al. |
| 2012/0053633 A1 | 3/2012 | Stauch |
| 2012/0088953 A1 | 4/2012 | King |
| 2012/0089186 A1 | 4/2012 | Carl et al. |
| 2012/0089191 A1 | 4/2012 | Altarac et al. |
| 2012/0109207 A1 | 5/2012 | Trieu |
| 2012/0116522 A1 | 5/2012 | Makower et al. |
| 2012/0116535 A1 | 5/2012 | Ratron et al. |
| 2012/0130426 A1 | 5/2012 | Thompson |
| 2012/0136449 A1 | 5/2012 | Makower et al. |
| 2012/0172883 A1 | 7/2012 | Sayago |
| 2012/0179273 A1 | 7/2012 | Clifford et al. |
| 2012/0185040 A1 | 7/2012 | Rahdert et al. |
| 2012/0209265 A1 | 8/2012 | Pool |
| 2012/0221101 A1 | 8/2012 | Moaddeb et al. |
| 2012/0271353 A1 | 10/2012 | Barry |
| 2012/0277747 A1 | 11/2012 | Keller |
| 2012/0296234 A1 | 11/2012 | Wilhelm et al. |
| 2012/0312307 A1 | 12/2012 | Paraschac et al. |
| 2013/0013066 A1 | 1/2013 | Landry et al. |
| 2013/0018468 A1 | 1/2013 | Moskowitz et al. |
| 2013/0018469 A1 | 1/2013 | Moskowitz et al. |
| 2013/0023991 A1 | 1/2013 | Moskowitz et al. |
| 2013/0079830 A1 | 3/2013 | Garamszegi et al. |
| 2013/0138017 A1 | 5/2013 | Jundt et al. |
| 2013/0138154 A1 | 5/2013 | Reiley |
| 2013/0150889 A1 | 6/2013 | Fening et al. |
| 2013/0178903 A1 | 7/2013 | Abdou |
| 2013/0197639 A1 | 8/2013 | Clifford et al. |
| 2013/0204266 A1 | 8/2013 | Heilman |
| 2013/0204376 A1 | 8/2013 | DiSilvestro et al. |
| 2013/0238094 A1 | 9/2013 | Voellmicke et al. |
| 2013/0253587 A1 | 9/2013 | Carls et al. |
| 2013/0261623 A1 | 10/2013 | Voellmicke et al. |
| 2013/0261672 A1 | 10/2013 | Horvath |
| 2013/0296863 A1 | 11/2013 | Globerman et al. |
| 2013/0304021 A1 | 11/2013 | Cabiri et al. |
| 2013/0325006 A1 | 12/2013 | Michelinie et al. |
| 2013/0325071 A1 | 12/2013 | Niemiec et al. |
| 2013/0331889 A1 | 12/2013 | Alamin et al. |
| 2013/0345802 A1 | 12/2013 | Cartledge et al. |
| 2014/0018913 A1 | 1/2014 | Cartledge et al. |
| 2014/0031826 A1 | 1/2014 | Bojarski et al. |
| 2014/0031870 A1 | 1/2014 | Chang et al. |

(56) References Cited

U.S. PATENT DOCUMENTS

| | | |
|---|---|---|
| 2014/0031929 A1 | 1/2014 | Cartledge et al. |
| 2014/0039558 A1 | 2/2014 | Alamin et al. |
| 2014/0051914 A1 | 2/2014 | Fobi et al. |
| 2014/0052134 A1 | 2/2014 | Orisek |
| 2014/0058392 A1 | 2/2014 | Mueckter et al. |
| 2014/0058450 A1 | 2/2014 | Arlet |
| 2014/0067075 A1 | 3/2014 | Makower et al. |
| 2014/0080203 A1 | 3/2014 | Wan et al. |
| 2014/0107704 A1 | 4/2014 | Serhan et al. |
| 2014/0135838 A1 | 5/2014 | Alamin et al. |
| 2014/0142698 A1 | 5/2014 | Landry et al. |
| 2014/0155946 A1 | 6/2014 | Skinlo et al. |
| 2014/0163664 A1 | 6/2014 | Goldsmith |
| 2014/0172097 A1 | 6/2014 | Clifford et al. |
| 2014/0194932 A1 | 7/2014 | Bruneau et al. |
| 2014/0222138 A1 | 8/2014 | Machold et al. |
| 2014/0250674 A1 | 9/2014 | Pool et al. |
| 2014/0296918 A1 | 10/2014 | Fening et al. |
| 2014/0303539 A1 | 10/2014 | Baym et al. |
| 2014/0303540 A1 | 10/2014 | Baym et al. |
| 2014/0324047 A1* | 10/2014 | Zahrly .............. A61B 17/7216 606/63 |
| 2014/0336756 A1 | 11/2014 | Lee et al. |
| 2014/0350602 A1* | 11/2014 | Seme ................ A61B 17/7041 606/250 |
| 2014/0358150 A1 | 12/2014 | Kaufman et al. |
| 2015/0013687 A1 | 1/2015 | Paraschac et al. |
| 2015/0057490 A1 | 2/2015 | Forsell |
| 2015/0073565 A1 | 3/2015 | Nelson et al. |
| 2015/0105782 A1 | 4/2015 | D'Lima et al. |
| 2015/0105824 A1 | 4/2015 | Moskowitz et al. |
| 2015/0132174 A1 | 5/2015 | Marinescu et al. |
| 2015/0134007 A1 | 5/2015 | Alamin et al. |
| 2015/0142110 A1 | 5/2015 | Myers et al. |
| 2015/0150561 A1 | 6/2015 | Burnett et al. |
| 2015/0272600 A1 | 10/2015 | Mehta et al. |
| 2015/0313649 A1 | 11/2015 | Alamin et al. |

FOREIGN PATENT DOCUMENTS

| | | |
|---|---|---|
| DE | 1541262 | 6/1969 |
| DE | 8515687 | 12/1985 |
| DE | 68515687.6 | 12/1985 |
| DE | 19626230 | 1/1998 |
| DE | 19751733 | 12/1998 |
| DE | 19745654 | 4/1999 |
| DE | 102005045070 | 4/2007 |
| DE | 102007053362 | 5/2009 |
| EP | 0663184 | 7/1995 |
| EP | 1547549 | 6/2005 |
| EP | 1745765 | 1/2007 |
| EP | 1905388 | 4/2008 |
| FR | 2802406 | 6/2001 |
| FR | 2823663 | 10/2002 |
| FR | 2827756 | 1/2003 |
| FR | 2892617 | 5/2007 |
| FR | 2900563 | 11/2007 |
| FR | 2901991 | 12/2007 |
| FR | 2916622 | 12/2008 |
| FR | 2961386 | 12/2011 |
| GB | 1174814 | 12/1969 |
| HU | 223454 | 4/2002 |
| JP | 05-104022 | 4/1993 |
| JP | 09-056736 | 3/1997 |
| JP | 2001-507608 | 6/2001 |
| JP | 2002500063 A | 1/2002 |
| JP | 2003-172372 | 6/2003 |
| JP | 2003-530195 | 10/2003 |
| JP | 2007-050339 | 3/2007 |
| JP | 2011502003 A | 1/2011 |
| JP | 1991000722 | 9/2014 |
| SU | 1197658 A1 | 12/1985 |
| WO | WO8604498 | 8/1986 |
| WO | WO8707134 | 12/1987 |
| WO | WO8906940 | 8/1989 |
| WO | WO9601597 | 1/1996 |
| WO | WO9808454 | 3/1998 |
| WO | WO9830163 | 7/1998 |
| WO | WO1998044858 | 10/1998 |
| WO | WO9850309 | 11/1998 |
| WO | WO9903348 | 1/1999 |
| WO | WO9923744 | 5/1999 |
| WO | WO9951160 | 10/1999 |
| WO | WO1999051160 | 10/1999 |
| WO | WO9963907 | 12/1999 |
| WO | WO0000108 | 1/2000 |
| WO | WO0072768 | 12/2000 |
| WO | WO0105463 | 1/2001 |
| WO | WO0112108 | 2/2001 |
| WO | WO0124742 | 4/2001 |
| WO | WO2001024697 | 4/2001 |
| WO | WO0141671 | 6/2001 |
| WO | WO0145485 | 6/2001 |
| WO | WO0145487 | 6/2001 |
| WO | WO0145597 | 6/2001 |
| WO | WO0158390 | 8/2001 |
| WO | WO0167973 | 9/2001 |
| WO | WO0178614 | 10/2001 |
| WO | WO0236975 | 5/2002 |
| WO | WO03059215 | 7/2003 |
| WO | WO2004014245 | 2/2004 |
| WO | WO2004019796 | 3/2004 |
| WO | WO2004021870 | 3/2004 |
| WO | WO2004043280 | 5/2004 |
| WO | WO2005023090 | 3/2005 |
| WO | WO2005072195 | 8/2005 |
| WO | WO2005072664 | 8/2005 |
| WO | WO2005105001 | 11/2005 |
| WO | WO2006019520 | 2/2006 |
| WO | WO2006019521 | 2/2006 |
| WO | WO2006089085 | 8/2006 |
| WO | WO2006090380 | 8/2006 |
| WO | WO2006090380 | 10/2006 |
| WO | WO2006103071 | 10/2006 |
| WO | WO2006103074 | 10/2006 |
| WO | WO2006105084 | 10/2006 |
| WO | WO2007013059 | 2/2007 |
| WO | WO2007015239 | 2/2007 |
| WO | WO2007025191 | 3/2007 |
| WO | WO2007048012 | 4/2007 |
| WO | WO2007081304 | 7/2007 |
| WO | WO2007118179 | 10/2007 |
| WO | WO2007140180 | 12/2007 |
| WO | WO2007149555 | 12/2007 |
| WO | WO20071144489 | 12/2007 |
| WO | WO2008003952 | 1/2008 |
| WO | WO2008013623 | 1/2008 |
| WO | WO2008015679 | 2/2008 |
| WO | WO2008040880 | 4/2008 |
| WO | WO2008140756 | 11/2008 |
| WO | WO2010017649 | 2/2010 |
| WO | WO2010050891 | 5/2010 |
| WO | WO2010056650 | 5/2010 |
| WO | WO2011018778 | 2/2011 |
| WO | WO2011116158 | 9/2011 |
| WO | WO2013119528 | 8/2013 |
| WO | WO2013181329 | 12/2013 |
| WO | WO2014040013 | 3/2014 |
| WO | WO2011041398 | 4/2015 |

OTHER PUBLICATIONS

Abe, Jun, Kensei Nagata, Mamoru Ariyoshi, and Akio Inoue. "Experimental external fixation combined with percutaneous discectomy in the management of scoliosis." Spine 24, No. 7 (1999): 646-653.

Amer, A. R. A. L., and Ashraf A. Khanfour. "Evaluation of treatment of late-onset tibia vara using gradual angulationtranslation high tibial osteotomy." Acta orthopaedica Belgica 76, No. 3 (2010): 360.

Angrisani, L., F. Favretti, F. Furbetta, S. Gennai, G. Segato, V. Borrelli, A. Sergio, T. Lafullarde, G. Vander Velpen, and M Lorenzo. "Lap-Band ((R)) Rapid Port (TM) System: Preliminary results in 21 patients." In Obesity Surgery, vol. 15, No. 7,pp. 936-936.

(56) References Cited

OTHER PUBLICATIONS

Baumgart, Rainer, Stefan Hinterwimmer, Michael Krammer, Oliver Muensterer, and Wolf Mutschler. "The bioexpandable prosthesis: a new perspective after resection of malignant bone tumors in children." Journal of pediatric hematology/oncology 27, No. 8 (2005): 452-455.

Baumgart, R., P. Thaller, S. Hinterwimmer, M. Krammer, T. Hierl, and W. Mutschler. "A fully implantable, programmable distraction nail (Fitbone)—new perspectives for corrective and reconstructive limb surgery." In Practice of Intramedullary Locked Nails, pp. 189-198. Springer Berlin Heidelberg, 2006.

Bodó, László, László Hangody, Balázs Borsitzky, György Béres, Gabriella Arató, Peter Nagy, and Gábor K. Ráthonyi. "Development of a tension-adjustable implant for anterior cruciate ligament reconstruction." Eklem Hast Cerrahisi 19, No. 1 (2008): 27-32.

Boudjemline, Younes, Emmanuelle Pineau, Caroline Bonnet, Alix Mollet, Sylvia Abadir, Damien Bonnet, Daniel Sidi, and Gabriella Agnoletti. "Off-label use of an adjustable gastric banding system for pulmonary artery banding." The Journal of thoracic and cardiovascular surgery 131, No. 5 (2006): 1130-1135.

Brochure-VEPTR II Technique Guide 4/08.

Brochure-VEPTR Patient Guide dated 2/05.

Brown, S. "Single Port Surgery and the Dundee Endocone." SAGES Annual Scientific Sessions, Poster Abstracts (2007): 323-324.

Buchowski, Jacob M., Rishi Bhatnagar, David L. Skaggs, and Paul D. Sponseller. "Temporary internal distraction as an aid to correction of severe scoliosis." The Journal of Bone & Joint Surgery 88, No. 9 (2006): 2035-2041.

Burghardt, R. D., J. E. Herzenberg, S. C. Specht, and D. Paley. "Mechanical failure of the Intramedullary Skeletal Kinetic Distractor in limb lengthening." Journal of Bone & Joint Surgery, British vol. 93, No. 5 (2011): 639-643.

Burke, John Gerard. "Design of a minimally invasive non fusion device for the surgical management of scoliosis in the skeletally immature." Studies in health technology and informatics 123 (2005): 378-384.

Carter, D. R., and W. E. Caler. "A cumulative damage model for bone fracture." Journal of Orthopaedic Research 3, No. 1 (1985): 84-90.

Chapman, Andrew E., George Kiroff, Philip Game, Bruce Foster, Paul O'Brien, John Ham, and Guy J. Maddern. "Laparoscopic adjustable gastric banding in the treatment of obesity: a systematic literature review." Surgery 135, No. 3 (2004): 326-351.

Cole, J. Dean, Daniel Justin, Tagus Kasparis, Derk DeVlught, and Carl Knobloch. "The intramedullary skeletal distractor (ISKD): first clinical results of a new intramedullary nail for lengthening of the femur and tibia." Injury 32 (2001): 129-139.

Cole, J., D. Paley, and M. Dahl. "Operative Technique. ISKD. Intramedullary Skeletal Kinetic Distractor. Tibial Surgical Technique." IS-0508 (A)-OPT-US © Orthofix Inc 28 (2005).

Dailey, Hannah L., Charles J. Daly, John G. Galbraith, Michael Cronin, and James A. Harty. "A novel intramedullary nail for micromotion stimulation of tibial fractures." Clinical Biomechanics 27, No. 2 (2012): 182-188.

Daniels, A. U., Patrick Gemperline, Allen R. Grahn, and Harold K. Dunn. "A new method for continuous intraoperative measurement of Harrington rod loading patterns." Annals of biomedical engineering 12, No. 3 (1984): 233-246.

De Giorgi, G., G. Stella, S. Becchetti, G. Martucci, and D. Miscioscia. "Cotrel-Dubousset instrumentation for the treatment of severe scoliosis." European Spine Journal 8, No. 1 (1999): 8-15.

Dorsey, W. O., Bruce S. Miller, Jared P. Tadje, and Cari R. Bryant. "The stability of three commercially available implants used in medial opening wedge high tibial osteotomy." The journal of knee surgery 19, No. 2 (2006): 95-98.

Edeland, H. G., G. Eriksson, and E. Dahlberg. "Instrumentation for distraction by limited surgery in scoliosis treatment." Journal of biomedical engineering 3, No. 2 (1981): 143-146.

Ember, T., and H. Noordeen. "Distraction forces required during growth rod lengthening." Journal of Bone & Joint Surgery, British vol. 88, No. SUPP II (2006): 229-229.

Fabry, Hans, Robrecht Van Hee, Leo Hendrickx, and Eric Totté. "A technique for prevention of port adjustable silicone gastric banding." Obesity surgery 12, No. 2 (2002): 285-288.

Fried, M., W. Lechner, and K. Kormanova. "In vivo measurements of different gastric band pressures towards the gastric wall at the stoma region." In Obesity Surgery, vol. 14, No. 7, pp. 914-914. 3100 Bayview Ave, Unit 4, Toronto, Ontario M2N 5L3, Canada: F D-Communications Inc, 2004.

Gao, Xiaochong, Derek Gordon, Dongping Zhang, Richard Browne, Cynthia Helms, Joseph Gillum, Samuel Weber et al. "CHD7 gene polymorphisms are associated with susceptibility to idiopathic scoliosis." The American Journal of Human Genetics 80, No. 5 (2007): 957-965.

Gebhart, M., M. Neel, A. Soubeiran, and J. Dubousset. "Early clinical experience with a custom made growing endoprosthesis in children with malignant bone tumors of the lower extremity actioned by an external permanent magnet: the Phenix M system." In International Society of Limb Salvage 14th International Symposium on Limb Salvage.2007.

Gillespie, R., and J. Obrien. "Harrington instrumentation without fusion." In Journal of Bone and Joint Surgerybritish Volume, vol. 63, No. 3, pp. 461-461. 22 Buckingham Street, London, England WC2N 6ET: British Editorial Soc Bone Joint Surgery, 1981.

Goodship, Allen E., James L. Cunningham, and John Kenwright. "Strain rate and timing of stimulation in mechanical modulation of fracture healing." Clinical orthopaedics and related research 355 (1998): S105-S115.

Grass, P. Jose, A. Valentin Soto, and H. Paula Araya. "Intermittent distracting rod for correction of high neurologic risk congenital scoliosis." Spine 22, No. 16 (1997): 1922-1927.

Gray's Anatomy, http://education.yahoo.com/reference/gray/subjects/subject/128, published Jul. 1, 2007.

Grimer, R., S. Carter, R. Tillman, A. Abudu, and L. Jeys. "Non-Invasive Extendable Endoprostheses for Chiidren-Expensive but Worth It!." Journal of Bone & Joint Surgery, British vol. 93, No. SUPP I (2011): 5-5.

Grünert, R. D. "[The development of a totally implantable electronic sphincter]." Langenbecks Archiv fur Chirurgie 325 (1968): 1170-1174.

Guichet, Jean-Marc, Barbara Deromedis, Leo T. Donnan, Giovanni Peretti, Pierre Lascombes, and Flavio Bado. "Gradual femoral lengthening with the Albizzia intramedullary nail." The Journal of Bone & Joint Surgery 85, No. 5 (2003): 838- 848.

Gupta, A., J. Meswania, R. Pollock, S. R. Cannon, T. W. R. Briggs, S. Taylor, and G. Blunn. "Non-invasive distal femoral expandable endoprosthesis for limb-salvage surgery in paediatric tumours." Journal of Bone & Joint Surgery, British vol. 88, No. 5 (2006): 649-654.

Hankemeier S, Gösling T, Pape HC, et al. Limb lengthening with the Intramedullary Skeletal Kinetic Distractor (ISKD) Oper Orthop Traumatol. 2005;17:79-101.

Harrington PR (1962) Treatment of scoliosis. Correction and internal fixation by spine instrumentation. J Bone Joint Surg Am 44-A:591-610.

Hazem Elsebaie, M. D. "Single Growing Rods." Changing the Foundations: Does it affect the Results., J Child Orthop. (2007) 1:258.

Hennig, Alex C.; Incavo, Stephen J.; Beynnon, Bruce D.; Abate, Joseph A.; Urse, John S.; Kelly, Stephen / The safety and efficacy of a new adjustable plate used for proximal tibial opening wedge osteotomy in the treatment of unicompartmental knee osteoarthrosis. In: The journal of knee surgery, vol. 20, No. 1, Jan. 1, 2007, p. 6-14.

Hofmeister, M., C. Hierholzer, and V. Bühren. "Callus Distraction with the Albizzia Nail." In Practice of Intramedullary Locked Nails, pp. 211-215. Springer Berlin Heidelberg, 2006.

Horbach, T., D. Herzog, and I. Knerr. "First experiences with the routine use of the Rapid Port (TM) system with the Lap-Band (R)." In Obesity Surgery, vol. 16, No. 4, pp. 418-418. 3100 Bayview Ave, Unit 4, Toronto, Ontario M2N 5L3, Canada: F D-Communications Inc, 2006.

(56) References Cited

OTHER PUBLICATIONS

Hyodo, Akira, Helmuth Kotschi, Helen Kambic, and George Muschler. "Bone transport using intramedullary fixation and a single flexible traction cable." Clinical orthopaedics and related research 325 (1996): 256-268.

Ahlbom, A., U. Bergqvist, J. H. Bernhardt, J. P. Cesarini, M. Grandolfo, M. Hietanen, A. F. Mckinlay et al. "Guidelines for limiting exposure to time-varying electric, magnetic, and electromagnetic fields (up to 300 GHz). International Commission on Non-Ionizing Radiation Protection." Health Phys 74, No. 4 (1998): 494-522.

International Commission on Non-Ionizing Radiation Protection. "Guidelines on limits of exposure to static magnetic fields." Health Physics 96, No. 4 (2009): 504-514.

INVIS®/Lamello Catalog, 2006, Article No. 68906A001 GB.

Kasliwal, Manish K., Justin S. Smith, Adam Kanter, Ching-Jen Chen, Praveen V. Mummaneni, Robert A. Hart, and Christopher I. Shaffrey. "Management of high-grade spondylolisthesis." Neurosurgery Clinics of North America 24, No. 2 (2013): 275-291.

Kenawey, Mohamed, Christian Krettek, Emmanouil Liodakis, Ulrich Wiebking, and Stefan Hankemeier. "Leg lengthening using intramedullay skeletal kinetic distractor: results of 57 consecutive applications." Injury 42, No. 2 (2011): 150-155.

Kent, Matthew E., Arvind Arora, P. Julian Owen, and Vikas Khanduja. "Assessment and correction of femoral malrotation following intramedullary nailing of the femur." Acta Orthop Belg 76, No. 5 (2010): 580-4.

Klemme, William R., Francis Denis, Robert B. Winter, John W. Lonstein, and Steven E. Koop. "Spinal instrumentation without fusion for progressive scoliosis in young children." Journal of Pediatric Orthopaedics 17, No. 6 (1997): 734-742.

Korenkov, M., S. Sauerland, N. Yücel, L. Kohler, P. Goh, J. Schierholz, and H. Troidl. "Port function after laparoscopic adjustable gastric banding for morbid obesity." Surgical Endoscopy And Other Interventional Techniques 17, No. 7 (2003): 1068-1071.

Krieg, Andreas H., Bernhard M. Speth, and Bruce K. Foster. "Leg lengthening with a motorized nail in adolescents." Clinical orthopaedics and related research 466, No. 1 (2008): 189-197.

Kucukkaya, Metin, Raffi Armagan, and Unai Kuzgun. "The new intramedullary cable bone transport technique." Journal of orthopaedic trauma 23, No. 7 (2009): 531-536.

Lechner, W. L., W. Kirchmayr, and G. Schwab. "In vivo band manometry: a new method in band adjustment." In Obesity Surgery, vol. 15, No. 7, pp. 935-935. 3100 Bayview Ave, Unit 4, Toronto, Ontario M2N 5L3, Canada: F Dcommunicationsinc, 2005.

Lechner, W., M. Gadenstatter, R. Ciovica, W. Kirchmayer, and G. Schwab. "Intra-band manometry for band adjustments: The basics." In Obesity Surgery, vol. 16, No. 4, pp. 417-418. 3100 Bayview Ave, Unit 4, Toronto, Ontario M2N 5L3, Canada: F D-Communications Inc, 2006.

Li, G., S. Berven, N. A. Athanasou, and A. H. R. W. Simpson. "Bone transport over an intramedullary nail: A case report with histologic examination of the regenerated segment." Injury 30, No. 8 (1999): 525-534.

Lonner, Baron S. "Emerging minimally invasive technologies for the management of scoliosis." Orthopedic Clinics of North America 38, No. 3 (2007): 431-440.

Teli, Marco MD. "Measurement of Forces Generated During Distraction of Growing Rods, J." Marco Teli. Journal of Child Orthop 1 (2007): 257-258.

Matthews, Michael Wayne, Harry Conrad Eggleston, Steven D. Pekarek, and Greg Eugene Hilmas. "Magnetically adjustable intraocular lens." Journal of Cataract & Refractive Surgery 29, No. 11 (2003): 2211-2216.

Micromotion "Micro Drive Engineering-General catalogue" pp. 14-24; Jun. 2009.

Mineiro, Jorge, and Stuart L. Weinstein. "Subcutaneous rodding for progressive spinal curvatures: earlyresuits." Journal of Pediatric Orthopaedics 22, No. 3 (2002): 290-295.

Moe, John H., Khalil Kharrat, Robert B. Winter, and John L. Cummine. "Harrington instrumentation without fusion plus external orthotic support for the treatment of difficult curvature problems in young children." Clinical orthopaedics and related research 185 (1984): 35-45.

Montague, R. G., C. M. Bingham, and K. Atallah. "Magnetic gear dynamics for servo control." In MELECON 2010-2010 15th IEEE Mediterranean Electrotechnical Conference, pp. 1192-1197. IEEE, 2010.

Montague, Ryan, Chris Bingham, and Kais Atallah. "Servo control of magnetic gears." Mechatronics, IEEE/ASME Transactions on 17, No. 2 (2012): 269-278.

Nachemson, Alf, and Gosta Elfstrom. "Intravital wireless telemetry of axial forces in Harrington distraction rods in patients with idiopathic scoliosis." The Journal of Bone & Joint Surgery 53, No. 3 (1971): 445-465.

Nachlas, I. William, and Jesse N. Borden. "The cure of experimental scoliosis by directed growth control." The Journal of Bone & Joint Surgery 33, No. 1 (1951): 24-34.

Newton, P. "Fusionless Scoliosis Correction by Anterolateral Tethering . . . Can it Work?." In 39th Annual Scoliosis Research Society Meeting. 2004.

Observations by a third party under Article 115 EPC issued by the European Patent Office dated Feb. 15, 2010 in European Patent Application No. 08805612.2, Applicant: Soubeiran, Arnaud (7 pages).

Oh, Chang-Wug, Hae-Ryong Song, Jae-Young Roh, Jong-Keon Oh, Woo-Kie Min, Hee-Soo Kyung, Joon-Woo Kim, Poong-Taek Kim, and Joo-Chui Ihn. "Bone transport over an intramedullary nail for reconstruction of long bone defects in tibia." Archives of orthopaedic and trauma surgery 128, No. 8 (2008): 801-808.

Ozcivici, Engin, Yen Kim Luu, Ben Adler, Yi-Xian Qin, Janet Rubin, Stefan Judex, and Clinton T. Rubin. "Mechanical signals as anabolic agents in bone." Nature Reviews Rheumatology 6, No. 1 (2010): 50-59.

Patient Guide, VEPTR Vertical Expandable Prosthetic Titanium Rib, Synthes Spine (2005) (23pages).

Piorkowski, James R., Scott J. Ellner, Arun A. Mavanur, and Carlos A. Barba. "Preventing port site inversion in laparoscopic adjustable gastric banding." Surgery for Obesity and Related Diseases 3, No. 2(2007): 159-161.

Prontes, Isabel, http://wwwehow.com/about_4795793_longest-bone-body.html, published Jun. 12, 2012.

Rathjen, Karl, Megan Wood, Anna McClung, and Zachary Vest. "Clinical and radiographic results after implant removal in idiopathic scoliosis." Spine 32, No. 20 (2007): 2184-2188.

Ren, Christine J., and George A. Fielding. "Laparoscopic adjustable gastric banding: surgical technique." Journal of Laparoendoscopic & Advanced Surgical Techniques 13, No. 4 (2003): 257-263.

Reyes-Sánchez, Alejandro, Luis Miguel Rosales, and Victor Miramontes. "External fixation for dynamic correction of severe scoliosis." The Spine Journal 5, No. 4 (2005): 418-426.

Rinsky, Lawrence A., James G. Gamble, and Eugene E. Bieck. "Segmental Instrumentation Without Fusion in Children With Progressive Scoliosis." Journal of Pediatric Orthopedics 5, No. 6 (1985): 687-690.

Rode, V., F. Gay, A. J. Baraza, and J. Dargent. "A simple way to adjust bands under radiologic control." In Obesity Surgery, vol. 16, No. 4, pp. 418-418. 3100 Bayview Ave, Unit 4, Toronto, Ontario M2N 5L3, Canada: F Dcommunications Inc, 2006.

Schmerling, M. A., M. A. Wilkov, A. E. Sanders, and J. E. Woosley. "Using the shape recovery of nitinol in the Harrington rod treatment of scoliosis." Journal of biomedical materials research 10, No. 6 (1976): 879-892.

Scott, D. J., S. J. Tang, R. Fernandez, R. Bergs, and J. A. Cadeddu. "Transgastric, transcolonic, and transvaginal cholecystectomy using magnetically anchored instruments." In SAGES Meeting, p. P511. 2007.

Sharke, Paul. "The machinery of life." Mechanical Engineering 126, No. 2 (2004): 30.

Shiha, Anis, Mohamed Alam El-Deen, Abdel Rahman Khalifa, and Mohamed Kenawey. "Ilizarov gradual correction of genu varum deformity in adults." Acta Orthop Belg 75 (2009): 784-91.

(56) References Cited

OTHER PUBLICATIONS

Simpson, A. H. W. R., H. Shalaby, and G. Keenan. "Femoral lengthening with the intramedullary skeletal kinetic distractor." Journal of Bone & Joint Surgery, British vol. 91, No. 7 (2009): 955-961.

Smith, John T. "The use of growth-sparing instrumentation in pediatric spinal deformity." Orthopedic Clinics of North America 38, No. 4 (2007): 547-552.

Soubeiran, A., M. Gebhart, L. Miladi, J. Griffet, M. Neel, and J. Dubousset. "The Phenix M System. A Mechanical Fully Implanted Lengthening Device Externally Controllable Through the Skin with a Palm Size Permanent Magnet; Applications to Pediatric Orthopaedics." In 6th European Research Conference in Pediatric Orthopaedics. 2006.

Stokes, Oliver M., Elizabeth J. O'Donovan, Dino Samartzis, Cora H. Bow, Keith DK Luk, and Kenneth MC Cheung. Reducing radiation exposure in early-onset scoliosis surgery patients: novel use of ultrasonography to measure lengthening in magnet.

Sun, Zongyang, Katherine L. Rafferty, Mark A. Egbert, and Susan W. Herring. "Masticatory mechanics of a mandibular distraction osteogenesis site: interfragmentary micromovement." Bone 41, No. 2(2007): 188-196.

Takaso, Masashi, Hideshige Moriya, Hiroshi Kitahara, Shohei Minami, Kazuhisa Takahashi, Keijiro Isobe, Masatsune Yamagata, Yoshinori Otsuka, Yoshinori Nakata, and Masatoshi Inoue. "New remote-controlled growing-rod spinal instrumentation possibly applicable for scoliosis in young children." Journal of orthopaedic science 3, No. 6 (1998): 336-340.

Tello, Carlos A. "Harrington instrumentation without arthrodesis and consecutive distraction program for young children with severe spinal deformities. Experience and technical details." The Orthopedic clinics of North America 25, No. 2 (1994): 333-351.

Thaller, Peter Helmut, Julian Fürmetz, Florian Wolf, Thorsten Eilers, and Wolf Mutschler. "Limb lengthening with fully implantable magnetically actuated mechanical nails (PHENIX®)—Preliminary results." Injury 45 (2014): S60-S65.

Thompson, George H., Lawrence G. Lenke, Behrooz A. Akbarnia, Richard E. McCarthy, and Robert M. Campbell. "Early onset scoliosis: future directions." The Journal of Bone & Joint Surgery 89, No. suppl 1 (2007): 163-166.

Thonse, Raghuram, John E. Herzenberg, Shawn C. Standard, and Dror Paley. "Limb lengthening with a fully implantable, telescopic, intramedullary nail." Operative Techniques in Orthopedics 15, No. 4 (2005): 355-362.

Trias, A., P. Bourassa, and M. Massoud. "Dynamic loads experienced in correction of idiopathic scoliosis using two types of Harrington rods." Spine 4, No. 3 (1978): 228-235.

Veptr II. Vertical Expandable Prosthetic Titanium Rib II, Technique Guide, Systhes Spine (2008) (40 pages).

Verkerke, G. J., Koops H. Schraffordt, R. P. Veth, H. J. Grootenboer, L. J. De Boer, J. Oldhoff, and A. Postma. "Development and test of an extendable endoprosthesis for bone reconstruction in the leg." The International journal of artificial organs 17, No. 3 (1994): 155-162.

Verkerke, G. J., H. Schraffordt Koops, R. P. H. Veth, J. Oldhoff, H. K. L. Nielsen, H. H. Van den Kroonenberg, H. J. Grootenboer, and F. M. Van Krieken. "Design of a lengthening element for a modular femur endoprosthetic system." Proceedings of the Institution of Mechanical Engineers, Part H: Journal of Engineering in Medicine 203, No. 2 (1989): 97-102.

Verkerke, G. J., H. Schraffordt Koops, R. P. H. Veth, H. H. van den Kroonenberg, H. J. Grootenboer, H. K. L. Nielsen, J. Oldhoff, and A. Postma. "An extendable modular endoprosthetic system for bone tumour management in the leg." Journal of biomedical engineering 12, No. 2 (1990): 91-96.

Weiner, Rudolph A., Michael Korenkov, Esther Matzig, Sylvia Weiner, and Woiteck K. Karcz. "Initial clinical experience with telemetrically adjustable gastric banding." Surgical technology international 15 (2005): 63-69.

Wenger, H. L. "Spine Jack Operation in the Correction of Scoliotic Deformity: A Direct Intrathoracic Attack to Straighten the Laterally Bent Spine: Preliminary Report." Archives of Surgery 83, No. 6 (1961): 901-910.

White III, Augustus A., and Manohar M. Panjabi. "The clinical biomechanics of scoliosis." Clinical orthopaedics and related research 118 (1976): 100-112.

Yonnet, Jean-Paul. "Passive magnetic bearings with permanent magnets." Magnetics, IEEE Transactions on 14, No. 5 (1978): 803-805.

Yonnet, Jean-Paul. "A new type of permanent magnet coupling." Magnetics, IEEE Transactions on 17, No. 6 (1981): 2991-2993.

Zheng, Pan, Yousef Haik, Mohammad Kilani, and Ching-Jen Chen. "Force and torque characteristics for magnetically driven blood pump." Journal of Magnetism and Magnetic Materials 241, No. 2 (2002): 292-302.

International Search Report and Written Opinion for application serial No. PCT/US2015/000283 dated Mar. 18, 2016.

Magpole "Radially Aligned Sintered NdFeB Magnets" magpole. com, published on Feb. 4, 2014 (Feb. 4, 2014), accessed at <https://web.archive.org/web/20150726175708/http://www.magnetpole.com/radial-ring-magnets-58.html>.

Machine Translation of Japanese Application No. JP2002500053A, dated Jan. 8, 2002, 7 pages.

Machine Translation of USSR Soviet Union Application No. SU1197658A1, dated Dec. 15, 1985, retrieved from: https://patents.google.com/patent/SU1197658A1/en?oq=SU1197658A dated Jul. 5, 2022, 4 pages.

\* cited by examiner

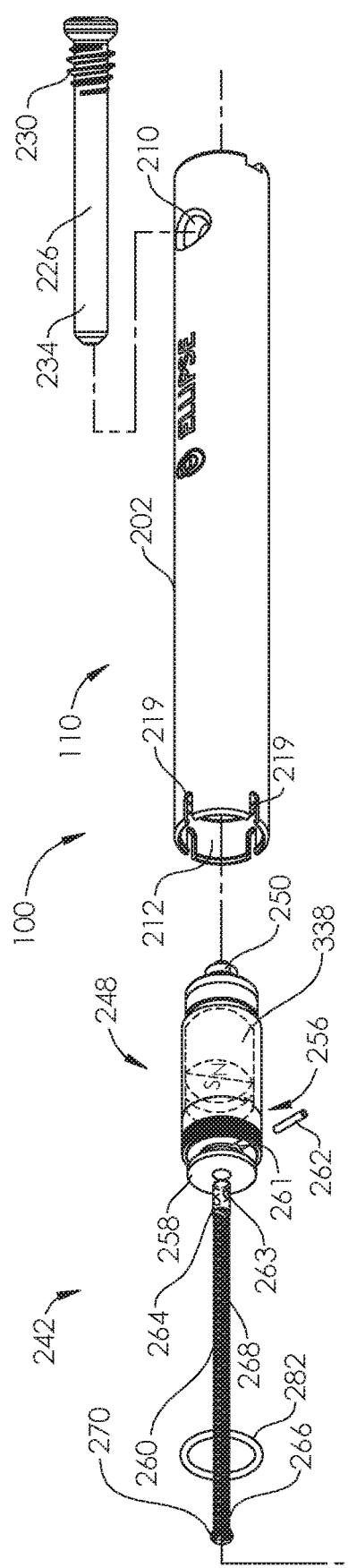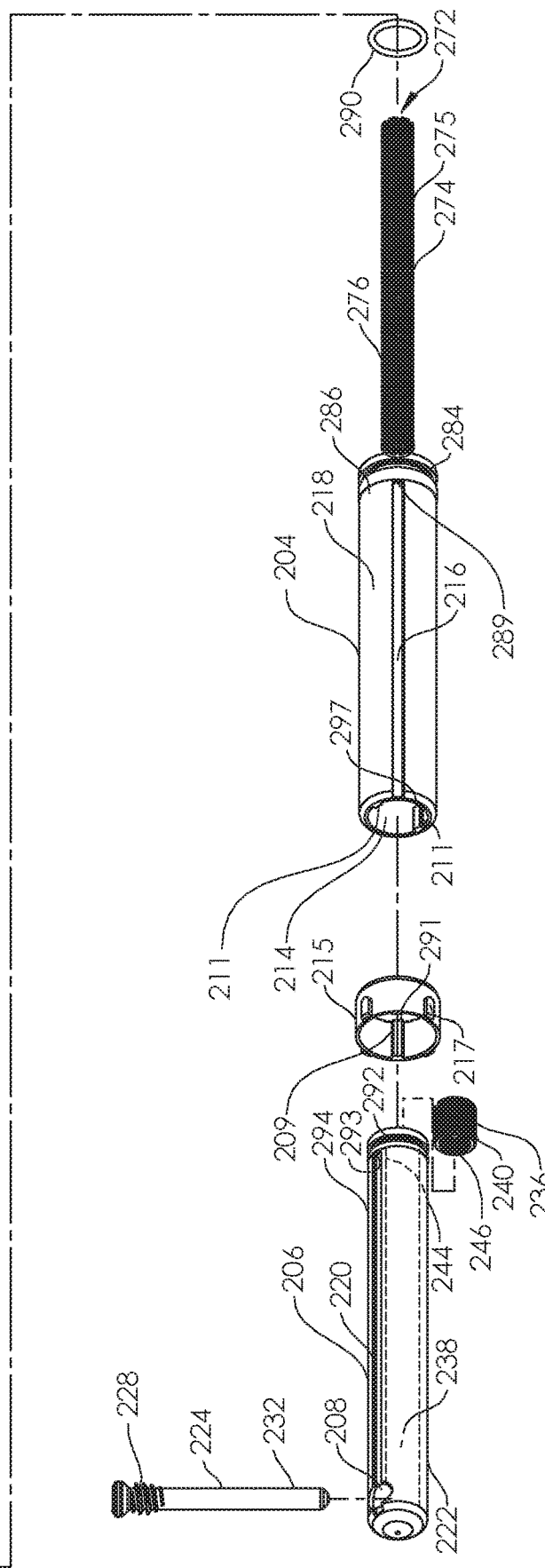
FIG. 4

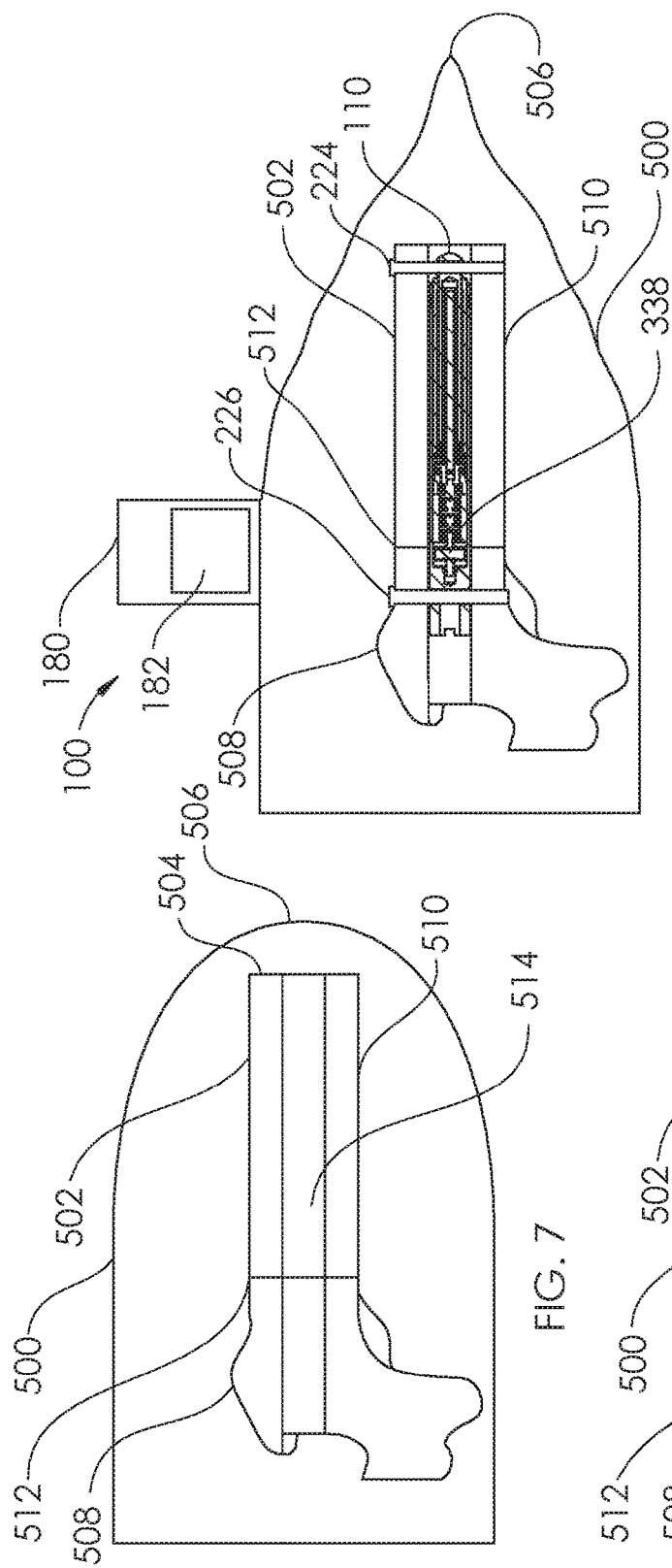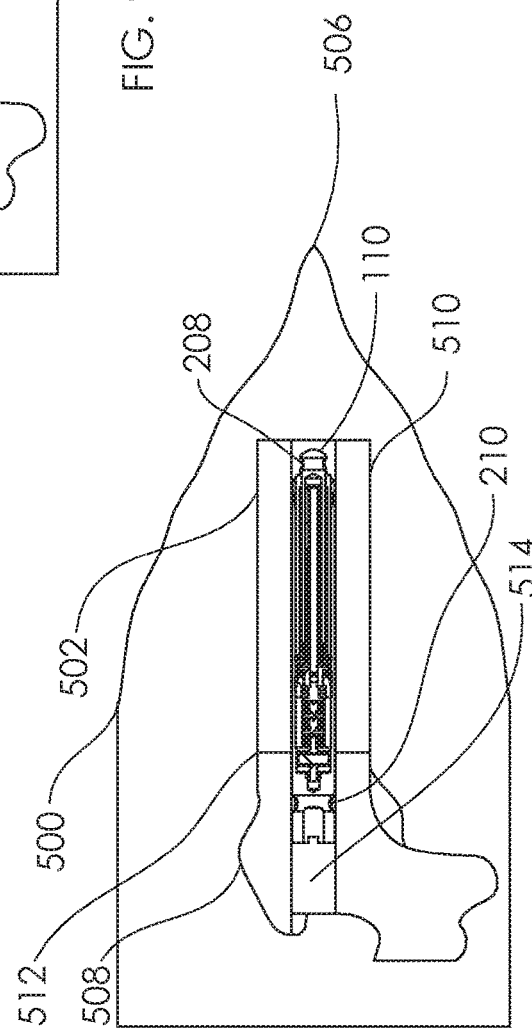

SYSTEMS AND METHODS FOR DISTRACTION

BACKGROUND

Any and all applications for which a foreign or domestic priority claim is identified in the Application Data Sheet as filed with the present application are hereby incorporated by reference under 37 CFR 1.57.

Scoliosis is a general term for the sideways (lateral) curving of the spine, usually in the thoracic or thoracolumbar region. Scoliosis is commonly broken up into different treatment groups, Adolescent Idiopathic Scoliosis, Early Onset Scoliosis and Adult Scoliosis.

Adolescent Idiopathic Scoliosis (AIS) typically affects children between ages 10 and 16, and becomes most severe during growth spurts that occur as the body is developing. One to two percent of children between ages 10 and 16 have some amount of scoliosis. Of every 1000 children, two to five develop curves that are serious enough to require treatment. The degree of scoliosis is typically described by the Cobb angle, which is determined, usually from x-ray images, by taking the most tilted vertebrae above and below the apex of the curved portion and measuring the angle between intersecting lines drawn perpendicular to the top of the top vertebrae and the bottom of the bottom. The term idiopathic refers to the fact that the exact cause of this curvature is unknown. Some have speculated that scoliosis occurs when, during rapid growth phases, the ligamentum flavum of the spine is too tight and hinders symmetric growth of the spine. For example, as the anterior portion of the spine elongates faster than the posterior portion, the thoracic spine begins to straighten, until it curves laterally, often with an accompanying rotation. In more severe cases, this rotation may actually create a noticeable deformity, wherein one shoulder is lower than the other. Currently, many school districts perform external visual assessment of spines, for example in all fifth grade students. For those students in whom an "S" shape or "C" shape is identified, instead of an "I" shape, a recommendation is given to have the spine examined by a physician, and commonly followed-up with periodic spinal x-rays.

Typically, patients with a Cobb angle of 20° or less are not treated, but are continually monitored, often with subsequent x-rays. Patients with a Cobb angle of 40° or greater are frequently candidates for fusion surgery. It should be noted that many patients do not receive such a spinal assessment, for numerous possible reasons. Many school districts do not perform this simple assessment, and many children do not regularly visit a physician. Therefore, the curve often progresses rapidly and severely. There is a large population of grown adults with untreated scoliosis, some having extreme cases exhibiting Cobb angles of 90° or greater. Many adults having untreated scoliosis, though, do not have pain associated with their deformity and live relatively normal lives, though oftentimes with restricted mobility and motion. In AIS, the ratio of females to males having Cobb angles under 10° is about one to one. However, at Cobb angles above 30°, females outnumber males by as much as eight to one. Fusion surgery can be performed on the AIS patients or on adult scoliosis patients. In a typical posterior fusion surgery, an incision is made down the length of the back and Titanium or stainless steel straightening rods are placed along the curved portion. These rods are typically secured to the vertebral bodies, for example with hooks or bone screws, or more specifically pedicle screws, in a manner that allows the spine to be straightened. Usually, at the section selected for fusion, the intervertebral disks are removed and bone graft material is placed to create the fusion. If autologous graft material is used, the bone is generally harvested from a hip via a separate incision.

Alternatively, fusion surgery may be performed anteriorly. A lateral and anterior incision is made for access. Usually, one of the lungs is deflated in order to allow access to the spine from this anterior approach. In a less-invasive version of the anterior procedure, instead of the single long incision, approximately five incisions, each about three to four cm long are made in several of the intercostal spaces (between the ribs) on one side of the patient. In one version of this minimally invasive surgery, tethers and bone screws are placed and secured to the vertebra on the anterior convex portion of the curve. Currently, clinical trials are being performed in which staples are used instead of the tether/screw combination. One advantage of this surgery in comparison with the posterior approach is that scars resulting from the several smaller incisions are not as dramatic, though they are still located in a visible area, when a bathing suit, for example, is worn. Staple-based techniques have experienced some difficulty in clinical trials. The staples tend to pull out of the bone when a critical stress level is reached.

In some cases, after surgery, the patient will wear a protective brace for a few months as the fusing process occurs. Once the patient reaches spinal maturity, it may be difficult to remove the rods and associated hardware in a subsequent surgery because the fusion of the vertebra usually incorporates the rods themselves. Therefore, standard practice is to leave this implant in for life. With either of these two surgical methods, after fusion the patient's spine is rendered straight, but, depending on the number of vertebrae that were fused, limitations in the degree of flexibility, both in bending and twisting, are often observed. As fused patients mature, the fused section of the spine can impart significant stresses on the adjacent non-fused vertebrae, and often, other problems including pain can occur in these areas, sometimes necessitating further surgery. This tends to be in the lumbar portion of the spine that is prone to problems in aging patients. Many physicians are now interested in fusionless surgery for scoliosis, which may be able to eliminate, or at least reduce, one or more of the drawbacks of fusion.

One group of patients in which the spine is especially dynamic is the subset known as Early Onset Scoliosis (EOS), which typically occurs in children before the age of five, and more often in boys than in girls. EOS is a more rare condition than AIS, occurring in only about one or two out of 10,000 children, but can be severe, sometimes affecting the normal development of organs. Because the spines of these children will generally grow a large amount after treatment, non-fusion distraction devices known as growing rods and a device known as the VEPTR—Vertical Expandable Prosthetic Titanium Rib ("Titanium Rib") have been developed. These devices are typically adjusted approximately every six months, or as required to match the child's growth, until the child is at least eight years old, and sometimes until they are 15 years old. Each adjustment requires a surgical incision to access the adjustable portion of the device. Because the patients may receive the device at an age as early as six months old, this treatment may require a large number of surgeries. Because of the multiple surgeries, these patients have a rather high incidence of infection.

Returning to the AIS patients, the treatment methodology for those with a Cobb angle between 20° and 40° is quite controversial. Many physicians prescribe a brace (for example, the Boston Brace) for a patient to wear on his body, under the clothes, 18 to 23 hours a day until the patient become skeletally mature (e.g., age 16). Because these patients are all passing through their socially demanding adolescent years, it is a quite serious prospect to choose between wearing a somewhat bulky brace that covers most of the upper body, having fusion surgery that may leave large scars and limit motion, and doing nothing and risking becoming disfigured and possibly disabled. It is common knowledge that many patients have, at times, hidden their braces, for example, in a bush outside of school, in order to escape embarrassment associated with the brace(s). The patient compliance with brace wearing has been so problematic that special braces have been constructed that sense the body of the patient and keep track of the amount of time per day that the brace is worn. Even such special braces have problems with patient compliance: patients have been known to place objects into unworn braces of this type in order to fool the sensor. Coupled with the inconsistent patient compliance with brace usage, is a feeling by many physicians that braces, even if used properly, are not at all effective at curing scoliosis. Physicians may agree that bracing can possibly slow down or even temporarily arrest curve (Cobb angle) progression, but they have noted that as soon as the treatment period ends and the brace is no longer worn, often the scoliosis progresses rapidly to a Cobb angle even more severe than it was at the beginning of treatment. Some say the reason for the supposed ineffectiveness of the brace is that it braces only on a portion of the torso, and not on the entire spine. Currently a prospective, randomized, 500-patient, clinical trial known as BrAIST (Bracing in Adolescent Idiopathic Scoliosis Trial) is enrolling patients, 50% of whom will be treated with the brace and 50% of who will simply be watched. Cobb angle data from these patients will be measured continually up until they reach skeletal maturity, or until a Cobb angle of 50° is reached, at which time the patient will likely undergo surgery. Many physicians feel that the BrAIST trial will show that braces are completely ineffective. If this is the case, the quandary about what to do with AIS patients who have a Cobb angle of between 20° and 40° will only become more pronounced. It should be noted that the patient population having a Cobb angle of 20-40° is as much as ten times larger than the population having a Cobb angle of 40° and greater.

Distraction osteogenesis, also known as distraction callotasis and osteodistraction has been used successfully to lengthen various bones of the body (e.g., long bones). Typically, the bone, if not already fractured, is purposely fractured by means of a corticotomy, and the resulting two segments of bone are gradually distracted apart, thereby allowing new bone to form in the gap. If the distraction rate is too high, there is a risk of nonunion. If the rate is too low, there is a risk that the two segments will prematurely, fuse to each other more than desired before the distraction period is complete. Once the desired length of the bone is achieved using this process, the bone is allowed to consolidate. Distraction osteogenesis applications are mainly focused on the growth of the femur or tibia, but may also include the humerus, the jaw bone (micrognathia), or other bones. There are many reasons for lengthening or growing bones which may be desirable. The applications including, but not limited to: post osteosarcoma bone cancer; cosmetic lengthening (both legs-femur and/or tibia) in short stature or dwarfism/achondroplasia; lengthening of one limb to match the other (congenital, post-trauma, post-skeletal disorder, prosthetic knee joint), nonunions.

Distraction osteogenesis using external fixators has been done for many years, but the external fixator can be unwieldy and painful for the patient. It can also subject the patient to the risk of pin track infections, joint stiffness, loss of appetite, depression, cartilage damage and other side effects. An external fixator, e.g., around the patient/patient's limb, can also delay the beginning of rehabilitation.

In response to the shortcomings of external fixator distraction, intramedullary distraction nails which may be contained entirely within the bone have been surgically implanted. Some such nails may be automatically lengthened via repeated rotation of the patient's limb, which can sometimes be painful to the patient, and can often proceed in an uncontrolled fashion. This therefore makes it difficult to follow the strict daily or weekly lengthening regime that avoids nonunion (if too fast) or early consolidation (if too slow). Lower limb distraction rates are generally on the order of about one mm per day. Other intramedullary nails which have an implanted motor and may be remotely controlled by an antenna have also been developed. These devices are designed to be lengthened or distracted in a controlled manner, but, due to their complexity, may not be manufacturable as an affordable product. Others have proposed intramedullary distractors containing an implanted magnet, which allows the distraction to be driven electromagnetically by an external stator. Because of the complexity and size of the external stator, this technology has not been reduced to a simple and/or cost-effective device, which can be taken home to allow patients to do daily lengthenings. Non-invasively adjustable implantable distraction devices, at least one embodiment of which is magnetically non-invasively adjustable, have been developed and used clinically in both scoliosis and limb lengthening patients.

Knee osteoarthritis is a degenerative disease of the knee joint that affects a large number of patients, particularly over the age of 40. The prevalence of this disease has increased significantly over the last several decades, attributed partially, but not completely, to the rising age of the population as well as the increase in obesity. The increase may also be due to an increase in highly active people within the population. Knee osteoarthritis is caused mainly by long term stresses on the knee that degrade the cartilage covering the articulating surfaces of the bones in the knee joint. Oftentimes, the problem becomes worse after a particular trauma event, but it can also be a hereditary process. Symptoms include, but are not limited to, pain, stiffness, reduced range of motion, swelling, deformity, and muscle weakness. Osteoarthritis may include one or more of the three compartments of the knee: the medial compartment of the tibiofemoral joint, the lateral compartment of the tibiofemoral joint, and the patellofemoral joint. In severe cases, partial or total replacement of the knee is performed in order to replace the diseased portions with new weight bearing surfaces for the knee, typically made from implant grade plastics or metals. These operations may involve significant post-operative pain and require substantial physical therapy. The recovery period may last weeks or months. Several potential complications of this surgery exist, including deep venous thrombosis, loss of motion, infection, and bone fracture. After recovery, surgical patients who have received uni-compartmental or total knee replacement must significantly reduce their activity, removing running and high energy sports completely from their lifestyle.

For these reasons, surgeons are attempting to intervene early in order to delay or even preclude knee replacement surgery. Osteotomy surgeries may be performed on the femur or tibia, in order to change the angle between the femur and tibia, and thus adjust the stresses on the different portions of the knee joint. In closed wedge or closing wedge osteotomy, an angled wedge of bone is removed, and the remaining surfaces are fused together, creating a new improved bone angle. In open wedge osteotomy, a cut is made in the bone and the edges of the cut are opened, creating a new angle. Bone graft is often used to fill in the newly-opened, wedge-shaped space, and, often, a plate is attached to the bone with bone screws. Obtaining the correct angle during either of these types of osteotomy is almost always difficult, and, even if the final result is close to what was desired, there can be a subsequent loss of the correction angle. Some other complications associated with this technique include nonunion and material failure.

Amputation of the arm or the leg can result in a residual limb, with a stump, having a shortened bone (e.g., a shortened femur, tibia, fibula, humerus, radius or ulna). A prosthetic limb or prosthetic limb attachment which may be attached to a residual limb may have problems fitting or functioning when attached to a residual limb having insufficient bone length. There may be poor energy transfer between the residual limb and the attached prosthesis, as short lever arms generate less torque for a given force. This functional deficit is compounded when the lever arm is encased in very compliant tissue, such as a residual femur that is surrounded by the soft tissues of the thigh. This may further impair prosthesis control. Individuals having short residual limbs may display gait asymmetries and gait changes. The wearer of a prosthetic limb who has a relatively short residual limb may exhibit compensatory changes that affect posture and cause discomfort or injury to the spine or other body structures. Amputation may occur or may be performed for several reasons including war-related injuries, motor vehicle accidents, including motorcycle accidents, other types of trauma or cancer of the bone or other adjacent tissue.

In addition to the many different types of implantable distraction devices that are configured to be non-invasively adjusted, implantable non-invasively adjustable non-distraction devices have also been envisioned, for example, adjustable restriction devices for gastrointestinal disorders such as GERD, obesity, or sphincter laxity (such as in fecal incontinence), or other disorders such as sphincter laxity in urinary incontinence. These devices, too, may incorporate magnets to enable non-invasive adjustment.

SUMMARY

The present disclosure provides for a system for moving a portion of a patient's body including a housing having a first cavity extending along a longitudinal axis, a first distraction rod having a proximal end and a distal end and configured to be telescopically displaceable from within the first cavity along the longitudinal axis, the first distraction rod having a second cavity extending along the longitudinal axis, a second distraction rod having a proximal end and a distal end and configured to be telescopically displaceable from within the second cavity along the longitudinal axis, and a drive system configured to move the first distraction rod in relation to the housing and to move the second distraction rod in relation to the first distraction rod.

The present disclosure further provides for a method of modifying a residual limb of a patient including the steps of providing a distraction device having a housing extending along a longitudinal axis, a first distraction rod having a proximal end and a distal end, the first distraction rod and the housing being telescopically displaceable with respect to each other along the longitudinal axis, the first distraction rod having a cavity extending along the longitudinal axis, a second distraction rod having a proximal end and a distal end and being configured to be telescopically displaceable from within the cavity along the longitudinal axis, and a drive system configured to move the first distraction rod in relation to the housing and to move the second distraction rod in relation to the first distraction rod, attaching the housing to a first portion of a bone within the residual limb, attaching the second distraction rod to a second portion of the bone within the residual limb, decoupling the first portion of the bone from the second portion of the bone, and wherein the distraction device is actuatable such that the first distraction rod is caused to move in relation to the housing and the second distraction rod is caused to move in relation to the first distraction rod, to increase at least one of a force or a distance between the first portion of the bone and the second portion of the bone.

The present disclosure further provides for a system for moving a portion of a patient's body including a housing having a first cavity extending along a longitudinal axis, a first distraction rod having a proximal end and a distal end, the first distraction rod and the housing being telescopically displaceable with respect to each other along the longitudinal axis, the first distraction rod having a cavity extending along the longitudinal axis, a second distraction rod having a proximal end and a distal end and configured to be telescopically displaceable from within the second cavity along the longitudinal axis, and a drive system configured to move the first distraction rod in relation to the housing and to move the second distraction rod in relation to the first distraction rod.

In one embodiment, a system for moving a portion of a patient's body is provided. The system for moving a portion of a patient's body includes: a housing having a first cavity extending along a longitudinal axis; a first distraction rod having a proximal end, a distal end, and a second cavity extending between the proximal end and the distal end, and being configured for telescopic displacement from within the first cavity; a second distraction rod having a proximal end and a distal end, and being configured for telescopic displacement from within the second cavity; and a drive system configured to move at least one of the first distraction rod and the second distraction rod.

In one embodiment, a method of modifying a residual limb is provided. The method of modifying a residual limb of a patient includes the steps of: providing a distraction device comprising: a housing extending along a longitudinal axis; a first distraction rod having a proximal end and a distal end, the first distraction rod and the housing being telescopically displaceable with respect to each other, the first distraction rod having a cavity extending along the longitudinal axis; a second distraction rod having a proximal end and a distal end and configured to be telescopically displaceable from within the cavity; and a drive system configured to move at least one of the first distraction rod in relation to the housing and the second distraction rod in relation to the first distraction rod; decoupling the first portion of the bone from the second portion of the bone; attaching the housing to a first portion of a bone within the residual limb; attaching the second distraction rod to a second portion of the bone within the residual limb, wherein the distraction device is actuatable such that the first distraction rod is caused to move in relation to the housing and the second distraction rod is caused to move in relation to the first distraction rod, to increase at least one of a force or a distance between the first portion of the bone and the second portion of the bone.

In another embodiment, a system for moving a portion of a patient's body is provided. The system for moving a portion of a patient's body includes: a housing having a first cavity extending along a longitudinal axis; a first distraction rod having a proximal end, a distal end, and a cavity extending along the longitudinal axis, the first distraction rod and the housing being telescopically displaceable with respect to each other along the longitudinal axis; a second distraction rod having a proximal end and a distal end, and configured to be telescopically displaceable from within the second cavity along the longitudinal axis; a drive system configured to move the first distraction rod in relation to the housing and to move the second distraction rod in relation to the first distraction rod.

In still another embodiment, a system for moving a portion of a patient's body is provided. The system for moving a portion of a patient's body includes: a housing having a first cavity; a first distraction rod having a proximal end, a distal end, and a second cavity, wherein the first distraction rod is configured for telescopic displacement relative to the first cavity; a second distraction rod having a proximal end and a distal end, wherein the second distraction rod is configured for telescopic displacement from within the second cavity; and a drive system configured to move at least one of the first distraction rod and the second distraction rod.

In one embodiment, a method of modifying a residual limb of a patient is provided. The method of modifying a residual limb includes the steps of: providing a distraction device comprising: a housing having a first cavity; a first distraction rod having a proximal end, a distal end, and a second cavity, wherein the first distraction rod is telescopically displaceable relative to the first cavity; a second distraction rod having a proximal end and a distal end, wherein the second distraction rod is telescopically displaceable from within the second cavity; and a drive system configured to move at least one of the first distraction rod and the second distraction rod with respect to the housing; then decoupling a first portion of a bone within the residual limb from a second portion of the bone; attaching the housing to one of the first portion and the second portion of the bone within the residual limb; and attaching the second distraction rod to the other of the first portion and the second portion of the bone within the residual limb, wherein the drive system is configured to be actuated so as to increase at least one of a force and a distance between the first portion and the second portion of the bone.

BRIEF DESCRIPTION OF THE DRAWINGS

FIG. 4 illustrates an exploded view of a distraction device.

FIG. 7 illustrates a residual limb.

FIG. 8 illustrates a distraction device inserted within a medullary canal of a bone of a residual limb.

FIG. 9 illustrates a distraction device secured within a medullary canal of a bone of a residual limb.

DETAILED DESCRIPTION

Embodiments of the adjustable devices for implanting into the body disclosed herein are capable of achieving a large (e.g., greater than 40%, greater than, greater than 60%, greater than 80%, greater than 100% and even greater than 120%) total amount of adjustment length in comparison to the total length of the adjustable portion of the device. Adjustable devices may include distraction devices, for example distraction devices for orthopedic applications, including, but not limited to scoliosis, limb lengthening, bone transport, spinous process distraction, tibial wedge osteotomy adjustment, and spondylolisthesis. Maintaining a small size an adjustable (e.g., distraction and/or retraction) implant to fit into a small, short space within the body, and achieving large amounts of adjustable length have historically been conflicting design goals.

Figure 1:
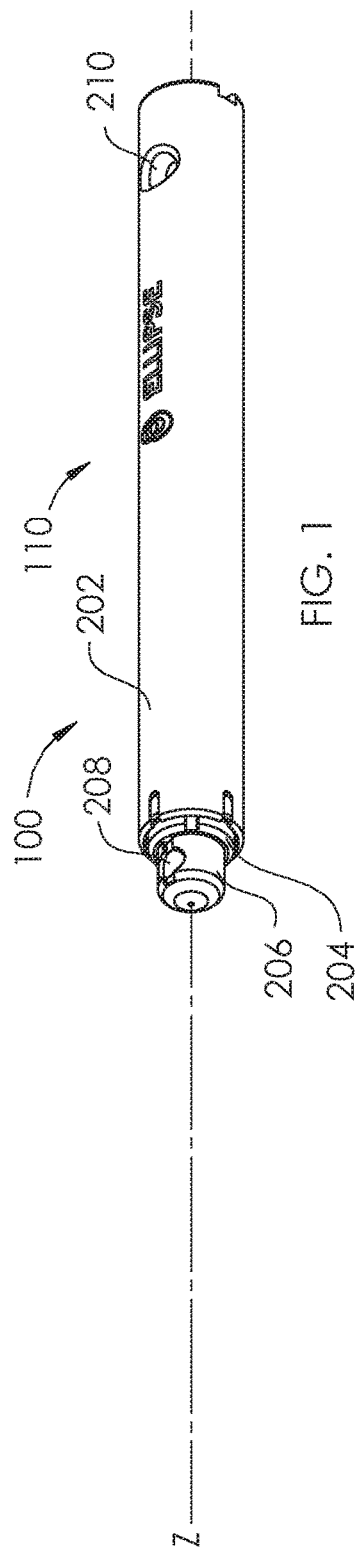
FIG. 1 is a perspective view of a distraction device.
Figure 2:
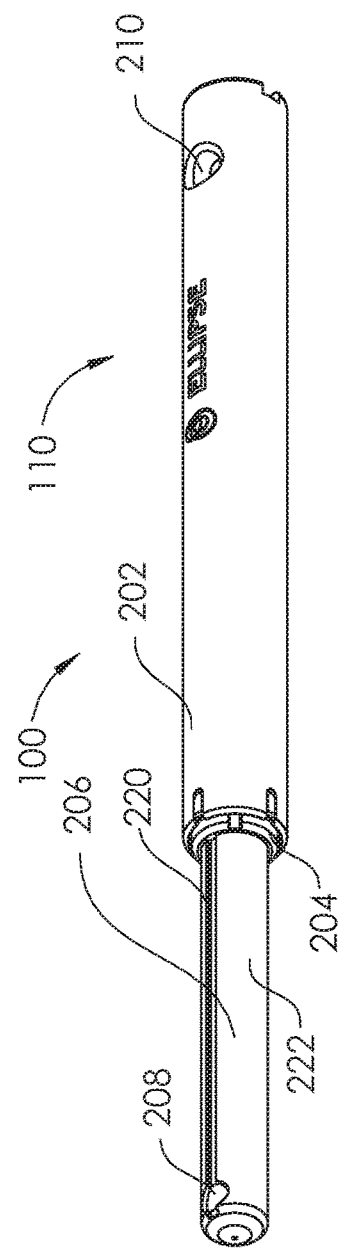
FIG. 2 illustrates the distraction device of FIG. 1 in a partially distracted configuration.
Figure 3:
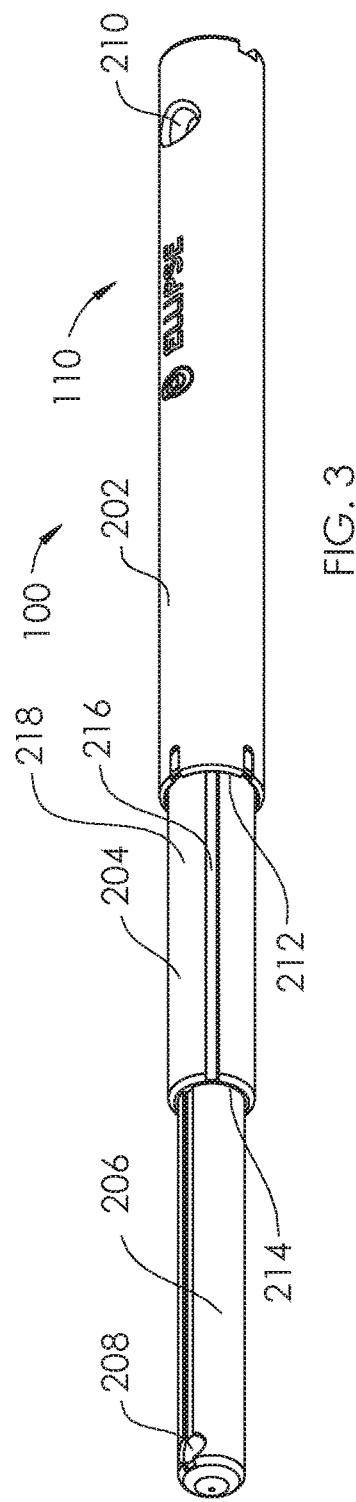
FIG. 3 illustrates the distraction device of FIG. 1 in a fully distracted configuration.

FIGS. 1-3 illustrate an embodiment of an implantable adjustable system 100 comprising a distraction device 110. The distraction device 110 comprises a housing 202, a first distraction rod 204 and a second distraction rod 206. The second distraction rod 206 and the housing 202 are each configured for coupling to a patient. The second distraction rod 206 contains one or more holes 208 for passing an anchor with which to secure the distraction device 110 to a patient. One of the one or more holes 208 may be located between about 3 mm and 15 mm, or approximately 5 mm, from the distal end of the second distraction rod 206. The housing 202 contains one or more holes 210 for passing an anchor with which to secure the distraction device 110 to the patient. One of the one or more holes 210 may be located between about 5 mm and about 20 mm, or approximately 10 mm, from the proximal end of the housing 202. The housing 202 may have a diameter of between about 8.5 mm and about 16 mm, or between about 10.5 mm and about 14.5 mm, or about 14 mm. In some embodiments, the anchor is a bone anchor, for example, a bone screw 224, 226 (FIG. 4). The bone screws 224, 226 may be between about 3 mm and about 6 mm in diameter. In some embodiments, bone screw 244 is 4 mm in diameter and bone screw 226 is 5 mm in diameter. The bone screws may be between about 18 mm and about 80 mm in length, or between about 20 mm and about 75 mm in length. However, other types of anchoring and/or connection are contemplated for coupling the second distraction rod 206 and the housing 202 to the bone of the patient. As illustrated in FIG. 2, the second distraction rod 206 may be configured to be telescopically displaceable with respect to the housing 202. As seen in FIG. 2, the second distraction rod 206 may be configured to also be telescopically displaceable with respect to the first distraction rod 204. As illustrated in FIG. 3, the first distraction rod 204 may be configured to be telescopically displaceable with respect to the housing 202. The first distraction rod 204 may be longitudinally displaceable from within a cavity 212 in the housing 202 that extends along longitudinal axis Z (FIG. 1). The first distraction rod 204 may be configured to be telescopically displaceable along the longitudinal axis Z. The first distraction rod 204 has a cavity 214, with the second distraction rod 206 configured to telescopically displace from the cavity 214 along the longitudinal axis Z. In some embodiments, the first distraction rod 204 may have a diameter of between about 8 mm and about 13 mm, or about 11.5 mm. In some embodiments, the second distraction rod 206 may have a diameter of between about 5 mm and about 11 mm, or about 9 mm. In some embodiments it may be desired that there be no rotational motion (about the longitudinal axis Z) between at least one of the housing 202, the first distraction rod 204, and the second distraction rod 206. In some embodiments, one or more first longitudinal grooves 216 extends along an exterior surface 218 of the first distraction rod 204 and is slidingly engaged by protrusions 209 (FIG. 4) which extend in an inward radial direction from the interior of a cap 215, which is coupled to the housing 202, thus allowing longitudinal displacement between the first distraction rod 204 and the housing 202, but not allowing rotation between them. External ribs 217 on the cap 215 insert into grooves 219 in the housing 202 during assembly. The cap 215 may be snapped into place on the housing 202 or otherwise secured by adhesive, welding, soldering, brazing or other methods. One or more second longitudinal grooves 220 extending along an exterior surface 222 of the second distraction rod 206 are slidingly engaged by protrusions 211 (FIG. 4) which extend from the interior of the cavity 214 of the first distraction rod 204 in an inward radial direction, thus allowing longitudinal displacement between the second distraction rod 206 and the first distraction rod 204, but not allowing rotation between them. If the distraction device 110 is used for the purpose of distracting two pieces of bone (e.g., move two bones or two pieces of a bone apart from each other), then the protrusions 209, 211 and longitudinal grooves 216, 220 make it possible to assure that there may be substantially no rotation between the two bone pieces. As seen in FIG. 3, the first longitudinal grooves 216 and the second longitudinal grooves 220 can be purposely configured to reside at different clock positions (in circumferential relation to the longitudinal axis Z (FIG. 1), in order to make enough room in the second distraction rod 206, the first distraction rod 204, and the housing 202, so that wall thickness, and thus strength and durability, are not compromised.

Figure 5:
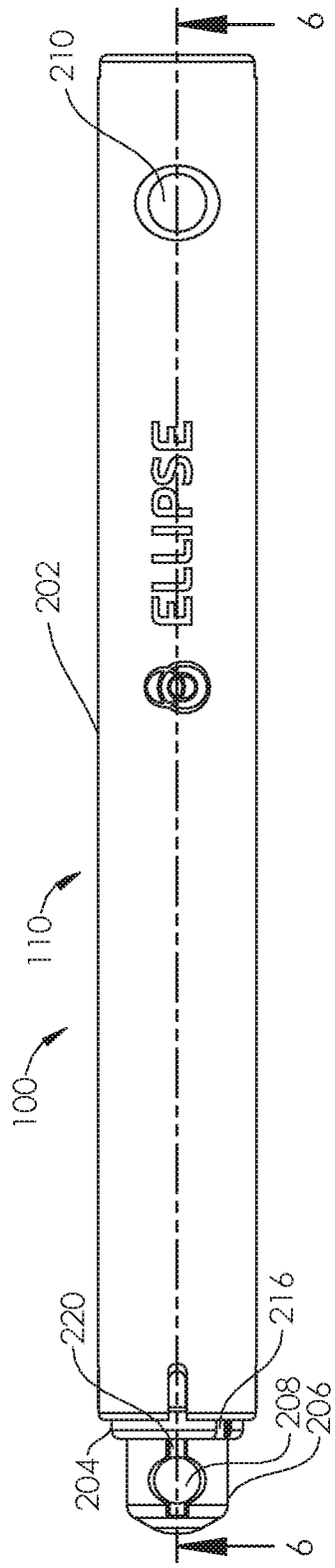
FIG. 5 illustrates an elevation view of a distraction device.
Figure 6:
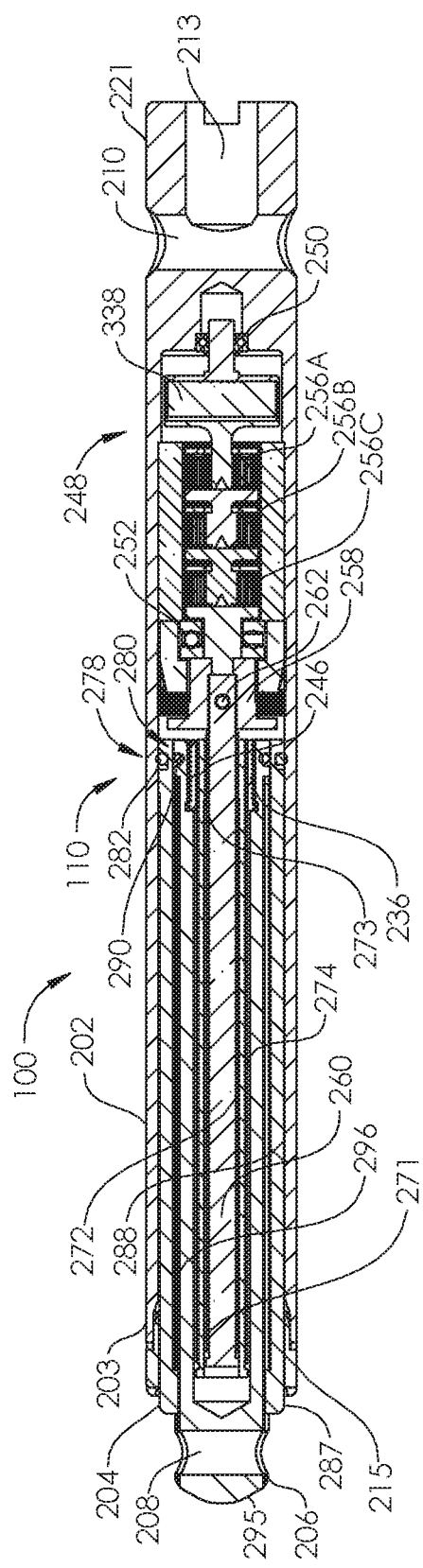
FIG. 6 illustrates a sectional view of the distraction device of FIG. 5 taken along line 6-6.

Turning to FIG. 4, bone screws 224, 226 are depicted having unicortical threads 228, 230 and unthreaded shafts 232, 234, however, any type of bone screw, for example a fully-threaded bone screw, may be used for placement through the holes 208, 210. The holes 208, 210 may be perpendicular to the longitudinal axis Z, or may be at various angles, depending upon the configuration through which they are to be coupled to the bone. With further reference to FIGS. 4-6, the distraction device 110 comprises a driving element 242 configured to be activated by a remotely applied source. A nut 236 may be secured within a cavity 238 in the second distraction rod 206. The nut 236 may have external threads 240, which are engaged or bonded into an internal thread 244 of the cavity 238. The nut 236 also contains an internal thread 246. A magnetic assembly 248 may be held between a radial bearing 250 and a thrust bearing 252 (FIG. 6), and comprises a radially-poled permanent magnet 338 which is rotationally coupled to one or more gear modules 256 (e.g., planetary gearing). The thrust bearing 252 and radial bearing 250 may be restrained at their longitudinal extents in relation to the housing 202, in order to maintain the magnetic assembly 248 within the housing 202, while allowing it and its components to rotate freely. In some embodiments, the permanent magnet 338 may be carried within one or more cylindrical housings or cups. The one or more gear modules 256 output (through the interior of the thrust bearing 252) to a coupler 258, which may be rotationally coupled to a first lead screw 260 via a pin 262, which passes through a hole 261 in the coupler 258 and a hole 263 at a proximal end 264 of the first lead screw 260. The first lead screw 260 also has an abutment 270 at its distal end 266, and comprises an external thread 268. In some embodiments, the gear modules 256 may provide a gear ratio of 4:1, 16:1, 64:1, 256:1 between the magnet 338 and the first lead screw 260, or another ratio. In some embodiments, the first lead screw 260 may be directly coupled to the magnet 338, and thus provide 1:1 rotation. The first lead screw 260 may be threadingly engaged with an internal thread 272 of a second lead screw 274. The majority of the length of the second lead screw 274 may be an internal bore 271 with a diameter that is equal to or greater than the major diameter of the internal thread 272. The internal thread 272 may be located only at the proximal end 275 of the second lead screw 274. In some embodiments, the length of the internal thread 272 along the longitudinal axis Z may be about 3 mm to about 7 mm, or about 5.5 mm. The external thread 276 of the second lead screw 274 may be threadingly engaged with the internal thread 246 of the nut 236 which may be secured within the second distraction rod. An exemplary external thread specification for each of the lead screws 260, 274 may be 80 threads per inch.

The interior contents of the distraction device 110, including the interior portions of cavities 212, 214, 238, which contain the magnetic assembly 248 and the lead screws 260, 274, are protected from external fluids and materials by dynamic seals 278, 280. A first dynamic seal 278 includes an o-ring 282, which resides within a circumferential groove 284 at a proximal end 286 of the first distraction rod 204. The o-ring 282 seals along an inner cylindrical surface 288 of the housing 202, and maintains the dynamic seal 278 throughout the longitudinal displacement of the first distraction rod 204 with the housing 202. A second dynamic seal 280 includes an o-ring 290, which resides within a circumferential groove 292 at a proximal end 294 of the second distraction rod 206. The o-ring 290 seals along an inner cylindrical surface 296 of the first distraction rod 204, and maintains the dynamic seal 280 throughout the longitudinal displacement of the second distraction rod 206 with the first distraction rod 204.

Figure 12:
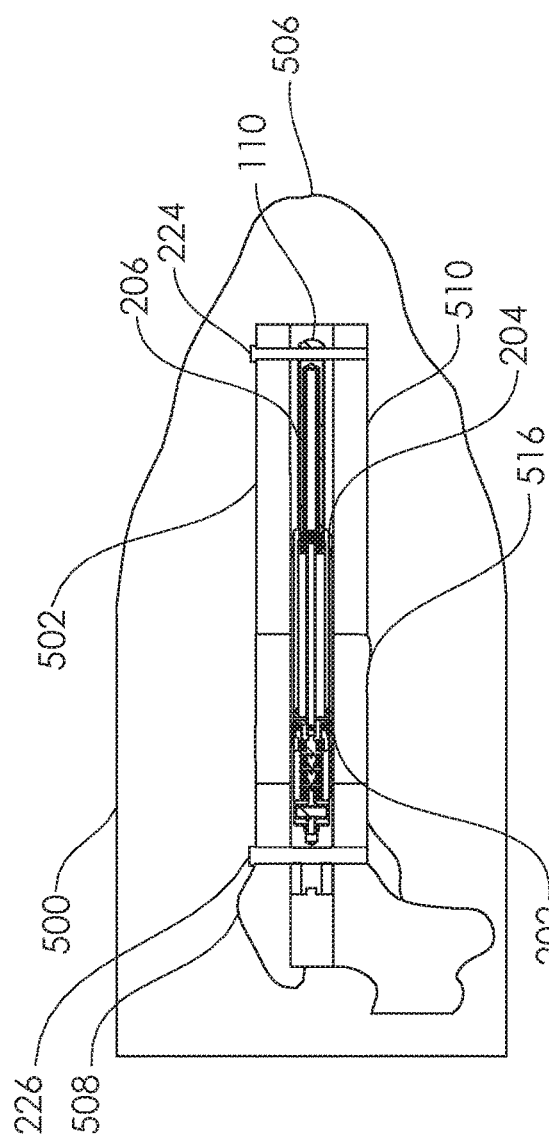
FIG. 12 illustrates a distraction device and residual limb after partial distraction.

FIG. 6 illustrates the distraction device 110 in a fully undistracted (or retracted) condition, wherein the distal end 287 of the first distraction rod 204 and the distal end 295 of the second distraction rod 206 are located near the distal end 203 of the housing 202. In use, when the magnet 338 is rotated (e.g., by an externally-applied moving magnetic field) (and caused to rotate in a first rotational direction) the first lead screw 260 may be turned (through the gear ratios of gear modules 256A, 256B, 256C). The turning of the external thread 268 of the first lead screw 260 in relation to the internal thread 272 of the second lead screw 274, thus causes both the second distraction rod 206 and the second lead screw 274 to longitudinally extend from the housing 202. As described, in at least some embodiments, the second distraction rod 206 is prevented from rotation with respect to the first distraction rod 204 and the housing 202. In some embodiments, the second lead screw 274 does not turn as it longitudinally extends with the second distraction rod 206, thus the first distraction rod 204 does not longitudinally extend in relation to the housing 202. FIG. 12, which will be referred to later when describing the procedure for lengthening a bone in a residual limb, shows the distraction rod 110 after the second distraction rod 206 has been longitudinally extended in relation to both the housing 202 and the first distraction rod 204. For this first stage of distraction to occur as described, the frictional torque between the external thread 268 of the first lead screw 260 and the internal thread 272 of the second lead screw 274 is less than the frictional torque between the external thread 276 of the second lead screw 274 and the internal thread 246 of the nut 236. This tends to be the case, however, other assembly steps and materials may additionally be provided in order to assure this. For example, in some embodiments, a silicone lubricant or a Krytox® lubricant may be applied to the external thread 268 of the first lead screw 260 and/or the internal thread 272 of the second lead screw 274, but not to the external thread 276 of the second lead screw 274 and the internal thread 246 of the nut 236. In some embodiments, the lubricant may be applied more liberally to the external thread 268 of the first lead screw 260 and/or the internal thread 272 of the second lead screw 274 than to the external thread 276 of the second lead screw 274 and/or the internal thread 246 of the nut 236. In some embodiments, a more lubricious lubricant may be applied to the external thread 268 of the first lead screw 260 and/or the internal thread 272 of the second lead screw 274 while a less lubricious lubricant is applied to the external thread 276 of the second lead screw 274 and/or the internal thread 246 of the nut 236.

Figure 13:
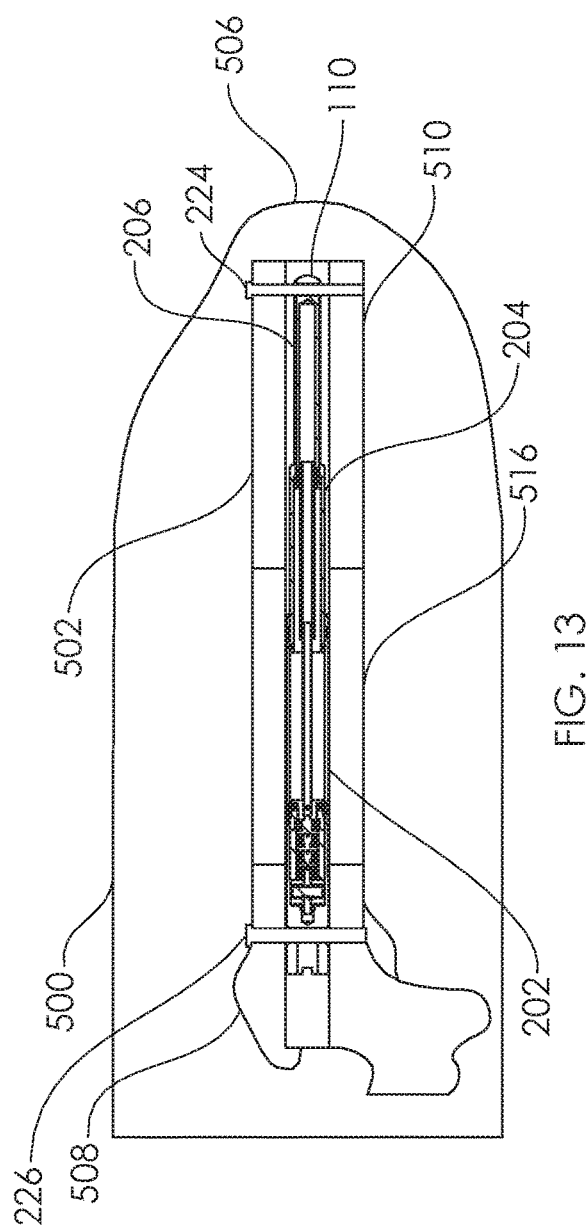
FIG. 13 illustrates a distraction device and residual limb after full distraction.

The longitudinal length of distraction possible for the second distraction rod 206 on its own may be between about 20 mm and about 90 mm, or between about 40 mm and about 70 mm, or about 50 mm. When the second distraction rod 206 has been fully distracted in relation to the first distraction rod 204, the first lead screw 260 will rotationally engage with the second lead screw 274, and thus the rotation of the first lead screw 260 will begin to turn the second lead screw 274 (e.g., in a one-to-one manner). In some embodiments, this occurs when the abutment 270 at the distal end 266 of the first lead screw 260 contacts a ledge 273 adjacent the internal thread 272 at the proximal end 275 of the second lead screw 274. As the first lead screw 260 continues to turn the second lead screw 274, the external thread 276 of the second lead screw 274 turns inside the internal thread 246 of the nut 236 of the second distraction rod 206, causing the second distraction rod 206 to longitudinally extend further in relation to the housing 202, but now, while also dragging the first distraction rod 204 along with it. The longitudinal length of distraction possible for the first distraction rod 204, after full distraction of the second distraction rod 206, may be between about 20 mm and about 90 mm, or between about 40 mm and about 70 mm, or about 50 mm. FIG. 13 shows the distraction rod 110 after the first distraction rod 204 and the second distraction rod 206 have been longitudinally extended in this manner in relation to the housing 202. Using this two-stage approach to distraction, a total distraction length of 100 mm, or even greater than 100 mm, may be possible with a housing 202 having a cavity 212 length of only 97 mm; thus the distraction length provided can be 102% of the housing cavity length. In some embodiments, the length of the distraction device 110 is 130 mm in a fully retracted state and 230 mm in a fully distracted state. Prior art devices that use only a single distraction rod generally provide distraction lengths of only 40% to 50% of the housing cavity length. The distraction device 110 may be also capable of retracting, by applying a moving magnetic field in an opposite direction, and causing the components to turn in opposite directions.

In some embodiments, the distraction device 110 (FIG. 4) may include features to limit the extent of distraction of the second distraction rod 206 in relation to the first distraction rod 204, and in the first distraction rod 204 in relation to the housing 202. For example, an abutment 289, or stop, may be located at the end of the longitudinal groove 216, or at another location at the proximal end 286 of the first distraction rod 204. An abutment 291, or stop, may be located at a distal, internal portion of the housing 202. For example, wherein the abutment 291 is a protrusion carried on the internal wall of the housing 202, or wherein it is a one end of the protrusion 209 of the cap 215. The abutment 291 may be configured to abut/engage the abutment 289 at a maximum degree of extension of the first distraction rod 204 in relation to the housing 202. Furthermore, an abutment 293, or stop, may be located at the end of the longitudinal groove 220, or at another location at the proximal end 294 of the second distraction rod 206. An abutment 297, or stop, may be located at a distal, internal portion of the first distraction rod 204, for example, wherein the abutment 297 is a protrusion carried on the internal wall of the first distraction rod 204. The abutment 297 may be configured to abut/engage the abutment 293 at a maximum degree of extension of the second distraction rod 206 in relation to the first distraction rod 204. Each of the abutments 289, 291, 293, 297 may be configured so that the second distraction rod 206, the first distraction rod 204, and the housing 202 do not get stuck or jammed against each other when the longitudinal extents are reached, thus allowing for retraction or shortening of the distraction device 110, if desired. The shortening of the distraction device 110 may be desired in certain situations in which compression of bone pieces is needed. This includes situations in which it is desired to form, reform, or improve a callus for osteogenesis. In some embodiments, the protrusions 209, 211 themselves may serve as the abutments 291, 297.

Figure 10:
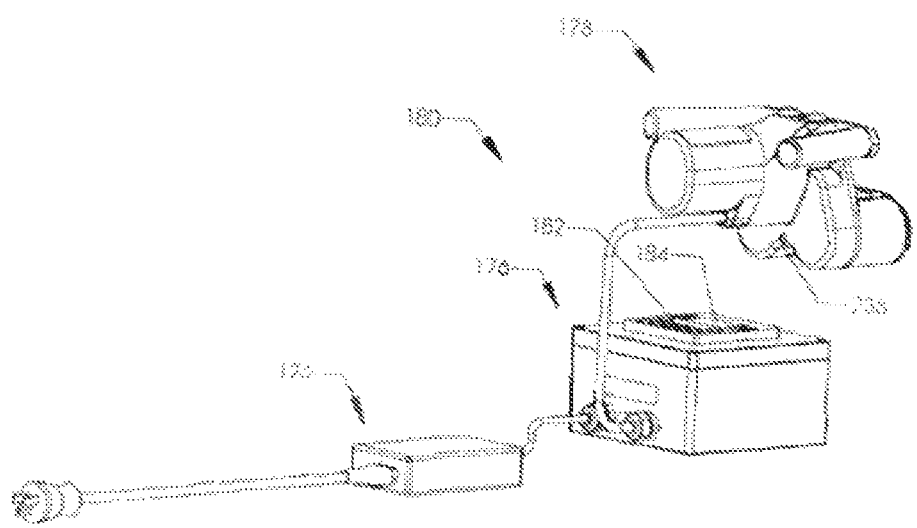
FIG. 10 illustrates an example external remote controller for wirelessly controlling and communicating with an implantable device.

The implantable adjustable system 100 incorporating a distraction device 110, as disclosed herein, may utilize an External Remote Controller (ERC). FIG. 10 illustrates an example of an External Remote Controller (ERC) 180 which may be used to non-invasively control the distraction device 110 by means of a magnetic coupling of torque. ERC 180 comprises a magnetic handpiece 178, a control box 176 (containing a processor) which may be integrated with the handpiece 178 and a power supply 174 such as a battery or external plug for connection to a standard power outlet. The control box 176 includes a control panel 182 having one or more controls (buttons, switches or tactile, motion, audio or light sensors) and a display 184. The display 184 may be visual, auditory, tactile, the like, or some combination of the aforementioned features, or any other display/UI described in this disclosure. The control box 176 may further contain a transceiver for communication with a transceiver in the implant and/or other external devices.

Figure 11:
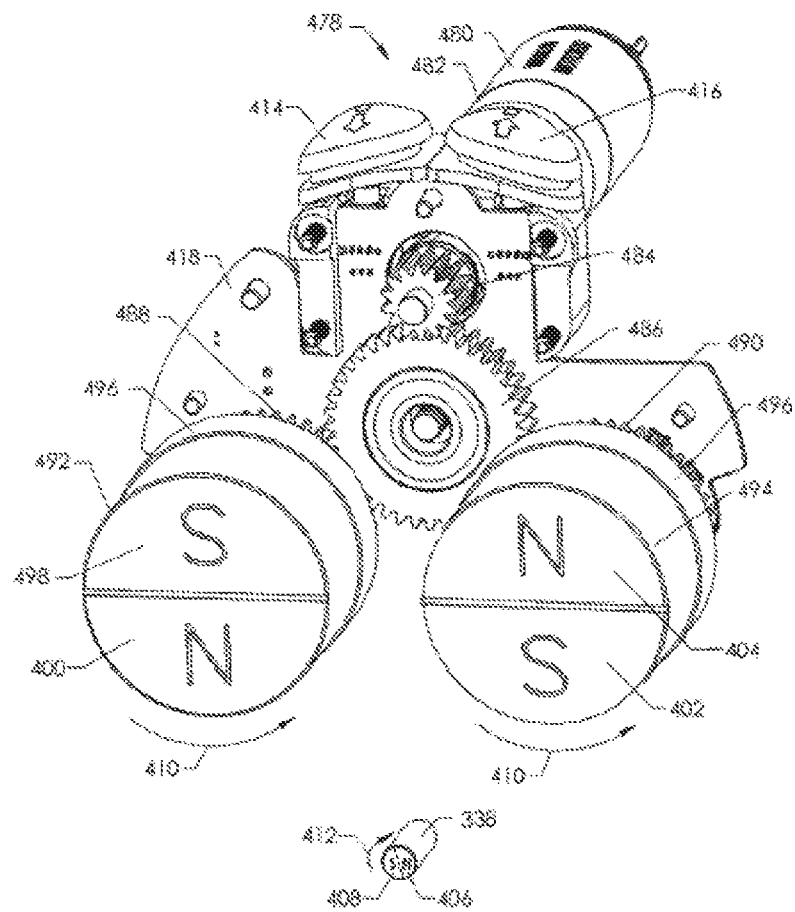
FIG. 11 illustrates the internal components of a handpiece of the external remote controller of FIG. 10.

FIG. 11 illustrates an internal assembly 478 of the magnetic handpiece 178 configured for applying a moving magnetic field to allow for non-invasive adjustment of the distraction device 110 by turning the magnet 338 within the distraction device 110. The magnet 338 of the distraction device 110 includes a north pole 406 and a south pole 408. A motor 480 with a gear box 482 outputs to a motor gear 484. The motor gear 484 engages and turns a central (idler) gear 486, which has the appropriate number of teeth to turn first and second magnet gears 488, 490 at identical rotational speeds. First and second magnets 492, 494 turn in unison with the first and second magnet gears 488, 490, respectively. Each magnet 492, 494 may be held within a respective magnet cup 496 (shown partially). An exemplary rotational speed may be 60 RPM or less. This speed range may be desired in order to limit the amount of current density included in the body tissue and fluids, to meet international guidelines or standards. As seen in FIG. 11, the south pole 498 of the first magnet 492 may be oriented the same as the north pole 404 of the second magnet 494, and likewise, the first magnet 492 has its north pole 400 oriented the same and the south pole 402 of the second magnet 494. As these two magnets 492, 494 turn synchronously together, they apply a complementary and additive moving magnetic field to the radially-poled, magnet 338. Magnets having multiple north poles (for example, two) and multiple south poles (for example, two) are also contemplated in each of the devices. Alternatively, a single magnet (e.g., a magnet with a larger diameter) may be used in place of the two magnets. As the two magnets 492, 494 turn in a first rotational direction 410 (e.g., counter-clockwise), the magnetic coupling causes the magnet 338 to turn in a second, opposite rotational direction 412 (e.g., clockwise). The rotational direction of the motor 480 may be controlled by buttons 414, 416. One or more circuit boards 418 contain control circuitry for both sensing rotation of the magnets 492, 494 and controlling the rotation of the magnets 492, 494.

FIGS. 7-9 and 12-13 illustrate the implantable adjustable system 100 incorporating a distraction device 110 and an External Remote Controller (ERC) 180 being used in a surgery and subsequent adjustment procedures to increase the length of a bone 502 in a residual limb 500. In some cases, the residual limb is a femur of an above-the-knee amputee. As seen in FIG. 7, the bone 502 may have an amputated end 504, and the residual limb 500 may have a stump surface 506. A prosthetic limb or prosthetic limb attachment which may be attached to a residual limb 500 may have problems fitting or functioning when attached to a residual limb 500 having insufficient bone 502 length. The medullary canal 514 of the bone 502 may be drilled or reamed to a diameter about equal or slightly larger than that of the distraction device 110 to be utilized. The bone 502 may be divided into a first bone portion 508 and a second bone portion 510 by creating an osteotomy 512. In FIG. 8, the distraction device 110 may be placed within the medullary canal 514 so that the one or more holes 210 are within the first portion 508 and the one or more holes 208 are within the second portion 510. During pre-operative planning, members of the surgical team will often assess both the condition and the coverage of soft tissues. The stump surface 506 may be modified, by stretching the skin or tissue, or by adding skin graft material, or performing plastic surgery, in order to create enough future available room for the bone 502 to increase in length inside the residual limb 500 in the area adjacent the stump surface 506. In addition, infection prevention measures are commonly performed. During pre-operative planning, several other factors are determined including: the amount of limb length discrepancy, the diameter of the medullary canal, the required length of distraction device 110 to be used, or the location of the planned osteotomy. In some cases, the distraction device may be implanted in an antegrade manner and in some cases in a retrograde manner. When implanted in an antegrade manner the distraction device 110 may be implanted via *piriformis* fossa entry. A retrograde approach may instead be chosen, for example, in patients with a severely abducted hip. In FIG. 9, bone screws 226, 224 are secured to the bone 502 through the holes 210, 208 in order to secure the distraction device 110 to the first and second bone portions 508, 510. The patient may be allowed to recover and at a later time, for example, about two to about ten days or about five days, the first distraction procedure may be performed. The ERC 180 may be placed on the residual limb 500 at a location adjacent the magnet 338, and is operated to distract the first bone portion 508 and the second bone portion 510 apart. The procedure may be repeated several times and may be performed by medical personnel, or the patient's family and friends, or even the patient themself. Exemplary distraction protocol may include distraction of about 0.50 mm to about 1.50 mm in longitudinal distraction per day. In some cases, it may include distraction of about 0.75 mm to about 1.25 mm in longitudinal distraction per day. In some cases, the distraction may be about 1.00 mm per day. This may be broken up into several distraction procedures per day, for example, about 0.33 mm, three times a day.

FIG. 12 illustrates the distraction device 110 in the bone 502 after the second distraction rod 206 has approximately been fully distracted in relation to the first distraction rod 204. Over the several weeks and/or months that the distraction procedures take place, a new bone growth section 516 of bone begins to form between the first portion 508 and the second portion 510. FIG. 13 illustrates the distraction device 110 in the bone 502 after the first distraction rod 204 has approximately been fully distracted in relation to the housing 202. After the desired final distraction length is reached, distraction procedures are discontinued, and the new bone growth section 516 may be allowed time to fully consolidate. The distraction device 110 can continue to provide stability to the bone 502 of the residual limb 500 while the bone 502 is allowed to consolidate and after the bone has consolidated. After consolidation, the distraction device 110 may then be removed from the patient, though in some cases, the distraction device 110 may be left in place within the bone 502.

Figure 14:
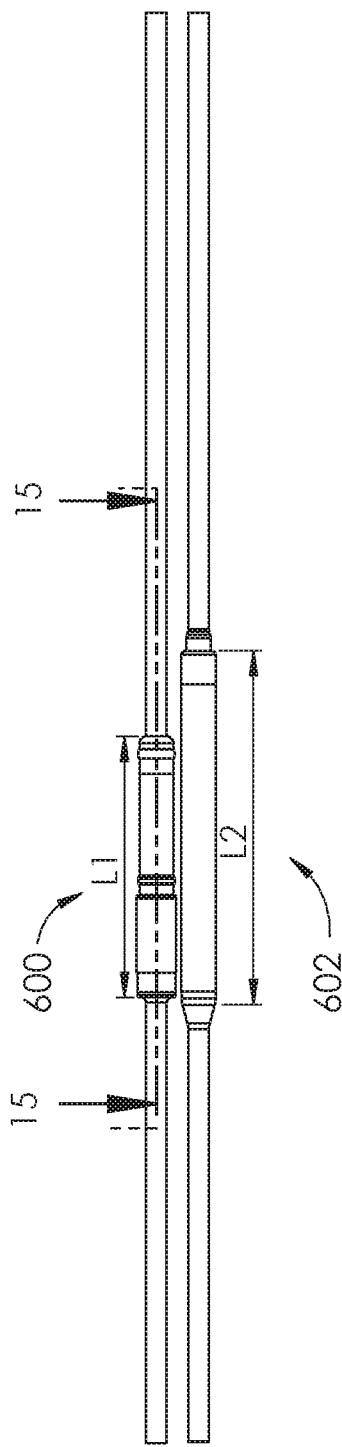
FIG. 14 illustrates a distraction device as disclosed herein placed next to a distraction device already in the prior art.
Figure 15:
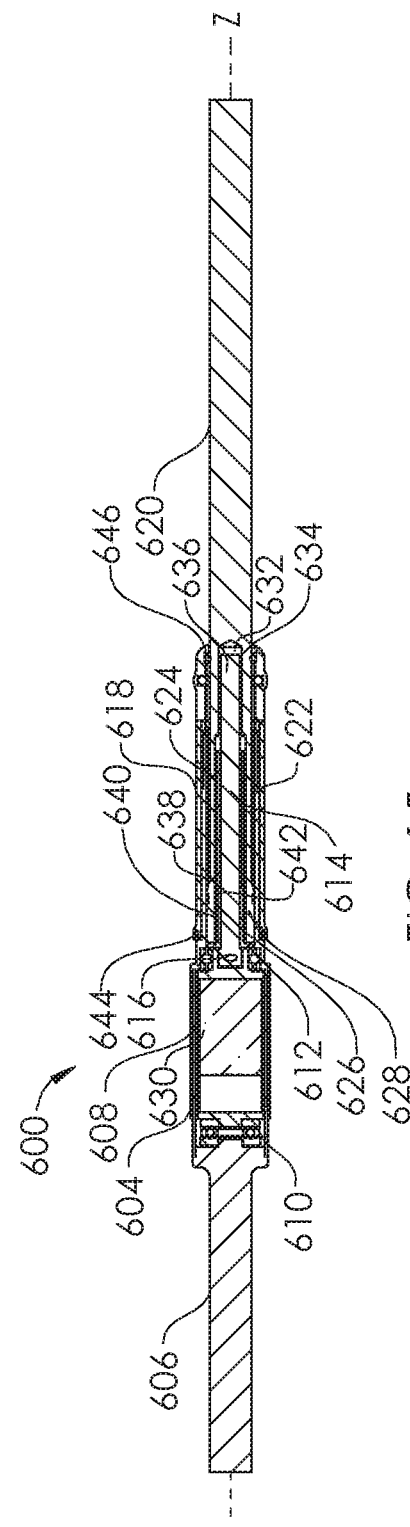
FIG. 15 illustrates a sectional view of the distraction device of FIG. 14 taken along line 15-15.
Figure 16:
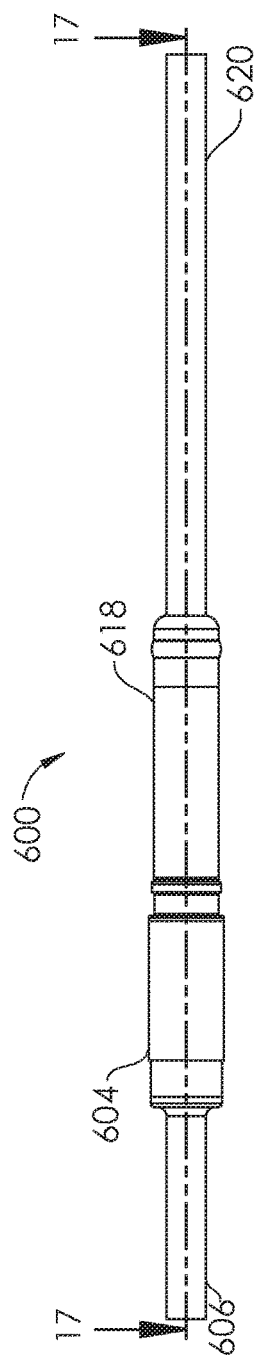
FIG. 16 illustrates the distraction device of FIGS. 14 and 15 in a partially distracted configuration.
Figure 17:
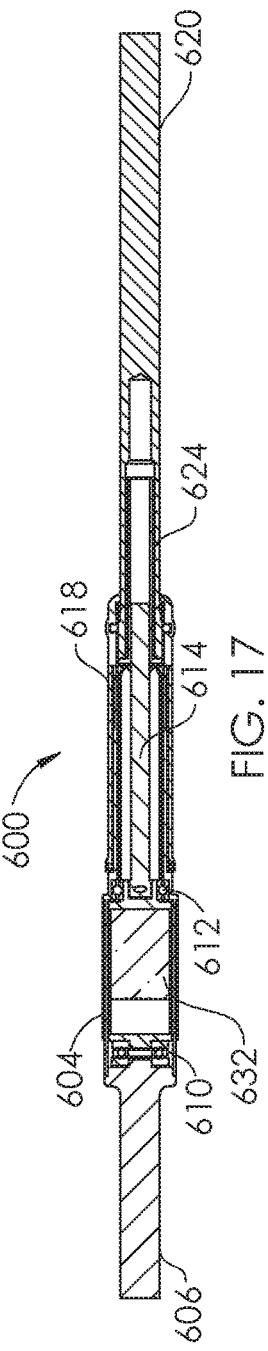
FIG. 17 illustrates a sectional view of the distraction device of FIG. 16 taken along line 17-17.
Figure 18:
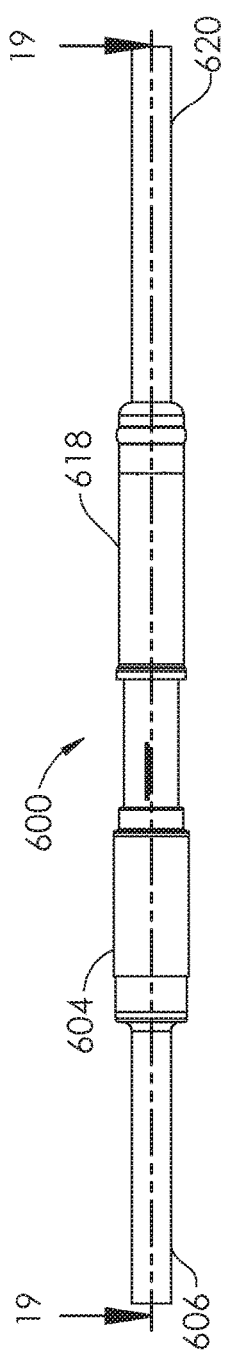
FIG. 18 illustrates the distraction device of FIGS. 14-17 in a fully distracted configuration.
Figure 19:
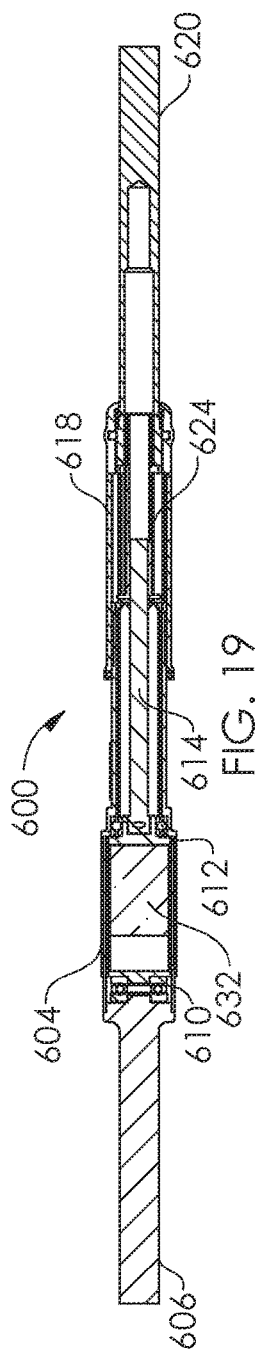
FIG. 19 illustrates a sectional view of the distraction device of FIG. 18 taken along line 19-19.

FIG. 14 illustrates one embodiment of a distraction device 600 placed next to a prior art distraction device 602. The distraction device 600 may be capable of distracting about 50 mm, as is the prior art distraction device 602, however the length $L_1$ of the housing portion of the distraction device 600 is over 25% percent shorter than the length $L_2$ of the housing portion of the prior art distraction device 602. The treatment of early onset scoliosis or adolescent idiopathic scoliosis is generally performed on small, thin patients having little space in their surgical sites to implant large device housings. Therefore, high efficiency adjustable distraction devices (total distraction length to housing length ratio) may allow more patients to be treated. Turning to FIG. 15, the distraction device 600 includes a housing 604 which may be connected to a rod 606 by welding or other bonding methods. In some embodiments, the rod 606 and the housing 604 may be formed from the same monolithic material. Within the housing 604, a driving element including a magnetic assembly 608 (containing a radially-poled magnet 630) may be held longitudinally stationary between a thrust bearing 610 and a radial bearing 612. Though gear modules may be incorporated, as in the embodiment of FIG. 1, in FIG. 15 the distraction device is depicted in an embodiment wherein the magnetic assembly 608 may be directly connected to a first lead screw 614 by a pin 616. In the distraction device 600 embodiment of FIG. 15, a first distraction rod 618 is telescopically carried on the outside of the housing 604, and is longitudinally displaceable along a longitudinal axis Z. A second distraction rod 620 may be telescopically carried within a cavity 622 within the housing 604, and is longitudinally displaceable along the longitudinal axis Z. The second distraction rod 620 has a cavity 632 which allows space for the first lead screw 614. A second lead screw 624 having an internal thread 626 at its proximal end 628 may be carried annularly between the first lead screw 614 and the second distraction rod 620. Rotation of the magnetic assembly 608 by a remotely-applied moving magnetic field causes the first lead screw 614 to rotate within the internal thread 626 of the second lead screw 624, thus causing the second lead screw 624 and the second distraction rod 620 to longitudinally displace in relation to the housing 604 and the first distraction rod 618. The distraction device 600 with the second distraction rod 620 fully displaced in relation to the first distraction rod 618 is illustrated in FIGS. 16-17. At this fully displaced condition, an abutment 634 at the distal end 636 of the first lead screw 614 abuts a ledge 638 at the proximal end 640 of the second lead screw 624. As the first lead screw 614 continues to turn, this causes the second lead screw 624 to turn in unison with the first lead screw 614, thus turning of the second lead screw 624 within an inner thread 642 within the cavity 632 of the second distraction rod 620. This causes the second distraction rod 620 to longitudinally displace further from the housing 604, dragging the first distraction rod 618 along with it. The distraction device 600 with the first distraction rod 618 fully displaced in relation to the housing 604 is illustrated in FIGS. 18-19. A first o-ring 644 held in a circumferential groove in the first distraction rod 618 forms a dynamic seal between the first distraction rod 618 and the housing 604. A second o-ring 646 held in a circumferential groove in the first distraction rod 618 forms a dynamic seal between the first distraction rod 618 and the second distraction rod 620. The distraction device 600 may be capable of retracting, by applying a moving magnetic field in an opposite direction, and causing the components to turn in opposite directions.

The distraction device 600 may comprise features to limit or stop rotation between the first distraction rod 618 and the housing 604, and/or between the second distraction rod 620 and the first distraction rod 618. For example, the longitudinal grooves, 216, 220 and protrusions 209, 211 of the embodiment of FIGS. 1-6 may be incorporated into the design of the distraction device 600, so that there may be substantially no rotation possible between the second distraction rod 620 and the housing 604. For example, if the second distraction rod 620 is rigidly coupled to a first vertebra (e.g., via a screw or hook) and the housing 604 (e.g., via rod 606) is coupled to a second vertebra (e.g., via a screw or hook), rotation may be substantially limited between the first vertebra and the second vertebra, so that no unwanted movement between them can occur. Furthermore, the abutments 289, 291, 293, 297 of the embodiment of FIGS. 1-6 may be incorporated into the design of the distraction device 600 in order to control the extent of lengthening of the first distraction rod 618 in relation to the housing 604, and/or the second distraction rod 620 in relation to the first distraction rod 618.

Figure 20:
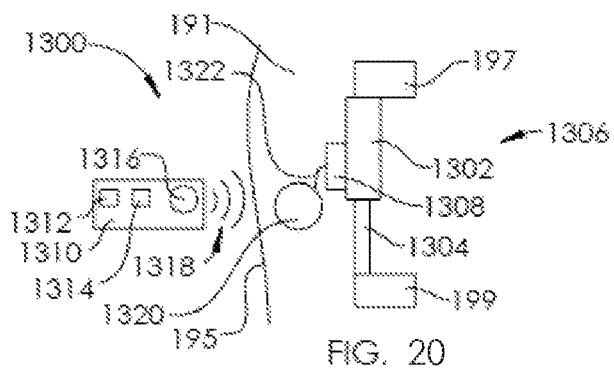
FIGS. 20-23 schematically illustrate various alternate sources of a driving element of a non-invasively adjustable spinal implant.

FIGS. 20-23 illustrate embodiments of alternate sources to the rotatable magnetic assembly as the driving element 242 of a non-invasively adjustable implant. FIG. 20 illustrates a non-invasively adjustable system 1300 comprising an implant 1306 having a first implant portion 1302 and a second implant portion 1304, the second implant portion 1304 non-invasively displaceable with relation to the first implant portion 1302. The first implant portion 1302 may be secured to a first bone portion 197 and the second implant portion 1304 may be secured to a second bone portion 199 within a patient 191. A motor 1308 may be operable to cause the first implant portion 1302 and the second implant portion 1304 to displace relative to one another. An external remote controller (ERC) 1310 has a control panel 1312 for input by an operator, a display 1314 and a transmitter 1316. The transmitter 1316 sends a control signal 1318 through the skin 195 of the patient 191 to an implanted receiver 1320. Implanted receiver 1320 communicates with the motor 1308 via a conductor 1322. The motor 1308 may be powered by an implantable battery, or may be powered or charged by inductive coupling.

Figure 21:
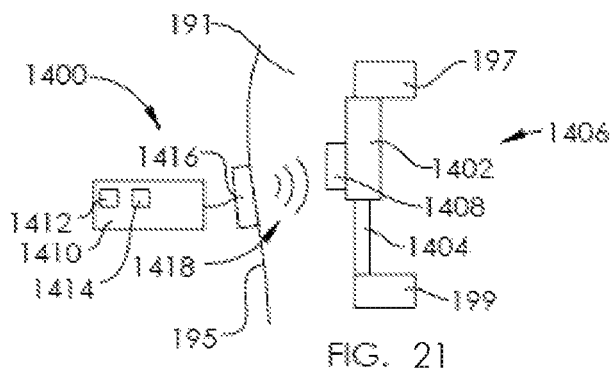

FIG. 21 illustrates a non-invasively adjustable system 1400 comprising an implant 1406 having a first implant portion 1402 and a second implant portion 1404, the second implant portion 1404 non-invasively displaceable with relation to the first implant portion 1402. The first implant portion 1402 may be secured to a first bone portion 197 and the second implant portion 1404 may be secured to a second bone portion 199 within a patient 191. An ultrasonic motor 1408 may be operable to cause the first implant portion 1402 and the second implant portion 1404 to displace relative to one another. An external remote controller (ERC) 1410 has a control panel 1412 for input by an operator, a display 1414 and an ultrasonic transducer 1416, which may be coupled to the skin 195 of the patient 191. The ultrasonic transducer 1416 produces ultrasonic waves 1418 which pass through the skin 195 of the patient 191 and operate the ultrasonic motor 1408.

Figure 22:
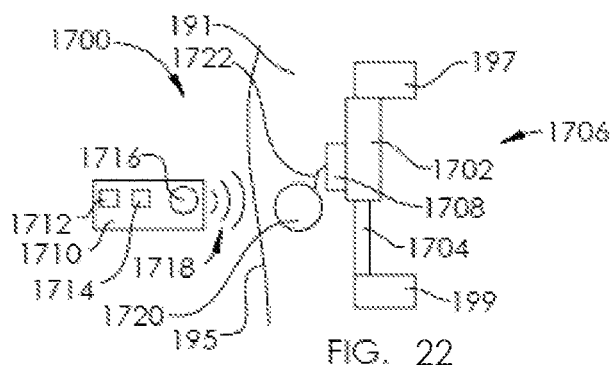

FIG. 22 illustrates a non-invasively adjustable system 1700 comprising an implant 1706 having a first implant portion 1702 and a second implant portion 1704, the second implant portion 1704 non-invasively displaceable with relation to the first implant portion 1702. The first implant portion 1702 may be secured to a first bone portion 197 and the second implant portion 1704 may be secured to a second bone portion 199 within a patient 191. A shape memory actuator 1708 may be operable to cause the first implant portion 1702 and the second implant portion 1704 to displace relative to one another. An external remote controller (ERC) 1710 has a control panel 1712 for input by an operator, a display 1714 and a transmitter 1716. The transmitter 1716 sends a control signal 1718 through the skin 195 of the patient 191 to an implanted receiver 1720. Implanted receiver 1720 communicates with the shape memory actuator 1708 via a conductor 1722. The shape memory actuator 1708 may be powered by an implantable battery, or may be powered or charged by inductive coupling.

Figure 23:
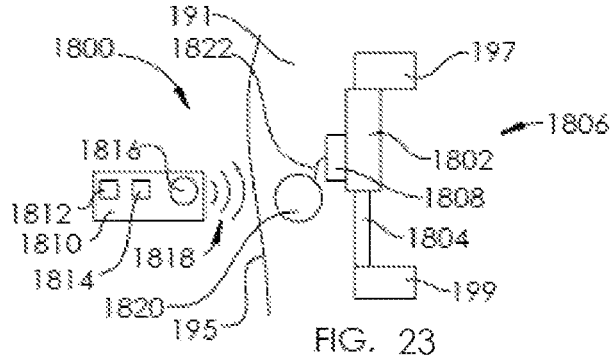

FIG. 23 illustrates a non-invasively adjustable system 1800 comprising an implant 1806 having a first implant portion 1802 and a second implant portion 1804, the second implant portion 1804 non-invasively displaceable with relation to the first implant portion 1802. The first implant portion 1802 may be secured to a first bone portion 197 and the second implant portion 1804 may be secured to a second bone portion 199 within a patient 191. A hydraulic pump 1808 may be operable to cause the first implant portion 1802 and the second implant portion 1804 to displace relative to one another. An external remote controller (ERC) 1810 has a control panel 1812 for input by an operator, a display 1814 and a transmitter 1816. The transmitter 1816 sends a control signal 1818 through the skin 195 of the patient 191 to an implanted receiver 1820. Implanted receiver 1820 communicates with the hydraulic pump 1808 via a conductor 1822. The hydraulic pump 1808 may be powered by an implantable battery, or may be powered or charged by inductive coupling. The hydraulic pump 1808 may alternatively be replaced by a pneumatic pump.

Though not illustrated, another driving element 242 may include a magnetorestrictive element. A number of materials may be used to produce the components like the housing, first distraction rod, second distraction rod, first lead screw, and second lead screw, including but not limited to titanium, titanium alloys, titanium 6-4, cobalt-chromium alloys, and stainless steel.

Figure 24:
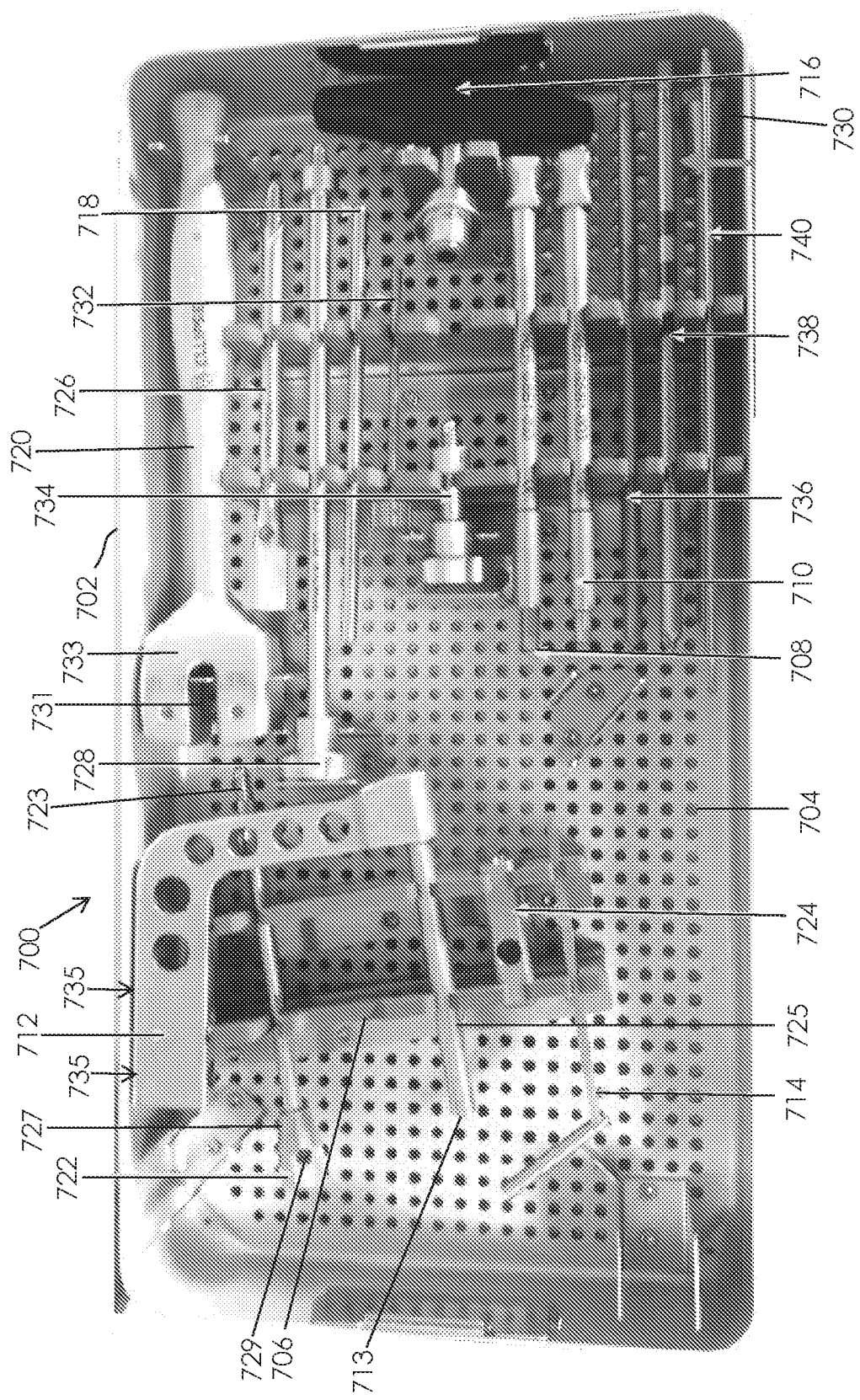
FIG. 24 illustrates a kit containing instruments for use with distraction devices according to embodiments described herein.

FIG. 24 illustrates a sterilizable kit 700 of instruments for use with embodiments of the distraction device described herein. A sterilizable tray 702 includes holes 704 which may allow gas or steam to enter the tray 702 when the tray 702 is covered by a cover (not shown). One or more dividers 706 may be constructed of a pliable material (such as silicone) and provide cavities, holes or slits therebetween for securing the one or more instruments. A drill bushing 708 and a guide tube 710 may be used for guiding one or more drills or reamers, for example, while drilling holes within the medullary canal of a bone. Prior to this, a hole may be made in the skin, soft tissue, and/or bone using a piercing rod 730. Vent holes may be made in the bone prior to reaming in order to avoid high intramedullary pressures which may cause fat embolism, or other complications. The medullary canal may in some cases be reamed to a slightly larger diameter than the diameter of the distraction device 110, for example 0.5 mm larger, or may be reamed 1 mm larger or 2 mm larger. A guide arm 712 may be connected at a distal end 713 of its guide tube 725 to a the housing 202 of the distraction device 110 of FIG. 6, for example an engagement portion 213 at the proximal end 221 of the housing 202. The engagement portion 213 may include a cavity, for example, a threaded cavity, and may be engageable via a distal end 723 of a locking rod 722. The locking rod 722 may be inserted through the guide tube 725 of the guide arm 712. The locking rod 722 may be tightened (or untightened) by turning a handle 727, or by placing a tommy bar 718 through a transverse hole 729 at or near the handle 727 of the locking rod 722. The drill bushing 708 and a guide tube 710 may be placed through transverse holes 735 in the guide arm, or a guide extension 724 may be secured to the end 737 of the guide arm 712. One or more additional transverse holes 735 may be within the guide extension for placement of the drill bushing 708 and a guide tube 710. During the manipulation of the distraction device 110 with the instruments, soft tissue of the patient may be protected with a soft tissue protector 714. Some or all of the cylindrical instrument components may be rotated with increased torque by attaching a T-handle 716. If the distraction device 110 and the guide arm 712 need to be removed, for example from a reamed medullary canal in the bone, a mallet 720 may be placed so that a slit 731 in the head 733 of the mallet 720 is around the guide tube 725 of the guide arm 712. The mallet 720 may be then caused to impact against the handle 727 of the guide arm 712 to aid in the removal of the distraction device 110 and guide arm 712. After implantation of the distraction device 110 and its securement to the bone by one or more bone screws, the guide arm 112 may be removed, by unscrewing the locking rod 722 from the engagement portion 213 of the distraction device 110.

If the distraction device 110 is to be removed from the bone (for example after the bone has been lengthened and allowed to consolidate), after the bone screws are removed, an extractor 726 may be attached to the engagement portion 213 of the distraction device 110 and the distraction device may be pulled out of the medullary canal by hand, or may be hammered out using the mallet 731. The distal end of the extractor 726 may have a male or female thread that can be engaged with the proximal end 221 of the housing 202 of the distraction device 110. An additional removal rod 728 may be used. Further instruments that may be used include a locking key 732, a short impactor 734, a hexagon headed river 736 and a locking driver 738. Bone screws 740 may be secured with a screw capture rod 740. Other instruments and uses of instruments are described in U.S. Pat. No. 8,449,543, which is incorporated herein by reference in its entirety.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A system for moving a portion of a patient's body comprising:
    a housing having a first cavity;
    a first distraction rod having a proximal end, a distal end, and a second cavity, wherein the first distraction rod is configured for telescopic displacement relative to the first cavity;
    a second distraction rod having a proximal end and a distal end, wherein the second distraction rod is configured for telescopic displacement from within the second cavity; and
    a drive system configured to move the first distraction rod and the second distraction rod relative to the housing, wherein the second distraction rod is configured to be substantially fully displaced from within the second cavity before the first distraction rod begins to displace from within the first cavity.

2. The system of claim 1, wherein the drive system comprises a driving element that is at least partially located within the housing.

3. The system of claim 2, wherein the driving element is remotely controllable.

4. The system of claim 3, wherein the driving element comprises at least one of a permanent magnet, an inductively coupled motor, an ultrasonically actuated motor, a subcutaneous hydraulic pump, a shape memory-driven actuator, and a magnetorestrictive element.

5. The system of claim 3, wherein the driving element comprises a radially-poled permanent magnet configured for rotation within the housing.

6. The system of claim 5, wherein the radially-poled permanent magnet is configured to be rotated by application of an externally applied rotating magnetic field.

7. The system of claim 1, wherein the first distraction rod and the housing are restrained to prevent substantially all axial rotation with respect to each another about the longitudinal axis.

8. The system of claim 1, wherein the second distraction rod and the first distraction rod are restrained to prevent substantially all rotation with respect to each another about the longitudinal axis.

9. The system of claim 1, wherein the second distraction rod and the housing are restrained to prevent substantially all rotation with respect to each about the longitudinal axis.

10. The system of claim 1, further comprising:
a first stop at the proximal end of the second distraction rod; and
a second stop at the distal end of the first distraction rod, wherein the first stop of the second distraction rod is configured to engage the second stop of the first distraction rod when the second distraction rod is substantially fully displaced from within the second cavity.

11. The system of claim 1, wherein the drive system is configured to move the first distraction rod in relation to the housing and move the second distraction rod in relation to the first distraction rod.

12. A method of modifying a residual limb of a patient comprising the steps of:
providing a distraction device comprising:
a housing having a first cavity;
a first distraction rod having a proximal end, a distal end, and a second cavity, wherein the first distraction rod is telescopically displaceable relative to the first cavity;
a second distraction rod having a proximal end and a distal end, wherein the second distraction rod is telescopically displaceable from within the second cavity; and
a drive system configured to move of the first distraction rod and the second distraction rod with relative to the housing,
wherein the second distraction rod is configured to be substantially fully displaced from within the second cavity before the first distraction rod begins to displace from within the first cavity;
decoupling a first portion of a bone within the residual limb from a second portion of the bone;
attaching the housing to one of the first portion and the second portion of the bone within the residual limb; and
attaching the second distraction rod to the other of the first portion and the second portion of the bone within the residual limb, wherein the drive system is configured to be actuated so as to increase at least one of a force and a distance between the first portion and the second portion of the bone.

13. The method of claim 12, further comprising modifying skin of the residual limb such that an additional internal space is made within the residual limb to facilitate an axial elongation of the bone.

14. The method of claim 12, wherein the bone comprises a femur.

15. The method of claim 12, wherein the drive system comprises a driving element at least partially located within the housing.

16. The method of claim 15, wherein the driving element is non-invasively actuatable.

17. The method of claim 16, wherein the driving element comprises at least one of a permanent magnet, an inductively coupled motor, an ultrasonically actuated motor, a subcutaneous hydraulic pump, a shape memory-driven actuator, and a magnetorestrictive element.

18. The method of claim 16, wherein the driving element comprises a radially-poled permanent magnet configured for rotation within the housing.

19. The method of claim 18, wherein the radially-poled permanent magnet is configured to be rotated by application of an externally applied rotating magnetic field.

* * * * *